US009624541B2

(12) United States Patent
Watelet et al.

(10) Patent No.: US 9,624,541 B2
(45) Date of Patent: Apr. 18, 2017

(54) COMBINATION OF BIOMARKERS FOR THE DETECTION AND EVALUATION OF HEPATITIS FIBROSIS

(75) Inventors: Bénédicte Watelet, Saint Clement de Riviere (FR); Tarik Asselah, Paris (FR); Ivan Bieche, Suresnes (FR); Isabelle Catherine Batxelli, Aigues-Vives (FR); Nathalie Jullian, Montrouge (FR); Michel Vidaud, Fontenay Sous Bois (FR); Patrick Marcellin, Paris (FR); Daniel Laune, Grabels (FR); Mohammad Afshar, Paris (FR); Eve Laure Mathieu, Montpellier (FR)

(73) Assignees: BIO-RAD INNOVATIONS, Marnes la Coquette (FR); ARIANA PHARMACEUTICALS, Paris (FR); INSTITUT NATIONAL DE LA SANTE ET DE LA RECHERCHE MEDICALE, Paris (FR); ASSISTANCE PUBLIQUE—HOPITAUX DE PARIS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 363 days.

(21) Appl. No.: 13/984,702

(22) PCT Filed: Feb. 9, 2012

(86) PCT No.: PCT/EP2012/052234
§ 371 (c)(1),
(2), (4) Date: Aug. 9, 2013

(87) PCT Pub. No.: WO2012/107530
PCT Pub. Date: Aug. 16, 2012

(65) Prior Publication Data
US 2013/0323720 A1    Dec. 5, 2013

Related U.S. Application Data

(60) Provisional application No. 61/440,986, filed on Feb. 9, 2011.

(30) Foreign Application Priority Data

Feb. 9, 2011   (FR) ..................................... 11 51022

(51) Int. Cl.
*C12Q 1/68*   (2006.01)
*G01N 33/576*   (2006.01)
*C12Q 1/70*   (2006.01)

(52) U.S. Cl.
CPC ......... *C12Q 1/6876* (2013.01); *C12Q 1/6883* (2013.01); *G01N 33/576* (2013.01); *C12Q 1/706* (2013.01); *C12Q 2600/106* (2013.01); *C12Q 2600/112* (2013.01); *C12Q 2600/158* (2013.01); *G01N 2800/085* (2013.01); *G01N 2800/60* (2013.01); *G01N 2800/7052* (2013.01)

(58) Field of Classification Search
CPC ............ C12Q 2600/158; C12Q 1/6883; C12Q 2600/136; C12Q 1/6886
USPC ............................................................ 435/5
See application file for complete search history.

(56) References Cited

U.S. PATENT DOCUMENTS

| 6,631,330 | B1 | 10/2003 | Poynard |
| 7,824,871 | B2* | 11/2010 | Younossi et al. ............ 435/7.21 |
| 2007/0172907 | A1* | 7/2007 | Volker et al. .................... 435/15 |
| 2008/0161203 | A1* | 7/2008 | Su et al. ......................... 506/18 |
| 2010/0041069 | A1 | 2/2010 | Lederkremer |
| 2010/0136579 | A1 | 6/2010 | Tseng et al. |
| 2010/0203553 | A1 | 8/2010 | Abdeen et al. |

FOREIGN PATENT DOCUMENTS

| WO | WO 02/16949 A1 | 2/2002 |
| WO | WO 2006/082522 A1 | 8/2006 |
| WO | WO 2006/103570 A2 | 10/2006 |

OTHER PUBLICATIONS

Shin et al., "SPP1 polymorphisms associated with HBV clearance and HCC occurrence", 2007, International Journal of Epidemiology, 36:1001-1008.*
Asselah et al., "Liver Gene Expression Signature of Mild Fibrosis in Patients with Chronic Hepatitis C", 2005, 129:2064-2075.*
Patouraux et al, "The Osteopontin Level in Liver, Adipose Tissue and Serum Is Correlated with Fibrosis in Patients with Alcoholic Liver Disease", PLoS ONE, vol. 7, Issue 4, e35612, Apr. 2012.
Gene List, "Human Genome CGH Microarray 44B G4410B", Agilent Technologies, 2007.
Shin et al, "SPP1 polymorphisms associated with HBV clearance and HCC occurrence", International Journal of Epidemiology, vol. 36, No. 5, Oct. 2007, pp. 1001-1008.

(Continued)

*Primary Examiner* — Stacy B Chen
(74) *Attorney, Agent, or Firm* — Saliwanchik, Lloyd & Eisenschenk

(57) ABSTRACT

The application concerns means for determining the stage of hepatic tissue damage, in particular the hepatic fibrosis score of subjects infected with one or more hepatitis viruses. In particular, the means of the invention involve measuring the levels of expression of selected genes, said selected genes being:
SPP1, and
at least one gene from among A2M and VIM, and
at least one gene from among IL8, CXCL10 and ENG, and
optionally, at least one gene from among the list of the following sixteen genes: IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1.

3 Claims, 4 Drawing Sheets

(56) References Cited

OTHER PUBLICATIONS

Schmilovitz-Weiss et al, "Serum globulin levels in predicting the extent of hepatic fibrosis in patients with recurrent post-transplant hepatitis C infection", Clinical Transplantation 2007, vol. 21, No. 3, pp. 391-397.

Castera et al, "Prospective Comparison of Transient Elastography, Fibrotest, APRI, and Liver Biopsy for the Assessment of Fibrosis in Chronic Hepatitis C", Gastroenterology 2005; 128:343-350.

Shaheen et al, "FibroTest and FibroScan for the Prdiction of Hepatitis C-Related Fibrosis: A Systematic Review of Diagnostic Test Accuracy", American Journal of Gastroenterology, 2007; 102:2589-2600.

Asselah et al, "Liver gene expression signature to predict response to pegylated interferon plus ribavirin combination therapy in patients with chronic hepatitis C", Gut 2008; 57:516-524.

Asselah et al, "Liver Gene Expression Signature of Mild Fibrosis in Patients With Chronic Hepatitis C", Gastroenterology 2005; 129:2064-2075.

Bieche et al, "Molecular profiling of early stage liver fibrosis in patients with chronic hepatitis C virus infection", Virology 332 (2005) 130-144.

Chen et al, "Cell-Type Specific Gene Expression Signature in Liver Underlies Response to Interferon Therapy in Chronic Hepatitis C Infection", Gastroenterology 2010; 138:1123-1133.

Abstract Duces et al, No. 684; Journal of Hepatology, Apr. 2010, vol. 52, Supplement 1, p. S267.

Abstract Duces et al, No. T1958; Gastroenterology, May 2010, vol. 138, Issue 5, Supplement 1, p. S-837.

Abstract Duces et al, No. T2000; Gastroenterology, May 2010, vol. 138, Issue 5, Supplement 1, p. S-837.

Poster shown at the Meeting of the American Association of the Study of Liver Diseases (AASLD) on Sep. 2, 2010.

French Search Report dated Jan. 31, 2012, issued in connection with FR 1151022.

International Search Report dated Jun. 25, 2012, issued in connection with PCT/EP2012/052234.

Huang et al, "Plasma osteopontin concentration correlates with the severity of hepatic fibrosis and inflammation in HCV-infected subjects", Clinica Chimica Acta 411 (2010) 675-678.

International Search Report for PCT/EP2012/052234 mailed Jun. 25, 2012.

Written Opinion of the International Searching Authority mailed Jun. 25, 2012.

S. Hyoung et al., "SPP1 Polymorphisms Associated with HBV Clearance and HCC Occurrence", International Journal of Epidemiology, vol. 36, No. 5, Oct. 2007, pp. 1001-1008.

S. Hemda et al., "Serum Globulin Levels in Predicting the Extent of Hepatic Fibrosis in Patients with Recurrent Post-Transplant Hepatitis C Infection", Clinical Transplantation, vol. 21, No. 3, May 2007, pp. 391-397.

\* cited by examiner

SEQUENCE LISTING

```
<160> NUMBER OF SEQ ID NOS: 46

<210> SEQ ID NO 1
<211> LENGTH: 24
<212> TYPE: DNA
<213> ORGANISM: Homo sapiens

<400> SEQUENCE: 1
gcaagtaaaa accaaggtct tcca                                            24

<210> SEQ ID NO 2
<211> LENGTH: 23
<212> TYPE: DNA
<213> ORGANISM: Homo sapiens

<400> SEQUENCE: 2
tccagtcaat tccaccactg ttc                                             23

<210> SEQ ID NO 3
<211> LENGTH: 23
<212> TYPE: DNA
<213> ORGANISM: Homo sapiens

<400> SEQUENCE: 3
tcgcagacct gacatccagt acc                                             23
```

```
<210> SEQ ID NO 4
<211> LENGTH: 23
<212> TYPE: DNA
<213> ORGANISM: Homo sapiens

<400> SEQUENCE: 4
ccattcaact cctcgctttc cat                                              23

<210> SEQ ID NO 5
<211> LENGTH: 23
<212> TYPE: DNA
<213> ORGANISM: Homo sapiens

<400> SEQUENCE: 5
ctccctctgg ttgataccca ctc                                              23

<210> SEQ ID NO 6
<211> LENGTH: 25
<212> TYPE: DNA
<213> ORGANISM: Homo sapiens

<400> SEQUENCE: 6
agaagtttcg ttgataacct gtcca                                            25

<210> SEQ ID NO 7
<211> LENGTH: 25
<212> TYPE: DNA
<213> ORGANISM: Homo sapiens

<400> SEQUENCE: 7
ctgactctaa gtggcattca aggag                                            25

<210> SEQ ID NO 8
<211> LENGTH: 25
<212> TYPE: DNA
<213> ORGANISM: Homo sapiens

<400> SEQUENCE: 8
ggttgattac taatgctgat gcagg                                            25

<210> SEQ ID NO 9
<211> LENGTH: 24
<212> TYPE: DNA
<213> ORGANISM: Homo sapiens

<400> SEQUENCE: 9
caccggaagg aaccatctca ctgt                                             24

<210> SEQ ID NO 10
<211> LENGTH: 23
<212> TYPE: DNA
<213> ORGANISM: Homo sapiens

<400> SEQUENCE: 10
tccttggcaa aactgcacct tca                                              23

<210> SEQ ID NO 11
<211> LENGTH: 24
<212> TYPE: DNA
<213> ORGANISM: Homo sapiens

<400> SEQUENCE: 11
```

```
cacaacatgc agatctggac cact                                          24

<210> SEQ ID NO 12
<211> LENGTH: 20
<212> TYPE: DNA
<213> ORGANISM: Homo sapiens

<400> SEQUENCE: 12
tgggagcttg aagccacgaa                                               20

<210> SEQ ID NO 13
<211> LENGTH: 19
<212> TYPE: DNA
<213> ORGANISM: Homo sapiens

<400> SEQUENCE: 13
acgtgaggat ggcagcgtt                                                19

<210> SEQ ID NO 14
<211> LENGTH: 25
<212> TYPE: DNA
<213> ORGANISM: Homo sapiens

<400> SEQUENCE: 14
gaagggttac caaatcccac tttat                                         25

<210> SEQ ID NO 15
<211> LENGTH: 21
<212> TYPE: DNA
<213> ORGANISM: Homo sapiens

<400> SEQUENCE: 15
ggttttcgtg gttcacatcc c                                             21

<210> SEQ ID NO 16
<211> LENGTH: 22
<212> TYPE: DNA
<213> ORGANISM: Homo sapiens

<400> SEQUENCE: 16
cccatcatca tgacctggtc tt                                            22

<210> SEQ ID NO 17
<211> LENGTH: 21
<212> TYPE: DNA
<213> ORGANISM: Homo sapiens

<400> SEQUENCE: 17
gaccacaggc catcacagtc c                                             21

<210> SEQ ID NO 18
<211> LENGTH: 25
<212> TYPE: DNA
<213> ORGANISM: Homo sapiens

<400> SEQUENCE: 18
tgtaccccac agcatagtca gtgtt                                         25

<210> SEQ ID NO 19
<211> LENGTH: 21
<212> TYPE: DNA
<213> ORGANISM: Homo sapiens

<400> SEQUENCE: 19
```
cctccggctc ctgctcctct t                                      21

<210> SEQ ID NO 20
<211> LENGTH: 22
<212> TYPE: DNA
<213> ORGANISM: Homo sapiens

<400> SEQUENCE: 20
ggcagttctt ggtctcgtca ca                                     22

<210> SEQ ID NO 21
<211> LENGTH: 24
<212> TYPE: DNA
<213> ORGANISM: Homo sapiens

<400> SEQUENCE: 21
tcgaaaagat gctgaacagt gaca                                   24

<210> SEQ ID NO 22
<211> LENGTH: 22
<212> TYPE: DNA
<213> ORGANISM: Homo sapiens

<400> SEQUENCE: 22
cttcaggaac agccaccagt ga                                     22

<210> SEQ ID NO 23
<211> LENGTH: 25
<212> TYPE: DNA
<213> ORGANISM: Homo sapiens

<400> SEQUENCE: 23
gtttacgcgt tacgctgaga gtaaa                                  25

<210> SEQ ID NO 24
<211> LENGTH: 21
<212> TYPE: DNA
<213> ORGANISM: Homo sapiens

<400> SEQUENCE: 24
cgttcttcag ggaggctacc a                                      21

<210> SEQ ID NO 25
<211> LENGTH: 24
<212> TYPE: DNA
<213> ORGANISM: Homo sapiens

<400> SEQUENCE: 25
gtgtgctaca gttgttcaag gctt                                   24

<210> SEQ ID NO 26
<211> LENGTH: 25
<212> TYPE: DNA
<213> ORGANISM: Homo sapiens

<400> SEQUENCE: 26
ctcaatatct gccactttca ctgct                                  25

<210> SEQ ID NO 27
<211> LENGTH: 24
<212> TYPE: DNA
<213> ORGANISM: Homo sapiens

<400> SEQUENCE: 27
aggccggctt tgactgggtg tatt                                          24

<210> SEQ ID NO 28
<211> LENGTH: 20
<212> TYPE: DNA
<213> ORGANISM: Homo sapiens

<400> SEQUENCE: 28
gcggccgagt gctcggactt                                               20

<210> SEQ ID NO 29
<211> LENGTH: 24
<212> TYPE: DNA
<213> ORGANISM: Homo sapiens

<400> SEQUENCE: 29
cctgcctgtg actttcaagc tact                                          24

<210> SEQ ID NO 30
<211> LENGTH: 24
<212> TYPE: DNA
<213> ORGANISM: Homo sapiens

<400> SEQUENCE: 30
cattccaccc aaagcatgtt atct                                          24

<210> SEQ ID NO 31
<211> LENGTH: 21
<212> TYPE: DNA
<213> ORGANISM: Homo sapiens

<400> SEQUENCE: 31
ggccgcatgg atgttgctga g                                             21

<210> SEQ ID NO 32
<211> LENGTH: 22
<212> TYPE: DNA
<213> ORGANISM: Homo sapiens

<400> SEQUENCE: 32
tctgagtccc tggctggcca ga                                            22

<210> SEQ ID NO 33
<211> LENGTH: 23
<212> TYPE: DNA
<213> ORGANISM: Homo sapiens

<400> SEQUENCE: 33
ggcttgaagc tgcttacgaa ttt                                           23

<210> SEQ ID NO 34
<211> LENGTH: 25
<212> TYPE: DNA
<213> ORGANISM: Homo sapiens

<400> SEQUENCE: 34
acagcccagt acttattccc tttga                                         25

<210> SEQ ID NO 35
<211> LENGTH: 21
<212> TYPE: DNA
<213> ORGANISM: Homo sapiens

```
<400> SEQUENCE: 35
actgcggttt tctcgaatcc a                                              21

<210> SEQ ID NO 36
<211> LENGTH: 20
<212> TYPE: DNA
<213> ORGANISM: Homo sapiens

<400> SEQUENCE: 36
ggtatccatc gccatgctcc                                                20

<210> SEQ ID NO 37
<211> LENGTH: 24
<212> TYPE: DNA
<213> ORGANISM: Homo sapiens

<400> SEQUENCE: 37
agtgggaaca ggctcaggac tatc                                           24

<210> SEQ ID NO 38
<211> LENGTH: 24
<212> TYPE: DNA
<213> ORGANISM: Homo sapiens

<400> SEQUENCE: 38
ggtaggccaa agaattttg catc                                            24

<210> SEQ ID NO 39
<211> LENGTH: 19
<212> TYPE: DNA
<213> ORGANISM: Homo sapiens

<400> SEQUENCE: 39
cggcttgccc tggtgcagt                                                 19

<210> SEQ ID NO 40
<211> LENGTH: 23
<212> TYPE: DNA
<213> ORGANISM: Homo sapiens

<400> SEQUENCE: 40
cgtcccgggt gtagagtctc tcg                                            23

<210> SEQ ID NO 41
<211> LENGTH: 21
<212> TYPE: DNA
<213> ORGANISM: Homo sapiens

<400> SEQUENCE: 41
ctcgggcaaa gagggtgaca a                                              21

<210> SEQ ID NO 42
<211> LENGTH: 23
<212> TYPE: DNA
<213> ORGANISM: Homo sapiens

<400> SEQUENCE: 42
gcttcatctg tcctttccc caa                                             23

<210> SEQ ID NO 43
<211> LENGTH: 19
<212> TYPE: DNA
```

```
<213> ORGANISM: Homo sapiens

<400> SEQUENCE: 43 gagccctgg cttctggca                                                    19

<210> SEQ ID NO 44
<211> LENGTH: 21
<212> TYPE: DNA
<213> ORGANISM: Homo sapiens

<400> SEQUENCE: 44
gccctgatga cgaggtcgga a                                                21

<210> SEQ ID NO 45
<211> LENGTH: 20
<212> TYPE: DNA
<213> ORGANISM: Homo sapiens

<400> SEQUENCE: 45
ggcgacctgg aagtccaact                                                  20

<210> SEQ ID NO 46
<211> LENGTH: 19
<212> TYPE: DNA
<213> ORGANISM: Homo sapiens

<400> SEQUENCE: 46
ccatcagcac cacagcctt                                                   19
```

COMBINATION OF BIOMARKERS FOR THE DETECTION AND EVALUATION OF HEPATITIS FIBROSIS

This application is the U.S. national phase of International Application No. PCT/EP2012/052234 filed 9 Feb. 2012 which designated the U.S. and claims priority to FR 1151022 filed 9 Feb. 2011, and U.S. Provisional Application No. 61/440,986 filed 9 Feb. 2011, the entire contents of each of which are hereby incorporated by reference.

FIELD OF THE INVENTION

The application relates to hepatic fibroses, more particularly to hepatic fibroses which may be present in a subject infected with one or more hepatitis viruses. The application provides means which can be used to detect hepatic fibroses of this type. More particularly, the means of the invention are suitable for the reliable determination of the stage of hepatic tissue damage reached, in particular the hepatic fibrosis score.

BACKGROUND TO THE INVENTION

Many pathologies cause or result in liver tissue lesions, known by the name of hepatic fibrosis. Hepatic fibrosis results in particular from an excessive accumulation of molecular compounds from the altered extracellular matrix in the hepatic parenchyma.

The stage of liver tissue damage, more particularly the nature and extent of the hepatic tissue lesions, is evaluated using a hepatic fibrosis score, in particular using the Metavir F score, which comprises 5 stages, from F0 to F4 (see Table 1 below). Determining the hepatic fibrosis score is of vital importance to the clinician, since it is a prognostic score.

In fact, the clinician uses this determination to decide whether or not to administer treatment in order to treat those lesions, or at least to reduce their effects. The clinician also bases a decision to start a treatment on this determination. In particular, when the hepatic fibrosis score is at most F1, the clinician will generally decide not to administer treatment, while when the score is at least F2, the administration of treatment is recommended irrespective of the degree of necrotico-inflammatory activity.

However, anti-HCV treatments cause major side effects for the patient. As an example, the accepted current treatment for patients infected with hepatitis C virus (HCV) comprises the administration of standard or pegylated interferon over a period which may be up to 48 weeks or longer. Regarding interferon, the side effects are frequent and numerous. The most frequent side effect is that of influenza-like syndrome (fever, arthralgia, headaches, chills). Other possible side effects are: asthenia, weight loss, moderate hair loss, sleep problems, mood problems and irritability, which may have repercussions on daily life, difficulties with concentrating and skin dryness. Certain rare side effects, such as psychiatric problems, may be serious and have to be anticipated. Depression may occur in approximately 10% of cases. This has to be identified and treated, as it can have grave consequences (attempted suicide). Dysthyroidism may occur. Furthermore, treatment with interferon is counter-indicated during pregnancy.

Regarding ribavirin, the principal side effect is haemolytic anaemia. Anaemia may lead to treatment being stopped in approximately 5% of cases. Decompensation due to an underlying cardiopathy or coronaropathy linked to anaemia may arise.

Neutropenia is observed in approximately 20% of patients receiving a combination of pegylated interferon and ribavirin, and represents the major grounds for reducing the pegylated interferon dose.

The cost of these treatments is also very high.

In this context, being able to determine, in a reliable manner, the hepatic fibrosis score of a given patient, and more particularly being able to discriminate, in a reliable manner for a given patient, a hepatic fibrosis score of at most F1 from a hepatic fibrosis score of at least F2 is of crucial importance to the patient.

Currently available means for determining the hepatic fibrosis score of a patient in particular comprises anatomo-pathologic examination of a hepatic biopsy puncture (HBP). This examination can be used to make a sufficiently reliable determination of the level of fibrosis, but there are considerable risks linked to the invasive mode of sampling. In order to be sufficiently reliable for a given patient, at the very least this examination has to be carried out on a sample of sufficient quantity (removal of a length of 15 mm using a HBP needle), and has to be examined by a qualified anatomo-pathologist. HBP is an invasive, expensive procedure, and is associated with a morbidity of 0.57%. It cannot be used to monitor patients in a regular manner in order to evaluate the progress of the fibrosis.

In the prior art, there are means which have the advantage of being non-invasive, such as:
  Fibroscan™, which is a system for imaging the liver by transient elastography, and such as
  Fibrotest™, Fibrometer™ and Hepascore™, which are multivariate classification algorithms combining the measurement values for seric proteins and optionally, values for certain clinical factors,
  see WO 02/16949 A1 (in the name of Epigene), WO 2006/103570 A2 (in the name of Assistance Publique—Hopitaux de Paris), WO 2006/082522 A1 (in the name of Assistance Publique—Hopitaux de Paris), as well as their national and regional counterparts.
  Fibrotest™ (supplied by BioPredictive; Paris, France) uses measurements of alpha-2-macroglobulin (A2M), haptoglobin, apolipoprotein A1, total bilirubinaemia and gamma-glutamyl transpeptidase.
  The Fibrometer™ (supplied by BioLiveScale; Angers, France) uses assays of platelets, the prothrombin index, aspartate amino-transferase, alpha-2-macroglobulin (A2M), hyaluronic acid, and urea.
  Hepascore™ uses measurements of alpha-2-macroglobulin (A2M), hyaluronic acid, total bilirubin, gamma-glutamyl transpeptidase, and the clinical factors age and sex.
  Fibroscan™ does not have sufficient sensitivity to differentiate a F1 score from a F2 score (see for example, Castera et al. 2005, more particularly FIG. 1A of that article).

Furthermore, while it now seems to be accepted that tests such as Fibrotest™, Fibrometer™ or Hepascore™, can be used to reliably identify a hepatic cirrhosis, in particular linked to HCV, these tests do not have the capacity of precisely and reliably identifying the earlier stages of fibrosis and do not have the capacity to differentiate the F1 stage from the F2 stage of fibrosis for a given patient in a reliable manner (see for example, Shaheen et al. 2007).

Thus, there is still a need for means that can be used to determine, in a precise and reliable manner, the stage of hepatic tissue damage, more particularly the hepatic fibrosis score of a given patient. More particularly, there is still a clinical need for means that can be used to reliably distinguish, for a given patient, whether a fibrosis is absent, minimal or clinically not significant (Metavir score F0 or F1), a moderate or clinically significant fibrosis (Metavir score F2 or higher), more particularly to distinguish, in a reliable manner for a given patient, a F1 fibrosis (fibrosis without septa) from a fibrosis F2 (fibrosis with some septa). In particular, there is still a clinical need for means that can be used to detect the appearance of the first septa in a reliable manner.

The invention of the application proposes means that can in particular satisfy these needs.

SUMMARY OF THE INVENTION

The application relates to hepatic fibroses, in particular to hepatic fibroses which may be present in a subject who is or has been infected with one or more hepatitis viruses, in particular hepatitis C virus (HCV), hepatitis B virus (HBV) or hepatitis D virus (HDV).

The inventors have identified genes the levels of expression of which are biomarkers of a stage of tissue damage, more particularly the hepatic fibrosis score. More particularly, the inventors propose establishing the expression profile of these genes and using this profile as a signature of the stage of tissue damage, more particularly the hepatic fibrosis score.

The application provides means which are specially adapted for this purpose. The means of the invention in particular use the measurement or assay of the expression levels of selected genes, said selected genes being:
SPP1, and
at least one gene from among A2M and VIM, and
at least one gene from among IL8, CXCL10 and ENG, and
optionally, at least one gene from among the list of the following sixteen genes: IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1.

In particular, the means of the invention comprise:
methods which comprise the measurement or assay of the levels of expression of selected genes;
products or reagents which are specially adapted to the measurement or assay of these levels of gene expression;
manufactured articles, compositions, pharmaceutical compositions, kits, tubes or solid supports comprising such products or reagents, as well as
computer systems (in particular a computer program product and computer device) which are specially adapted to implementing the means of the invention.

DETAILED DESCRIPTION OF THE INVENTION

Figure 1:
FIG. 1: process for classifying a patient p from clinical and biological data ($x_p$) which are predictive of a clinical status $y_p$.

The application pertains to the subject matter defined in the claims as filed, to the subject matter described below and to the subject matter illustrated in the "Examples" section.

In the application, unless otherwise specified, or unless the context indicates otherwise, all of the terms used have their usual sense in the domain(s) concerned.

The application pertains to means for detecting or for diagnosis of liver tissue damage, in particular a hepatic fibrosis. In particular, the means of the invention are suitable for the determination of the stage of tissue damage, more particularly to determination of the hepatic fibrosis score.

More particularly, the means of the invention are suitable for hepatic fibroses which may be present in a subject who is or has been infected with one or more hepatitis viruses, in particular such as hepatitis C virus (HCV) and/or hepatitis B virus (HBV) and/or hepatitis D virus (HDV), more particularly with at least HCV (and, optionally, with HBV and/or HDV).

Fibrosis is the fibrous transformation of certain tissues, which is the source of an increase in conjunctive tissue (support and filling tissue). In general, fibrosis occurs as a consequence of chronic inflammation.

The term "hepatic fibrosis score" reflects the degree of progress of the hepatic fibrosis. The hepatic fibrosis score quantifies the liver tissue damage, in particular the nature, number and intensity of the fibrous lesions in the liver.

Thus, the means of the invention are means which can be used to detect, quantify or at the very least evaluate the liver tissue damage of a subject.

In the field of hepatic fibroses, various score systems have been set up and are known to the skilled person, for example the Metavir score (in particular the Metavir F score) or the Ishak score (see Goodman 2007).

TABLE 1

Correspondence between Metavir fibrosis scores and Ishak fibrosis scores

| | Fibrosis score | |
|---|---|---|
| Stage of fibrosis | Metavir | Ishak |
| Absence of fibrosis | F0 | F0 |
| Portal fibrosis without septa | F1 | F1/F2 |
| Portal fibrosis and some septa | F2 | F3 |
| Septal fibrosis without cirrhosis | F3 | F4 |
| Cirrhosis | F4 | F5/F6 |

Unless otherwise indicated, or unless the context dictates otherwise, the hepatic fibrosis scores indicated in the application are F scores established in accordance with the Metavir system, and the terms "score", "fibrotic score", "fibrosis score", "hepatic fibrosis score" and similar terms have the clinical significance of a Metavir F score, i.e. they qualify or even quantify the damage to the tissue, more particularly the lesions (or fibrosis) of a liver.

In the application, the expression "at most F1" includes a score of F1 or F0, more particularly a score of F1, and the expression "at least F2" includes a score of F2, F3 or F4.

Advantageously, the means of the invention can be used to reliably distinguish:
- a hepatic fibrosis the fibrotic score of which, using the Metavir system, is at most F1 (absence of fibrosis or portal fibrosis without septa),
- from a hepatic fibrosis the fibrotic score of which, using the Metavir system, is at least F2 (portal fibrosis with some septa, septal fibrosis without cirrhosis, or cirrhosis).

More particularly, the means of the invention can be used to reliably distinguish:
- a hepatic fibrosis the fibrotic score of which, using the Metavir system, is F1 (portal fibrosis without septa),
- from a hepatic fibrosis the fibrotic score of which, using the Metavir system, is F2 (portal fibrosis with some septa).

From a clinical view point, the means of the invention can be used to reliably determine whether the hepatic fibrosis has no septa or whether that fibrosis already includes septa.

The distinction which can be made by the means of the invention is clinically very useful.

In fact, when the hepatic fibrosis is absent or is not at a stage where the septa have not yet appeared (Metavir score F0 or F1), the clinician may elect not to administer treatment to the patient, judging, for example, that at this stage of the hepatic fibrosis, the risk/benefit ratio of the drug treatment which could be administered to the patient would not be favourable while, when the hepatic fibrosis has reached the septal stage (Metavir score F2, F3 or F4), the clinician will recommend the administration of a drug treatment to block or at least slow down the progress of this hepatic fibrosis, in order to reduce the risk of developing into cirrhosis.

By being able to make these distinctions in a reliable manner, the means of the invention can be used to administer, in good time, the drug treatments which are currently available to attempt to combat or at least alleviate a hepatic fibrosis. Since these drug treatments usually give rise to major side effects for the patient, the means of the invention provide very clear advantages as regards the general health of the patient. This is the case, for example, when this treatment comprises the administration of standard or pegylated interferon either as a monotherapy (for example in the case of chronic viral hepatitis B and D), or in association with ribavirin (for example in the case of chronic hepatitis C).

This is also the case when the treatment has to be administered long-term, as is the case for nucleoside and nucleotide analogues in the treatment of chronic hepatitis B.

In particular, the means of the invention comprise:
- methods which include measuring or assaying the levels of expression of selected genes (level of transcription or translation);
- products or reagents which are specifically adapted to measuring or assaying these levels of expression of the genes;
  - manufactured articles, compositions, pharmaceutical compositions, kits, tubes or solid supports comprising such products or reagents; as well as
  - computer systems (in particular, a computer program product and computer device) which are specially adapted to implementing the means of the invention.

In accordance with one aspect of the invention, a method of the invention is a method for detecting or diagnosing a hepatic fibrosis in a subject, in particular a method for determining the hepatic fibrosis score of that subject.

More particularly, the means of the invention are suitable for subjects who are or have been infected with one or more hepatitis viruses, such as with hepatitis C virus (HCV) and/or hepatitis B virus (HBV) and/or hepatitis D virus (HDV) in particular, especially with at least HCV.

Advantageously, a method of the invention may be a method for determining whether the fibrotic score of a hepatic fibrosis is at most F1 (score of F1 or F0, more particularly F1) or at least F2 (score of F2, F3 or F4), more particularly whether this score is F1 or F2 (scores expressed using the Metavir system).

As indicated above, it is preferable to administer a treatment only to patients with a Metavir fibrotic score of more than F1. For the other patients, simple monitoring is preferable in the medium term (several months to a few years).

Consequently, the method of the invention may be considered to be a treatment method, more particularly a method for determining the time when a treatment should be administered to a subject. Said treatment may in particular be a treatment aimed at blocking or slowing down the progress of hepatic fibrosis, by eliminating the virus (in particular in the case of hepatitis C) and/or by blocking the virus (in particular in the case of hepatitis B).

In fact, the means of the invention can be used to determine, in a reliable manner, the degree of tissue damage of the liver of the subject, more particularly of determining the nature of those lesions (fibrosis absent or without septa versus septal fibrosis). Thus, the invention proposes a method comprising the fact of:
- determining the hepatic fibrosis score of a subject using the means of the invention; and
- whether the score determined thereby is a fibrotic score of at least F2 (using the Metavir score system), administering to that subject a treatment aimed at blocking or slowing down the progress of the hepatic fibrosis (such as standard or pegylated interferon, as a monotherapy, a polytherapy, for example in association with ribavirin).

If the score which is determined is at most F1 (score expressed using the Metavir score system), the clinician may elect not to administer that treatment.

One feature of a method of the invention is that it includes the fact of measuring (or assaying) the level to which the selected genes are expressed in the organism of said subject.

The expression "level of expression of a gene" or equivalent expression as used here designates both the level to which this gene is transcribed into RNA, more particularly into mRNA, and also the level to which a protein encoded by that gene is expressed.

The term "measure" or "assay" or equivalent term is to be construed as being in accordance with its general use in the field, and refers to quantification.

The level of transcription (RNA) of each of said genes or the level of translation (protein) of each of said genes, or indeed the level of transcription for certain of said selected genes and the level of translation for the others of these selected genes can be measured. In accordance with one embodiment of the invention, either the level of transcription or the level of translation of each of said selected genes is measured.

The fact of measuring (or assaying) the level of transcription of a gene includes the fact of quantifying the RNAs transcribed from that gene, more particularly of determining the concentration of RNA transcribed by that gene (for example the quantity of those RNAs with respect to the total quantity of RNA initially present in the sample, such as a value for Ct normalized by the $2^{-\Delta Ct}$ method; see below).

The fact of measuring (or assaying) the level of translation of a gene includes the fact of quantifying proteins encoded by that gene, more particularly of determining the concentration of proteins encoded by this gene, (for example the quantity of that protein per volume of biological fluid).

Certain proteins encoded by a mammalian gene, in particular a human gene, may occasionally be subjected to post-translation modifications such as, for example, cleavage into polypeptides and/or peptides. If appropriate, the fact of measuring (or assaying) the level of translation of a gene may then comprise the fact of quantifying or determining the concentration, not of the protein or proteins themselves, but of one or more post-translational forms of this or these proteins, such as, for example, polypeptides and/or peptides which are specific fragments of this or these proteins.

In order to measure or assay the level of expression of a gene, it is thus possible to quantify:
the RNA transcripts of that gene, or
proteins expressed by this gene or post-translational forms of such proteins, such as polypeptides or peptides which are specific fragments of these proteins, for example.

In accordance with the invention, the selected genes are:
SPP1, and
at least one gene from among A2M and VIM, and
at least one gene from among IL8, CXCL10 and ENG, and
optionally, at least one gene from among the list of the following sixteen genes: IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1.

The genes selected in this manner constitute a combination of genes in accordance with the invention.

Examples of combinations of genes in accordance with the invention are presented in Table 3 below.

Each of these genes is individually known to the skilled person and should be understood to have the meaning given to it in this field. An indicative reminder of their respective identities is presented in Table 2 below.

None of these genes is a gene of the hepatitis virus. They are mammalian genes, more particularly human genes.

Each of these genes codes for a non-membrane protein, i.e. a protein which is not anchored in a cell membrane. The in vivo localization of these proteins is thus intracellular and/or extracellular. These proteins are present in a biological fluid of the subject, such as in the blood, serum, plasma or urine, for example, in particular in the blood or the serum or the plasma.

In addition to the levels of expression of genes selected from the list of the twenty-two genes of the invention (SPP1, A2M, VIM, IL8, CXCL10, ENG, IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1), a method in accordance with the invention may further comprise the measurement of factors other than the level of expression of said selected genes, such as measuring intracorporal metabolites (for example, cholesterol), and/or measuring elements occurring in the blood (for example platelets), and/or measuring the quantity of iron which is circulating, and/or measuring the level of expression of other mammalian genes (more particularly human genes), for example to measure the level of transcription of genes which are listed below as "other biological factors", such as the gene coding for alanine-amino-transferase (assay of the concentration of ALT). However, these measurements are optional.

In a method in accordance with the application, the number of mammalian genes (more particularly human genes) the level of expression of which is measured and which are not genes selected from said list of twenty-two genes of the invention (for example ALT), is preferably a maximum of 18, more particularly 14 or fewer, more particularly 11 or fewer, more particularly 6 or fewer, more particularly 4 or 3 or 2, more particularly 1 or 0.

It follows that counting these "other" mammalian genes (more particularly these human genes) the level of expression of which may optionally be assayed, as well as the maximum number of the twenty-two genes which may be the genes selected from said list of twenty-two genes of the invention, the total number of genes the level of expression of which is measured in a method in accordance with the application is preferably 3 to 40 genes, more particularly 3 to 36, more particularly 3 to 33, more particularly 3 to 28, more particularly 3 to 26, more particularly 3 to 25, more particularly 3 to 24, more particularly 3 to 23, more particularly 3 to 22, more particularly 3 to 20, more particularly 3 to 21, more particularly 3 to 20, more particularly 3 to 19, more particularly 3 to 18, more particularly 3 to 17, more particularly 3 to 16, more particularly 3 to 15, more particularly 3 to 14, more particularly 3 to 13, more particularly 3 to 12, more particularly 3 to 11, more particularly 3 to 10, more particularly 3 to 9, more particularly 3 to 8, more particularly 3 to 7, more particularly 3 to 6, more particularly 3 to 5, for example 3, 4 or 5, in particular 4 or 5.

Further, as will be presented in more detail below, and as illustrated in the examples, the number of genes selected from said list of twenty-two genes of the invention may advantageously be less than 22: this number may more particularly be 3 to 10, more particularly 3 to 9, more particularly 3 to 8, more particularly 3 to 7, more particularly 3 to 6, more particularly 3 to 5, for example 3, 4 or 5, in particular 4 or 5.

The method of the invention may optionally comprise measuring the expression product of one or more non-human genes, more particularly viral genes, such as genes of the hepatitis virus (more particularly HCV and/or HBV and/or HDV).

The method of the invention may optionally comprise determining the genotype or genotypes of the hepatitis virus or viruses with which the subject is infected.

The method of the invention may optionally comprise determining one or more clinical factors of said subject, such as the insulin sensitivity index.

TABLE 2

| Symbol | Name (in French) of coded protein | Name (in English) of coded protein | Alias | NM, accession number |
|---|---|---|---|---|
| SPP1 | phosphoprotéine 1 sécrétée | secreted phosphoprotein 1 | OPN; BNSP; BSPI; ETA-1; MGC110940 | NM_000582 |
| A2M | alpha 2 macroglobuline | alpha-2-macroglobulin | CPAMD5; FWP007; S863-7; DKFZp779B086 | NM_000014 |
| VIM | vimentine | vimentin | FLJ36606 | NM_003380 |
| IL8 | interleukine 8 | interleukin-8 | IL-8; CXCL8; GCP-1; GCP1; LECT; LUCT; LYNAP; MDNCF; MONAP; NAF; NAP-1; NAP1 | NM_000584 |
| CXCL10 | ligand 10 à chémokine (motif CXC) | C—X—C motif chemokine 10 | C7; IFI10; INP10; IP-10; SCYB10; crg-2; gIP-10; mob-1 | NM_001565 |
| ENG | endogline | endoglin | CD105; ORW | NM_000118 |
| IL6ST | transducteur de signal interleukin-6 | interleukin-6 signal transducer | CD130; GP130; CDw130; IL6R-beta; GP130-RAPS | NM_002184 |
| p14ARF transcrit No. 4 du gene CDKN2A | inhibiteur de kinase 2A cycline dépendent | cyclin-dependent kinase 2A inhibitor | CDKN2A (coding for p14 and p16); CDKN2; MLM; ARF; p14; p16; p19; CMM2; INK4; MTS1; TP16; CD4I; INK4a; p16INK4; p16INK4a | NM_058195 |
| MMP9 | métallopeptidase 9 de matrice | matrix metallopeptidase 9 | CLG4B; GELB; MANDP2 | NM_004994 |
| ANGPT2 | angiopoïétine 2 | angiopoietin-2 | ANG2; AGPT2 | NM_001147 |
| CXCL11 | ligand 11 à chémokine (motif CXC) | C—X—C motif chemokine 11 | IP9; SCYB11; ITAC; SCYB9B; H174; IP-9; b-R1; I-TAC; MGC102770 | NM_005409 |
| MMP2 | métallopeptidase 2 de matrice | matrix metallopeptidase 2 | CLG4; MONA; TBE1; CLG4A; MMPII | NM_004530 |
| MMP7 | métalloprotéinase 7 de matrice | matrix metallopeptidase 7 | MPSL1; PUMP1; MMP-7; PUMP-1 | NM_002423 |
| S100A4 | protéine A4 liant le calcium S100 | protein S100-A4 | FSP1 | NM_019554 |
| TIMP1 | inhibiteur 1 de métalloprotéinase | metalloproteinase inhibitor 1 | RP1-230G1.3; CLGI; EPA; EPO; FLJ90373; HCI; TIMP | NM_003254 |
| CHI3L1 | protéine 1 de type chitinase-3 | chitinase-3-like protein | GP39; ASRT7; YKL40; YYL-40; HC-gp39; HCGP-3P; FLJ38139; DKFZp686N19119 | NM_001276 |
| COL1A1 | chaîne alpha-1(I) du collagène | collagen alpha-1(I) chain | OI4 | NM_000088 |
| CXCL1 | chimiokine 1 de la protéine alpha régulant la croissance (motif CXC) | growth-regulated alpha protein C—X—C motif chemokine 1 | GRO; GRO1; GROA; MGSA; SCYB1FS; NAP-3; SCYB1; MGSA-a | NM_001511 |
| CXCL6 | ligand 6 à chémokine (motif CXC) | C—X—C motif chemokine 6 | CKA-3; GCP-2; GCP2; SCYB6 | NM_002993 |
| IHH | protéine "Indian Hedgehog" | Indian hedgehog protein | BDA1; HHG2 | NM_002181 |
| IRF9 | facteur de transcription 3G stimulé par interféron | interferon regulatory factor 9 | ISGF3G; p48; ISGF3 | NM_006084 |
| MMP1 | métalloprotéinase 1 de matrice | matrix metalloproteinase-1 | CLG; CLGN | NM_002421 |

Measuring (or assaying) the level of expression of said selected genes may be carried out in a sample which has been obtained from said subject, such as:
- a biological sample removed from or collected from said subject, or
- a sample comprising nucleic acids (in particular RNAs) and/or proteins and/or polypeptides and/or peptides of said biological sample, in particular a sample comprising nucleic acids and/or proteins and/or polypeptides and/or peptides which have been or are susceptible of having been extracted and/or purified from said biological sample, or
- a sample comprising cDNAs which have been or are susceptible of having been obtained by reverse transcription of said RNAs.

A biological sample collected or removed from said subject may, for example, be a sample removed or collected or susceptible of being removed or collected from:
- an internal organ or tissue of said subject, in particular from the liver or its hepatic parenchyma, or
- a biological fluid from said subject such as the blood, serum, plasma or urine, in particular an intracorporal fluid such as blood.

A biological sample collected or removed from said subject may, for example, be a sample comprising a portion of tissue from said subject, in particular a portion of hepatic tissue, more particular a portion of the hepatic parenchyma.

A biological sample collected or removed from said subject may, for example, be a sample comprising cells which have been or are susceptible of being removed or collected from a tissue of said subject, in particular from a hepatic tissue, more particularly hepatic cells.

A biological sample collected or removed from said subject may, for example, be a sample of biological fluid such as a sample of blood, serum, plasma or urine, more particularly a sample of intracorporal fluid such as a sample of blood or serum or plasma. In fact, since the genes selected from said list of twenty-two genes of the invention all code for non-membrane proteins, the product of their expression may in particular have an extracellular localization.

Said biological sample may be removed or collected by inserting a sampling instrument, in particular by inserting a needle or a catheter, into the body of said subject. This instrument may, for example be inserted:
- into an internal organ or tissue of said subject, in particular into the liver or into the hepatic parenchyma, for example:
  - to remove a sample of liver or hepatic parenchyma, said removal possibly, for example, being carried out by hepatic biopsy puncture (HBP), more particularly by transjugular or transparietal HBP, or to remove or collect cells from the hepatic compartment (removal of cells and not of tissue), more particularly from the hepatic parenchyma, in particular to remove hepatic cells, this removal or collection possibly being carried out by hepatic cytopuncture; and/or into a vein, an artery or a vessel of said subject in order to remove a biological fluid from said subject, such as blood.

The means of the invention are not limited to being deployed on a tissue biopsy, in particular hepatic tissue. They may be deployed on a sample obtained or susceptible of being obtained by taking a sample with a size or volume which is substantially smaller than a tissue sample, namely a sample which is limited to a few cells. In particular, the means of the invention can be deployed on a sample obtained or susceptible of being obtained by hepatic cytopuncture.

The quantity or the volume of material removed by hepatic cytopuncture is much smaller than that removed by HBP. In addition to the immediate gain for the patient in terms of reducing the invasive nature of the technique and reducing the associated morbidity, hepatic cytopuncture has the advantage of being able to be repeated at distinct times for the same patient (for example to determine the change in the hepatic fibrosis between two time periods), while HBP cannot reasonably be repeated on the same patient. Thus, in contrast to HBP, hepatic cytopuncture has the advantage of allowing clinical changes in the patient to be monitored.

Thus, in accordance with the invention, said biological sample may advantageously be:
  cells removed or collected from the hepatic compartment (removal or collection of cells and not of tissue), more particularly from the hepatic parenchyma, i.e. a biological sample obtained or susceptible of being obtained by hepatic cytopuncture;
and/or
  biological fluid removed or collected from said subject, such as blood or urine, in particular blood.

The measurement (or assay) may be carried out in a biological sample which has been collected or removed from said subject and which has been transformed, for example:
  by extraction and/or purification of nucleic acids, in particular RNAs, more particularly mRNAs, and/or by reverse transcription of said RNAs, in particular of said mRNAs, or
  by extraction and/or purification of proteins and/or polypeptides and/or peptides, or by extraction and/or purification of a protein fraction such as serum or plasma extracted from blood.

As an example, when the collected or removed biological sample is a biological fluid such as blood or urine, before carrying out the measurement or the assay, said sample may be transformed:
  by extraction of nucleic acids, in particular RNA, more particularly mRNA, and/or by reverse transcription of said RNAs, in particular of said mRNAs (most generally by extraction of RNAs and reverse transcription of said RNAs), or
  by separation and/or extraction of the seric fraction or by extraction or purification of seric proteins and/or polypeptides and/or peptides.

Thus, in one embodiment of the invention, said sample obtained from said subject comprises (for example in a solution), or is, a sample of biological fluid from said subject, such as a sample of blood, serum, plasma or urine, and/or is a sample which comprises (for example in a solution):
  RNAs, in particular mRNAs, which are susceptible of having been extracted or purified from a biological fluid such as blood or urine, in particular blood; and/or
  cDNAs which are susceptible of having been obtained by reverse transcription of said RNAs; and/or
  proteins and/or polypeptides and/or peptides which are susceptible of having been extracted or purified from a biological fluid, such as blood or urine, in particular blood, and/or susceptible of having been encoded by said RNAs,
preferably
  proteins and/or polypeptides and/or peptides which are susceptible of having been extracted or purified from a biological fluid, such as blood or urine, in particular blood, and/or susceptible of having been encoded by said RNAs.

When said sample obtained from said subject comprises a biological sample obtained or susceptible of being obtained by sampling a biological fluid such as blood or urine, or when said sample obtained from said subject is obtained or susceptible of having been obtained from said biological sample by extraction and/or purification of molecules contained in said biological sample, the measurement is preferably a measurement of proteins and/or polypeptides and/or peptides, rather than measuring nucleic acids.

When the biological sample which has been collected or removed is a sample comprising a portion of tissue, in particular a portion of hepatic tissue, more particularly a portion of the hepatic parenchyma such as, for example, a biological sample removed or susceptible of being removed by hepatic biopsy puncture (HBP), or when the biological sample collected or removed is a sample comprising cells obtained or susceptible of being obtained from such a tissue, such as a sample collected or susceptible of being collected by hepatic cytopuncture, for example, said biological sample may be transformed:
  by extraction of nucleic acids, in particular RNA, more particularly mRNA, and/or by reverse transcription of said RNAs, in particular said mRNAs (most generally by extraction of said RNAs and reverse transcription of said RNAs), or
  by separation and/or extraction of proteins and/or polypeptides and/or peptides.

A step for lysis of the cells, in particular lysis of the hepatic cells contained in said biological sample, may be carried out in advance in order to render nucleic acids or, if appropriate, proteins and/or polypeptides and/or peptides, directly accessible to the analysis.

Thus, in one embodiment of the invention, said sample obtained from said subject is a sample of tissue from said subject, in particular hepatic tissue, more particularly hepatic parenchyma, or is a sample of cells of said tissue and/or is a sample which comprises (for example in a solution):
  hepatic cells, more particularly cells of the hepatic parenchyma, for example cells obtained or susceptible of being obtained by dissociation of cells from a biopsy of hepatic tissue or by hepatic cytopuncture; and/or
  RNAs, in particular mRNAs, which are susceptible of having been extracted or purified from said cells; and/or
  cDNAs which are susceptible of having been obtained by reverse transcription of said RNAs; and/or proteins and/or polypeptides and/or peptides which are susceptible of having been extracted or purified from said cells and/or susceptible of having been coded for by said RNAs.

In accordance with the invention, said subject is a human being or a non-human animal, in particular a human being or a non-human mammal, more particularly a human being.

Because of the particular selection of genes proposed by the invention, the hepatic fibrosis score of said subject may be deduced or determined from measurement or assay values obtained for said subject, in particular by statistical inference and/or statistical classification (see FIG. 1), for example with respect to (pre)-established reference cohorts in accordance with their hepatic fibrosis score.

In addition to measuring (or assaying) the level to which the selected genes are expressed in the organism of said subject, a method of the invention may thus further comprise a step for deducing or determining the hepatic fibrosis score of said subject from values for measurements obtained for said subject. This step for deduction or determination is a step in which the values for the measurements or assays obtained for said subject are analysed in order to infer therefrom the hepatic fibrosis score of said subject.

The hepatic fibrosis score of said subject may be deduced or determined by comparing the values for measurements obtained from said subject with their values, or the distribution of their values, in reference cohorts which have already been set up as a function of their hepatic fibrosis score, in order to classify said subject into that of those reference cohorts to which it has the highest probability of belonging (i.e. to attribute a hepatic fibrosis score to said subject).

The measurements made on said subject and on the individuals of the reference cohorts or sub-populations are measurements of the levels of gene expression (transcription or translation).

In order to measure the level of transcription of a gene, its level of RNA transcription is measured. Such a measurement may, for example, comprise assaying the concentration of transcribed RNA of each of said selected genes, either by assaying the concentration of these RNAs or by assaying the concentration of cDNAs obtained by reverse transcription of these RNAs. The measurement of nucleic acids is well known to the skilled person. As an example, the measurement of RNA or corresponding cDNAs may be carried out by amplifying nucleic acid, in particular by PCR. Some reagents are described below for this purpose (see Example 1 below). Examples of appropriate primers and probes are also given (see, for example, Table 17 below). The conditions for amplification of the nucleic acids may be selected by the skilled person. Examples of amplification conditions are given in the "Examples" section which follows (see Example 1 below).

In order to measure the level of translation of a gene, its level of protein translation is measured. Such a measurement may, for example, comprise assaying the concentration of proteins translated from each of said selected genes (for example, measuring the proteins in the general circulation, in particular in the serum). Protein measurement is well known to the skilled person. As an example, the proteins (and/or polypeptides and/or peptides) may be measured by ELISA or any other immunometric method which is known to the skilled person, or by a method using mass spectrometry which is known to the skilled person.

Preferably, each measurement is carried out in duplicate at least.

The measurement values are values of concentration or proportion, or values which represent a concentration or a proportion. The aim is that within a given combination, the measurement values of the levels of expression of each of said selected genes reflect as accurately as possible, at least with respect to each other, the degree to which each of these genes is expressed (degree of transcription or degree of translation), in particular by being proportional to these respective degrees.

As an example, in the case of measurement of the level of expression of a gene by measurement of transcribed RNAs, i.e. in the case of measurement of the level of transcription of this gene, the measurement is generally carried out by amplification of the RNAs by reverse transcription and PCR (RT-PCR) and by measuring values for Ct (cycle threshold).

A value for Ct provides a measure of the initial quantity of amplified RNAs (the smaller the value for Ct, the larger the quantity of these nucleic acids). The Ct values measured for a target RNA ($Ct_{target}$) are generally related to the total quantity of RNA initially present in the sample, for example by deducing, from this $Ct_{target}$, the value for a reference Ct ($Ct_{reference}$), such as the value of Ct which was measured under the same operating conditions for the RNA of an endogenous control gene for which the level of expression is stable (for example, a gene involved in a cellular metabolic cascade, such as RPLP0 or TBP; see Example 1 below).

In one embodiment of the invention, the difference ($Ct_{target}-Ct_{reference}$), or $\Delta Ct$, may also be exploited by the method known as the $2^{-\Delta Ct}$ method (Livak and Schmittgen 2001; Schmittgen and Livak 2008), with the form:

$$2^{-\Delta Ct} = 2^{-(Ct\ target - Ct\ reference)}$$

Hence, in one embodiment of the invention, the levels to which each of said selected genes is transcribed are measured as follows:

by amplification, of a fragment of the RNAs transcribed by each of said selected genes, for example by reverse transcription and PCR of these RNA fragments in order to obtain the Ct values for each of these RNAs, optionally, by normalisation of each of these Ct values with respect to the value for Ct obtained for the RNA of an endogenous control gene, such as RPLP0 or TBP, for example by the $2^{-\Delta Ct}$ method, optionally, by Box-Cox transformation of said normalized values for Ct.

In the case of measuring the level of expression of a gene by measuring proteins expressed by that gene, i.e. in the case of measuring a level of translation of that gene, the measurement is generally carried out by an immunometric method using specific antibodies, and by expression of the measurements made thereby in quantities by weight or international units using a standard curve. Examples of specific antibodies are indicated in Table 14 below. A value for the measurement of the level of translation of a gene may, for example, be expressed as the quantity of this protein per volume of biological fluid, for example per volume of serum (in mg/mL or in µg/mL or in ng/mL or in pg/mL, for example).

If desired or required, the distribution of the measurement values obtained for the individuals of a cohort may be smoothed so that it approaches a Gaussian law.

To this end, the measurement values obtained for individuals of that cohort, for example the values obtained by the $2^{-\Delta t}$ method, may be transformed by a transformation of the Box-Cox type (Box and Cox, 1964; see Tables 8, 9, 11 and 13 below; see Examples 2 and 3 below).

Thus, the application relates to an in vitro method for determining the hepatic fibrosis score of a subject, more particularly of a subject infected with one or more hepatitis viruses, such as with HCV and/or HBV and/or HDV, in particular with at least HCV, characterized in that it comprises the following steps:

i) in a sample which has been obtained from said subject, measuring the level to which the selected genes are transcribed or translated, said selected genes being:
   SPP1, and
   at least one gene from among A2M and VIM, and
   at least one gene from among IL8, CXCL10 and ENG, and
   optionally, at least one gene from among the list of the following sixteen genes: IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1,
and
ii) comparing the measurement values of each of said selected genes obtained for said subject with their values, or the distribution of their values, in reference cohorts which have been pre-established as a function of their hepatic fibrosis score, in order to classify said subject into that of those reference cohorts with respect to which it has the highest probability of belonging.

The comparison of step ii) may in particular be made by combining the measurement (or assay) values obtained for said subject in a multivariate classification model.

Such a multivariate classification model compares (in a combined manner) measurement values obtained for said subject with their values, or with the distribution of their values, in reference cohorts which have been pre-established as a function of their hepatic fibrosis score, in order to classify said subject into that of those reference cohorts with respect to which it has the strongest probability of belonging, for example by attributing to it an output value which indicates the hepatic fibrosis score of said subject.

Such a multivariate classification model may be constructed, in particular constructed in advance, by making an inter-cohort comparison of the values of measurements obtained for said reference cohorts or of distributions of those measurement values.

More particularly, such a multivariate classification model may be constructed, in particular constructed in advance, by measuring or assaying the levels of expression of said genes selected from reference cohorts pre-established as a function of their hepatic fibrosis score, and by analysing these measurement values or their distribution using a multivariate statistical method in order to construct a multivariate classification model which infers or determines a hepatic fibrosis score from the values for the levels of expression of said selected genes.

If in addition to values for the measurement of the levels of transcription or translation of said selected genes, the values measured for said subject comprise the value or values for one or more other factors, such as one or more virological factors and/or one or more clinical factors and/or one or more other biological factors (see below and in the examples), the classification model is of course constructed, in particular constructed in advance, by measuring or assaying the same values in reference cohorts which have been pre-established as a function of their hepatic fibrosis score, and by analysing these values or their distribution by means of a multivariate statistical method in order to construct a multivariate classification model which infers or determines a hepatic fibrosis score from these values.

As an example, a model may be constructed by a mathematical function, a non-parametric technique, a heuristic classification procedure or a probabilistic predictive approach. A typical example of classification based on the quantification of the level of expression of biomarkers consists of distinguishing between "healthy" and "sick" subjects. The formalization of this problem consists of m independent samples, described by n random variables. Each individual i (i=1, . . . , m) is characterized by a vector $x_i$ describing the n characteristic values:

$$x_{ij}, i=1, \ldots m\; j=1, \ldots n$$

These characteristic values may, for example, represent gene expression values and/or the intensities of protein data and/or the intensities of metabolic data and/or clinical data.

Each sample $x_i$ is associated with a discreet value $y_i$, representing the clinical status of the individual i. By way of example, $y_i=0$ if the patient i has a hepatic fibrosis score of F1, $y_i=1$ if the patient i has a hepatic fibrosis score of F2.

A model offers a decision rule (for example a mathematical function, an algorithm or a procedure) which uses the information available from $x_i$ to predict $y_j$ in each sample observed. The aim is to use this model in order to predict the clinical status of a patient p, namely $y_p$, from available biological and/or clinical values, namely $x_p$.

A process for the classification of a patient p is shown diagrammatically in FIG. 1.

A variety of multivariate classification models is known to the skilled person (see Hastie, Tibishirani and Friedman, 2009; Falissard, 2005; Theodoridis and Koutroumbos 2009).

They are generally constructed by processing and interpreting data by means, for example, of:
   a multivariate statistical analysis method, for example:
      a linear or non-linear mathematical function, in particular a linear mathematical function such as a function generated by the mROC method (multivariate ROC method), or
      a ROC (Receiver Operating Characteristics) method;
      a linear or non-linear regression method, such as the logistical regression method, for example;
      a PLS-DA (Partial Least Squares-Discriminant Analysis) method;
      a LDA (Linear Discriminant Analysis) method;
   a machine learning or artificial intelligence method, for example a machine learning or artificial intelligence algorithm, a non-parametric, or heuristic, classification method or a probabilistic predictive method such as:
      a decision tree; or
      a boosting type method based on binary classifiers (example: Adaboost) or a method linked to boosting (bagging); or
      a k-nearest neighbours (or KNN) method, or more generally the weighted k-nearest neighbours method (or WKNN), or
      a Support Vector Machine (or SVM) method (for example an algorithm); or
      a Random Forest (or RF); or
      a Bayesian network; or
      a Neural Network; or
      a Galois lattice or Formal Concept Analysis.

The decision rules for the multivariate classification models may, for example, be based on a mathematical formula of the type $y=f(x_1, x_2, \ldots x_n)$ where f is a linear or non-linear mathematical function (logistic regression, mROC, for example), or on a machine learning or artificial intelligence algorithm the characteristics of which consist of a series of control parameters identified as being the most effective for the discrimination of subjects (for example, KNN, WKNN, SVM, RF).

The multivariate ROC method (mROC) is a generalisation of the ROC (Receiver Operating Characteristic) method (see Reiser and Faraggi 1997; Su and Liu 1993, Shapiro, 1999). It calculates the area under the ROC curve (AUC) relative to a linear combination of biomarkers and/or biomarker transformations (in the case of normalization), assuming a multivariate normal distribution. The mROC method has been described in particular by Kramar et al. 1999 and Kramar et al. 2001. Reference is also made to the examples below, in particular point 2 of Example 1 below (mROC model).

The mROC version 1.0 software, commercially available from the designers (A. Kramar, A. Fortune, D. Farragi and B. Reiser) may, for example, be used to construct a mROC model.

Andrew Kramar and Antoine Fortune can be contacted at or via the Unité de Biostatistique du Centre Régional de Lutte contre le Cancer (CRLC) [Biostatistics Unit, Regional Cancer Fighting Centre], Val d'Aurelle—Paul Lamarque (208, rue des Apothicaires; Parc Euromédecine; 34298 Montpellier Cedex 5; France).

David Faraggi and Benjamin Reiser can be contacted at or via the Department of Statistics, University of Haifa (Mount Carmel; Haifa 31905; Israel).

The family of artificial intelligence or machine learning methods is a family of algorithms which, instead of proceeding to an explicit generalization, compares the examples of a new problem with examples considered to be training examples and which have been stored in the memory. These algorithms directly construct hypotheses from the training examples themselves. A simple example of this type of algorithm is the k-nearest neighbours (or KNN) model and one of its possible extensions, known as the weighted k nearest neighbours (or WKNN) algorithm (Hechenbichler and Schliep, 2004).

In the context of the classification of a new observation x, the simple basic idea is to make the nearest neighbours of this observation count. The class (or clinical status) of x is determined as a function of the major class from among the k nearest neighbours of the observation x.

Libraries of specific KKNN functions are available, for example, from R software (http://www.R-project.org/). R software was initially developed by John Chambers and Bell Laboratories (see Chambers 2008). The current version of this software suite is version 2.11.1. The source code is freely available under the terms of the "Free Software Foundation's GNU" public licence at the website http://www.R-project.org/. This software may be used to construct a WKNN model.

Reference is also made to the examples below, in particular to point 2 of Example 1 below (WKNN model).

A Random Forest (or RF) model is constituted by a set of simple tree predictors each being susceptible of producing a response when it is presented with a sub-set of predictors (Breiman 2001; Liaw and Wiener 2002). The calculations are made with R software. This software may be used to construct RF models.

Reference is also made to the examples below, in particular to point 2 of Example 1 below (RF model).

A neural network is constituted by an orientated weighted graph the nodes of which symbolize neurons. The network is constructed from examples of each class (for example F2 versus F1) and is then used to determine to which class a new element belongs; see Intrator and Intrator 1993, Riedmiller and Braun 1993, Riedmiller 1994, Anastasiadis et al. 2005; see http://cran.r-project.org/web/packages/neuralnet/index.html.

R software, which is freely available from http://www.r-project.org/, (version 1.3 of Neuralnet, written by Stefan Fritsch and Frauke Guenther following the work by Marc Suling) may, for example, be used to construct a neural network.

Reference is also made to the examples below, in particular to point 2 of Example 1 below (NN model).

The comparison of said step ii) may thus in particular be carried out by using the following method and/or by using the following algorithm or software:
mROC,
KNN, WKNN, more particularly WKNN,
RF, or
NN,
more particularly mROC.

Each of these algorithms, or software or methods, may be used to construct a multivariate classification model from values for measurements of each of said reference cohorts, and to combine the values of the measurements obtained for said subject in this model to infer the subject's hepatic fibrosis score therefrom.

In one embodiment of the invention, the multivariate classification model implemented in the method of the invention is expressed by a mathematical function, which may be linear or non-linear, more particularly a linear function (for example, a mROC model). The hepatic fibrosis score of said subject is thus deduced by combining said measurement values obtained for said subject in this mathematical function, in particular a linear or non-linear function, in order to obtain an output value, more particularly a numerical output value, which is an indicator of the hepatic fibrosis score of said subject.

In one embodiment of the invention, the multivariate classification model implemented in the method of the invention is a learning or artificial intelligence model, a non-parametric classification model or heuristic model or a probabilistic prediction model (for example, a WKNN, RF or NN model). The hepatic fibrosis score of said subject is thus induced by combining said measurement values obtained for said subject in a non-parametric classification model or heuristic model or a probabilistic prediction model (for example, a WKNN, RF or NN model) in order to obtain an output value, more particularly an output tag, indicative of the hepatic fibrosis score of said subject.

Alternatively or in a complementary manner, said comparison of step ii) may include the fact of comparing the values for the measurements of the level of expression of said selected genes obtained for said subject, with at least one reference value which discriminates between a hepatic fibrosis with a Metavir fibrotic score of at most F1 and a hepatic fibrosis with a fibrotic Metavir score of at least F2, in order to classify the hepatic fibrosis of said subject into the group of fibrotic scores of at most F1 using the Metavir score system or into the group of fibrotic scores of at least F2 using the Metavir score system.

As an example, the values for the measurements of the level of expression of said selected genes may be compared to their reference values in:
a sub-population of individuals of the same species as said subject, who are preferably infected with the same hepatitis virus or viruses as said subject, and who have a hepatic fibrosis score of at most F1 using the Metavir score system, and/or a sub-population of individuals of subjects of the same species as said subject, who are preferably infected with the same hepatitis virus or viruses as said subject, and who have a hepatic fibrosis score of at least F2 using the Metavir score system, or to a reference value which represents the combination of these reference values.

A reference value may, for example, be:

the value for the measurement of the level of expression of each of said selected genes in each of the individuals for each of the sub-populations or reference cohorts, or a positional criterion, for example the mean or median, or a quartile, or the minimum, or the maximum of these values in each of these sub-populations or reference cohorts, or a combination of these values or means, median, or quartile, or minimum, or maximum.

The reference value or values used must be able to allow the various hepatic fibrosis scores to be distinguished.

Figure 2:
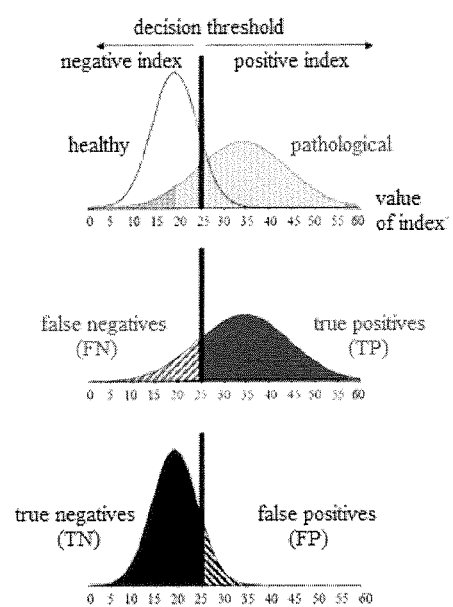
FIG. 2: Distribution of a biomarker of interest of the invention, distinguishing between two clinical populations (population of "healthy" patients versus population of "pathological" patients), and representation of the associated diagnostic characteristics (false negatives (FN), false positives (FP), true positives (TP) and true negatives (TN)), which are fixed as a function of the decision threshold selected by the user.

It may, for example, concern a decision or prediction threshold established as a function of the distribution of the measurement values in each of said sub-populations or cohorts, and as a function of the levels of sensitivity (Se) and specificity (Spe) set by the user (see FIG. 2 and below); (Se=TP/(TP+FN) and Sp=TN/(TN+FP), with TP=number of true positives, FN=number of false negatives, TN=number of true negatives, and FP=number of false positives). This decision or prediction threshold may in particular be an optimal threshold which attributes an equal weight to the sensitivity (Se) and to the specificity (Spe), such as the threshold maximizing Youden's index (J) defined by J=Se+Spe−1.

Alternatively or in a complementary manner, several reference values may be compared. This is the case in particular when the values for the measurements obtained for said subject are compared with their values in each of said sub-populations or reference cohorts, for example with the aid of a machine learning or artificial intelligence classification method.

Thus, the comparison of step ii) may, for example, be carried out as follows:

select the levels of sensitivity (Se) and specificity (Spe) to be given to the method, establish a mathematical function, linear or non-linear, in particular a linear mathematical function (for example, by the mROC method), starting from measurement values for said genes in each of said sub-populations or cohorts, and calculate the decision or prediction threshold associated with this function due to the choices of levels of sensitivity (Se) and specificity (Spe) made (for example, by calculating the threshold maximizing Youden's index), combine the measurement values obtained for said subject into this mathematical function, in order to obtain an output value which, compared with said decision or prediction threshold, can be used to attribute a hepatic fibrosis score to said subject, i.e. to classify said subject into that of these sub-populations or reference cohorts to which it has the greatest probability of belonging.

In particular, the invention is based on the demonstration that, when taken in combination, the levels of expression of:

SPP1, and at least one gene from among A2M and VIM, and at least one gene from among IL8, CXCL10 and ENG, and optionally, at least one gene from among the list of the following sixteen genes: IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1, are biomarkers which provide a "signature" of the hepatic fibrosis score.

The skilled person having available a combination of genes described by the invention is in a position to construct a multivariate classification model, in particular a multivariate statistical analysis model (for example a linear or non-linear mathematical function) or a machine learning or artificial intelligence model (for example, a machine learning or artificial intelligence algorithm), with the aid of his general knowledge in the field of statistical techniques and means, in particular in the domain of statistical processing and interpretation of data, more particularly biological data.

A multivariate classification model may, for example, be constructed, in particular constructed in advance, as follows:

a) for a population of individuals of the same species as said subject, and who are infected with the same hepatitis virus or viruses as said subject, determining the hepatic fibrosis score of each of said individuals of the population, and classifying them into sub-populations as a function of their hepatic fibrosis score, thereby constituting reference cohorts established as a function of their hepatic fibrosis score;

b) in at least one sample which has already been obtained from each of said individuals (the nature of this sample preferably being identical to that of the sample from said subject), measuring the level of transcription or translation of each of said selected genes;

c) carrying out an inter-cohort comparison of the values of the measurements obtained in step b), or the distribution of these values (for example by multivariate statistical analysis), in order to construct a multivariate classification model which infers a hepatic fibrosis score value (or a value representative of this score), from the combination of the levels of transcription or, if appropriate, of translation, of said selected genes.

If said subject or subjects for whom the hepatic fibrosis score is to be determined present this fibrosis due to a particular known chronic hepatic disease, for example due to an infection with hepatitis C virus (HCV), then advantageously, individuals with a comparable clinical situation are used. As an example, if the fibrosis of said subject or subjects the hepatic fibrosis score of whom has to be determined is exclusively due to an infection with hepatitis C virus (HCV), then preferably, individuals who are infected with a HCV are selected, and preferably, individuals whose hepatic fibrosis or its change may be or has been influenced by factors other than HCV, such as (co-) infection with another virus (for example human immunodeficiency virus (HIV), hepatitis B virus), excessive alcohol consumption, haemochromatosis, auto-immune hepatitis, Wilson's disease, α-1 antitrypsin deficiency, primary sclerosing cholangitis, or primary biliary cirrhosis. Preferably, individuals are selected who have not yet received treatment intended to treat their hepatic fibrosis or its source. The individuals are also selected so as to constitute a statistically acceptable cohort having no particular bias, in particular no particular clinical bias. The aim is to construct a multivariate classification model which is as relevant as possible from a statistical point of view.

Preferably, the cohorts or sub-populations of individuals which are used to assay the measurement values or to determine the distributions of the measurement values with which the measurement values obtained for said subject will be compared and/or to construct multivariate classification models, comprise as many individuals as possible.

If the number of individuals is too low, the comparison or the constructed model might not be sufficiently reliable and generalizable in view of the envisaged medical applications.

In particular, cohorts or sub-populations will be selected which each comprise at least 30 individuals, for example at least 40 individuals, preferably at least 50 individuals, more particularly at least 70 individuals, and still more particularly at least 100 individuals.

Preferably, a comparable number of individuals is present in each cohort or sub-population. As an example, the number of individuals of a cohort or sub-population does not exceed the threshold of 3 times the number of individuals of another cohort, more particularly the threshold of 2.5 times the number of individuals of another cohort.

When the statistical analysis carried out uses a mathematical function, such as in the case of a mROC method, for example, the number of individuals required per cohort may optionally be of the order of 20 to 40 individuals per reference cohort. In the case of a machine learning analysis method, such as a KNN, WKNN, RF or NN method, it is preferable to have at least 30 individuals per cohort, preferably at least 70 individuals, still more particularly at least 100 individuals.

In the examples that follow, the total number of individuals included in the set of cohorts (cohort with score F1 and cohort with score F2) is more than 150.

In order to determine the hepatic fibrosis score of an individual, and consequently of attributing that individual to a reference cohort, the skilled person can employ any means that is judged appropriate. As an example, a hepatic biopsy puncture (HBP) may be carried out on said individual and the hepatic tissue removed may then by analysed by anatomo-pathologic examination in order to determine the hepatic fibrosis score of that individual (for example at most F1 or at least F2). Since the scores of each individual are used as a basis for the statistical analysis and not as an individual diagnosis of the individual, the means used for measuring the score may optionally be prior art means such as the Fibrotest®, Fibrometrer® or Hepascore® test. However, it is preferable to use anatomo-pathologic rather than a HBP sample because, in contrast to Fibrotest®, Fibrometrer® or Hepascore® tests, this examination is capable of discriminating between a hepatic fibrosis score of at most F1 and a score of at least F2.

Although the number of samples taken from a given individual should of course be limited, in particular in the case of hepatic biopsy puncture, several samples can be collected from the same individual. In this case, the results of measuring the various samples of the same individual are considered as their resultant mean; it is not assumed that they could be equivalent to the measurement values obtained from distinct individuals.

The comparison of the values of the measurements in each of said cohorts may be carried out using any means known to the skilled person. It is generally carried out by statistical treatment and interpretation of measurement values for levels of expression of said selected genes which are measured for each of said cohorts. This multivariate statistical comparison can be used to construct a multivariate classification model which infers a value for the hepatic fibrosis score from a combination of the levels of expression of said selected genes, more particularly a multivariate classification model which uses a combination of the levels of expression of the said selected genes in order to discriminate as a function of the hepatic fibrosis score.

Once said multivariate classification model has been constructed, it can be used to analyse the values of measurements obtained for said subject, and above all be re-used for the analysis of the measurements from other subjects. Thus, said multivariate classification model can be set up independently of measurements made for said subject or said subjects and may be constructed in advance.

Should it be necessary, rather than constitute the cohorts and combine the data from the individuals who make them up, in order to construct examples of multivariate classification models in accordance with the invention, the skilled person may use subjects who are described in the Examples section below as individuals of the cohorts and may, in the context of individual cohort data (in fact, cohorts F1 and F2), use the data which are presented for these subjects in the examples below, more particularly:

in Table 22 and/or in Table 23, which present the measurement values for a group of 20 patients (10 F1 patients and 10 F2 patients) for the genes A2M, CXCL10, IL8, SPP1 and VIM; and/or in Table 25 and/or in Table 26 and/or in Table 27 and/or in Table 28 below, which present the measurement values for a group of 158 patients (102 F1 patients and 56 F2 patients) for each of the genes which may be selected in accordance with the invention.

It is preferable to use the data of Tables 25 and/or 26 and/or 27 and/or 28, which pertain to a group of 158 patients, rather than to use only those of Tables 22 and/or 23, which concern only 20 patients.

For the 158 patients for whom the measurement values for the levels of expression of all of the genes which are susceptible of being selected in accordance with the invention, Tables 25, 26, 27 and 28 below present the values for clinical factors, virological factors and biological factors other than the levels of expression of said selected genes are also presented in Table 24 below.

Preferably, said multivariate classification model is a particularly discriminating system. Advantageously, said multivariate classification model has a particular area under the ROC curve (or AUC) and/or LOOCV error value.

The acronym "AUC" denotes the Area Under the Curve, and ROC denotes the Receiver Operating Characteristic. The acronym "LOOCV" denotes Leave-One-Out-Cross-Validation, see Hastie, Tibishirani and Friedman, 2009.

The characteristic of AUC is that it can be applied in particular to multivariate classification models which are defined by a mathematical function such as, for example, the models using a mROC classification method.

Multivariate artificial intelligence or machine learning models cannot properly be said to be defined by a mathematical function. Nevertheless, since they involve a decision threshold, they can be understood by means of a ROC curve, and thus by an AUC calculation. This is the case, for example, with models using a RF (random forest) method. In fact, in the case of the RF method, a ROC curve may be calculated from predictions of OOB (out-of-bag) samples.

In contrast, those of the multivariate artificial intelligence or machine learning models which could not be characterized by an AUC value, in common with all other multivariate artificial intelligence or machine learning models, can be characterized by the value of the "classification error" parameter which is associated with them, such as the value for the LOOCV error, for example.

Said particular value for the AUC may in particular be at least 0.60, at least 0.61, at least 0.66, more particularly at least 0.69, at least 0.70, at least 0.71, at least 0.72, at least 0.73, at least 0.74, still more particularly at least 0.75, still more particularly at least 0.76, still more particularly at least 0.77, in particular at least 0.78, at least 0.79, at least 0.80 (preferably, with a 95% confidence interval of at most ±11%, more particularly of less than ±10.5%, still more particularly of less than ±9.5%, in particular of less than ±8.5%); see for example, Tables 5, 7, 11 and 13 below.

Advantageously, said particular LOOCV error value is at most 30%, at most 29%, at most 25%, at most 20%, at most 18%, at most 15%, at most 14%, at most 13%, at most 12%, at most 11%, at most 10%, at most 9%, at most 8%, at most 7%, at most 6%, at most 5%, at most 4%, at most 3%, at most 2%, at most 1%.

The diagnostic performances of a biomarker are generally characterized in accordance with at least one of the following two indices:
- the sensitivity (Se), which represents its capacity to detect the population termed "pathologic" constituted by individuals termed "cases" (in fact, patients with a hepatic fibrosis score of F2 or more);
- the specificity (Sp or Spe), which represents its capacity to detect the population termed "healthy", constituted by patients termed "controls" (in fact, patients with a hepatic fibrosis score of F1 or less).

When a biomarker generates continuous values (for example concentration values), different positions of the Prediction Threshold (or PT) may be defined in order to assign a sample to the positive class (positive test: y=1). The comparison of the concentration of the biomarker with the PT value means that the subject can be classified into the cohort to which it has the highest probability of belonging.

As an example, if a cohort of individuals with a fibrotic score of at least F2 and a cohort of individuals with a fibrotic score of at most F1 are considered, and if a subject or patient p is considered for whom the clinical state is to be determined and for whom the value of the combination of measurements is V (V being equal to Z in the case of mROC models), the decision rule is as follows:
- when the mean value for the combination of the levels of expression of said genes in the cohort of "F2 or more" individuals is higher than that of the cohort of "F1 or less" individuals:
  - if V≥PT: the test is positive, a fibrotic score of "F2 or more" is assigned to said patient p,
  - if V<PT: the test is negative, a fibrotic score of "F1 or less" is assigned to said patient p, or
- when the mean value of the combination of the levels of expression of said genes in the cohort of "F2 or more" individuals is lower than that of the cohort of "F1 or less" individuals:
  - if V≤PT: the test is positive, a fibrotic score of "F2 or more" is assigned to said patient p,
  - if V>PT: the test is negative, a fibrotic score of "F1 or less" is assigned to said patient p.

Since the combination of biomarkers of the invention is effectively discriminate, the distributions, which are assumed to be Gaussian, of the combination of biomarkers in each population of interest (for example in the "F2 or more" cohort and in the "F1 or less" cohort) are clearly differentiated. Thus, the optimal threshold value which will provide this combination of biomarkers with the best diagnostic performances can be defined.

In fact, for a given threshold PT, the following values may be calculated (see FIG. 2):
- the number of true positives: TP;
- the number of false negatives: FN;
- the number of false positives: FP;
- the number of true negatives: TN.

The calculations of the parameters of sensitivity (Se) and specificity (Sp) are deduced from the following formulae:

$$Se = TP/(TP+FN);$$

$$Sp = TN/(TN+FP).$$

The sensitivity can thus be considered to be the probability that the test is positive, knowing that the Metavir F score of the tested subject is at least F2; and the specificity can be considered to be the probability that the test is negative, knowing that the Metavir F score of the tested subject is at most F1.

An ROC curve can be used to visualize the predictive power of the biomarker (or, for the multivariate approach, the predictive power of the combination of biomarkers integrated into the model) for different values of PT (Swets 1988). Each point of the curve represents the sensitivity versus (1-specificity) for a specific PT value.

Figure 3:
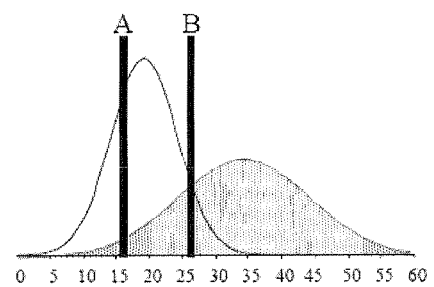
FIG. 3: Trace for the ROC curve (Receiver Operating Characteristic) for a biomarker of interest of the invention. Each value for the fixed threshold (threshold A, threshold B) generates a pair of values (Se, 1-Sp) which are recorded on a graph on an orthonormal plane where the (x) abscissae represent (1-Sp), varying from 0 to 1, and where the (y) ordinates represent (Se).
Figure 3:
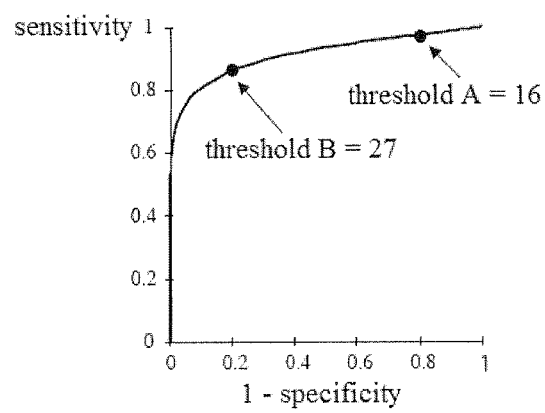

For example, if the concentrations of the biomarker of interest vary from 0 to 35, different PT values may be successively positioned at 0.5; 1; 1.5; . . . ; 35. Thus, for each PT value, the test samples are classified, the sensitivity and the specificity are calculated and the resulting points are recorded on a graph (see FIG. 3).

Figure 4:
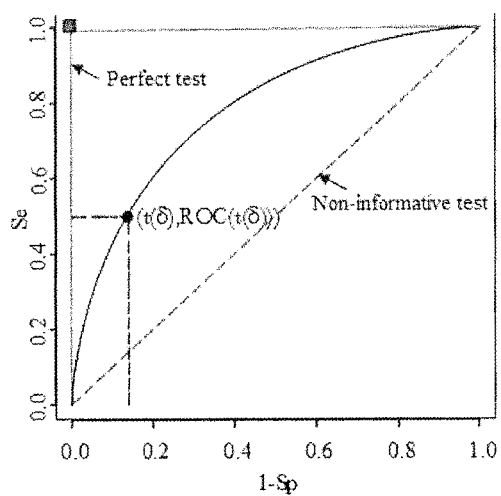
FIG. 4: Graphical representation in the form of a ROC curve of the perfect diagnostic test (area under the curve, AUC=1) and for the non-informative diagnostic test (area under the curve or AUC=0.5).

The closer the ROC curve comes to the first diagonal (straight line linking the lower left hand corner to the upper right hand corner), the worse is the discriminating performance of the model (see FIG. 4). A test with a high discriminating power will occupy the upper left hand portion of the graph. A less discriminating test will be close to the first diagonal of the graph. The area under the ROC curve (AUC) is a good indicator of diagnostic performance. This varies from 0.5 (non-discriminating biomarker) to 1 (completely discriminating biomarker). A value of 0.70 is indicative of a discriminating biomarker.

An ROC curve can be approximated by two principal techniques: parametric and non-parametric (Shapiro 1999). In the first case, the data are assumed to follow a specific statistical distribution (for example Gaussian) which is then adjusted to the observed data to produce a smoothed ROC curve. Non-parametric approaches consider the estimation of Se and (1-Sp) from observed data. The resulting empirical ROC curve is not a smoothed mathematical function but a step function curve.

The choice of threshold or optimal threshold, denoted δ (delta), depends on the priorities of the user in terms of sensitivity and specificity. In the case where equal weights are attributed to sensitivity and specificity, this latter can be defined as the threshold maximizing the Youden's index (J=Se+Sp−1).

Advantageously, the means of the invention can be used to obtain:
- a sensitivity [Se=TP/(TP+FN)] of at least 67% (or more), and/or
- a specificity [Sp=TN/(TN+FP)] of at least 67% (or more).

In the context of the invention, the sensitivity is a particularly important characteristic in that the main clinical need is the identification of patients with a Metavir F score of at least F2.

Thus, and advantageously, the application more particularly pertains to means of the invention which reach or can be used to reach a sensitivity of 67% or more.

More particularly, the means of the invention reach or can be used to reach a sensitivity of 67% or more and a specificity of 67% or more.

It is the particular selection of genes proposed by the invention which means that these sensitivity and/or specificity scores, more particularly these sensitivity scores, and still more particularly these sensitivity and specificity scores, can be reached.

Thus, in one advantageous embodiment of the invention, the hepatic fibrosis score of said subject is inferred:
with a sensitivity of at least 67% (or more) and/or a specificity of at least 67% (or more),
more particularly with a sensitivity of at least 67% (or more),
still more particularly with a sensitivity of at least 67% (or more) and a specificity of at least 67% (or more).

In accordance with the invention, the sensitivity may be at least 67%, at least 68%, at least 69%, at least 70%, at least 71%, at least 72%, at least 73%, at least 74%, at least 75% (see, for example, the selected genes of combination Nos. 1 to 29 in Table 3 below, more particularly the sensitivity characteristics of the combinations of the levels of transcription or translation of these genes presented in Tables 5, 7, 11 and 13 below).

Alternatively or in a complementary manner, the specificity may be at least 67%, at least 68%, at least 69%, at least 70%, at least 71%, at least 72%, at least 73%, at least 74%, at least 75% (see, for example, genes selected from combinations Nos. 1 to 29 of Table 3 below, more particularly the specificity characteristics of combinations of the levels of transcription or translation of these genes presented in Tables 5, 7, 11 and 13 below).

All combinations of these sensitivity thresholds and these specificity thresholds are explicitly included in the content of the application (see, for example, the selected genes of combination Nos. 1 to 29 of Table 3 below).

For example, the sensitivity may be at least 71%, at least 73%, or at least 75%, and the specificity at least 70% or a higher threshold (see, for example, the selected genes of combination Nos. 1, 4, 7, 9 to 11, 13, 14, 16, 18, 19, 20 to 24, 26, 27 and 29 of Table 3 below, more particularly the sensitivity and specificity characteristics of combination Nos. 1, 4, 7, 9 to 11, 13, 14, 18 to 24, 26 to 27, 29 of the levels of transcription presented in Table 5 below, and the sensitivity and specificity characteristics of combination Nos. 4 and 16 of the levels of transcription presented in Table 11 below).

More particularly, all combinations comprising at least the combination of a sensitivity threshold and a specificity threshold are explicitly included in the content of the application.

Alternatively or in a complementary manner to these characteristics of sensitivity and/or specificity, the negative predictive values (NPV) reached or which might be reached by the means of the invention are particularly high.

The NPV is equal to TN/(TN+FN), with TN=true negatives and FN=false negatives, and thus represents the probability that the test subject is at most F1, knowing that the test of the invention is negative (the result given by the test is: score of F1 or less).

In accordance with the invention, the NPV may be at least 80%, or at least 81%, at least 82%, at least 83%, at least 84% (see, for example, the selected genes of combination Nos. 1 to 29 of Table 3 below, more particularly the NPV characteristics of combinations of the levels of transcription or translation of these genes presented in Tables 5, 7, 11 and 13 below).

Here again, it is the particular selection of genes proposed by the invention which means that these NPV levels can be reached.

For example, the means of the invention reach or can be used to reach:
a sensitivity of at least 71%, at least 73%, or at least 75%, and
a specificity of at least 70% (or a higher threshold), and/or a NPV of at least 81% or at least 82%,
(see, for example, the selected genes of combination Nos. 1, 4, 7, 9 to 11, 13, 14, 16, 18, 19, 20 to 24, 26, 27 and 29 of Table 3 below, more particularly the sensitivity, specificity and NPV characteristics of combination Nos. 1, 4, 7, 9 to 11, 13, 14, 18, 19, 20 to 24, 26, 27 and 29 of the levels of transcription presented in Table 5 below, and the sensitivity, specificity and NPV characteristics of combination Nos. 4 and 16 of the levels of transcription presented in Table 11 below).

More particularly, the means of the invention reach or can be used to reach:
a sensitivity of at least 73%, and
a specificity of at least 70% (or a higher threshold), and/or a NPV of at least 81% or at least 82%,
(see, for example, the selected genes of combination Nos. 1, 4, 7, 10, 13, 19, 21, 23 of Table 3 below, more particularly the sensitivity, specificity and NPV characteristics of the combination of the levels of transcription of these genes presented in Tables 5 and 11 below).

More particularly, the means of the invention reach or can be used to reach:
a sensitivity of at least 75%, and
a specificity of at least 70% (or a higher threshold), and/or a NPV of at least 81% or at least 82%,
(see, for example, the selected genes of combination Nos. 1, 4, 7 and 13 of Table 3 below, more particularly the sensitivity, specificity and NPV characteristics of the combination of the levels of transcription of these genes presented in Tables 5 and 11 below).

All combinations of NPV thresholds and/or sensitivity thresholds and/or specificity thresholds are explicitly included in the content of the application.

More particularly, all combinations comprising at least the combination of a sensitivity threshold and a NPV threshold are explicitly included in the content of the application.

Alternatively or in a complementary manner to these characteristics of sensitivity and/or specificity and/or NPV, the positive predictive values (PPV) obtained or which might be obtained by the means of the invention are particularly high.

The PPV is equal to TP/(TP+FP) with TP=true positives and FP=false positives, and thus represents the probability that the test subject is at least F2, knowing that the test of the invention is positive (test result is: score of F2 or more).

In accordance with the invention, the PPV may be at least 50%, or at least 55%, or at least 56%, or at least 57% or at least 58% or at least 59% or at least 60% (see, for example, the selected genes of combination Nos. 1 to 29 of Table 3 below, more particularly the PPV characteristics of combinations of the levels of transcription or translation of these genes presented in Tables 5, 7, 11, 13 below).

Here again, it is the particular selection of genes proposed by the invention which means that these PPV levels can be reached.

For example, the means of the invention reach or can be used to reach:
a sensitivity of at least 71%, at least 73%, or at least 75%, and a specificity of at least 70% (or a higher threshold), and/or
a NPV of at least 81% or at least 82%, and/or a PPV of
at least 55%, or at least 57%,
(see, for example, the selected genes of combination Nos. 1,
4, 7, 9 to 11, 13, 14, 16, 18, 19, 20 to 24, 26, 27 and 29 of
Table 3 below, more particularly the sensitivity, specificity,
NPV and PPV characteristics of combination Nos. 1, 4, 7, 9
to 11, 13, 14, 18, 19, 20 to 24, 26, 27 and 29 of the levels
of transcription presented in Table 5 below, and the sensitivity, specificity, NPV and PPV characteristics of combination Nos. 4 and 16 of the levels of transcription presented
in Table 11 below).

More particularly, the means of the invention reach or can
be used to reach:
a sensitivity of at least 73%, and
a specificity of at least 70% (or a higher threshold), and/or
a NPV of at least 81% or at least 82%, and/or a PPV of
at least 57%,
(see, for example, the selected genes of combination Nos. 1,
4, 7, 10, 13, 19, 21, 23 of Table 3 below, more particularly
the sensitivity, specificity, NPV and PPV characteristics of
the combination of the levels of transcription of these genes
presented in Tables 5 and 11 below).

More particularly, the means of the invention reach or can
be used to reach:
a sensitivity of at least 75%, and
a specificity of at least 70% (or a higher threshold), and/or
a NPV of at least 81% or at least 82%, and/or a PPV of
at least 57%,
(see, for example, the selected genes of combination Nos. 1,
4, 7 and 13 of Table 3 below, more particularly the sensitivity, specificity, NPV and PPV characteristics of the combination of the levels of transcription of these genes presented in Tables 5 and 11 below).

All combinations of PPV and/or NPV thresholds and/or
sensitivity thresholds and/or specificity thresholds are
explicitly included in the content of the application.

More particularly, all combinations comprising at least
the combination of a sensitivity threshold and a PPV threshold are explicitly included in the content of the application.

More particularly, all combinations comprising at least
one of said NPV thresholds and/or at least one of said
sensitivity thresholds, more particularly at least one of said
NPV thresholds and one of said sensitivity thresholds, more
particularly at least one of said NPV thresholds and one of
said sensitivity thresholds and one of said specificity thresholds are included in the application.

The Tables 5, 7, 11 and 13 presented below provide
illustrations:
of values for the area under the ROC curve (AUC),
of values for sensitivity and/or specificity, more particularly sensitivity, still more particularly sensitivity and
specificity,
of values for the negative predictive value (NPV) and/or
positive predictive value
(PPV), more particularly NPV, still more particularly
NPV and PPV,
attained by combinations of genes in accordance with the
invention (Tables 5 and 11: combinations of levels of
transcription; Tables 7 and 13: combinations of levels of
translation).

The predictive combinations of the invention comprise
combinations of levels of gene expression selected as indicated above.

As will be indicated in more detail below, and as illustrated in the examples below (see Examples 2c, 2d, 3b)
below), it may, however, be possible to elect to involve one
or more factors in these combinations other than the levels
of expression of these genes, in order to combine this or
these other factors and the levels of expression of the
selected genes into one decision rule.

This or these other factors are preferably selected so as to
construct a classification model the predictive power of
which is further improved with respect to the model which
does not comprise this or these other factors.

In addition to the level of expression of said selected
genes, it is thus possible to assay or measure one or more
other factors, such as one or more clinical factors and/or one
or more virological factors and/or one or more biological
factors other than the level of expression of said selected
genes.

The value(s) of this (these) other factors may then be
taken into account in order to construct the multivariate
classification model and may thus result in still further
improved classification performances, more particularly in
augmented sensitivity and/or specificity and/or NPV and/or
PPV characteristics.

As an example, if the values presented for combination
No. 16 or No. 4 in Tables 5 and 11 below are compared, it
can be seen that the values for AUC, Se, Spe NPV and PPV,
more particularly the values for AUC, Se, NPV, increase
when the combination of the levels of transcription of said
selected genes are also combined with other factors, in
particular other biological factors.

Similarly, if the values presented for combination No. 16
in Tables 7 and 13 below are compared, it can be seen that
several of the values for AUC, Se, Spe, NPV and PPV, more
particularly the values for AUC, Spe and NPV, increase
when the combination of the levels of translation of said
selected genes are also combined with other factors, in
particular other biological factors.

Advantageously, when one or more other factors are
combined with a combination of genes selected from said
list of twenty-two genes of the invention, at least one of the
characteristics of AUC (if appropriate, the LOOCV error),
sensitivity, specificity, NPV and PPV, is improved thereby.

In accordance with one embodiment of the invention, the
particular value for AUC associated with such an improved
combination is at least 0.70, at least 0.71, at least 0.72, at
least 0.73, more particularly at least 0.74, still more particularly at least 0.75, still more particularly at least 0.76, still
more particularly at least 0.77, in particular at least 0.78, at
least 0.79, at least 0.80 (preferably, with a 95% confidence
interval of at most ±11%, more particularly of less than
±10.5%, still more particularly of less than ±9.5%, in
particular of less than ±8.5%); see for example, Tables 5, 11
and 13 below.

In accordance with one embodiment of the invention, the
threshold specificity value associated with such an improved
combination is at least 70%, at least 71%, at least 72%, at
least 73%, at least 74%, at least 75% (see, for example, the
selected genes of combination Nos. 1 to 29 of Table 3 below,
more particularly the specificity characteristics of combinations of the levels of transcription of these genes presented
in Tables 11 and 13 below).

As indicated above, and as illustrated below, the means of
the invention involve measuring the level of expression of:
SPP1, and
at least one gene from among A2M and VIM, and
at least one gene from among IL8, CXCL10 and ENG,
and
optionally, at least one gene from among the list of the
following sixteen genes: IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1.

In accordance with the invention, the total number of genes selected thereby for which the level of expression is measured is thus at least three.

In accordance with one embodiment of the invention, this total number of genes selected thereby is 3, 4, 5, 6, 7, 8, 9, 10, 11, 12, 13, 14, 15, 16, 17, 18, 19, 20, 21 or 22, more particularly 3, 4, 5, 6, 7, 8, 9, 10, still more particularly 3, 4, 5, 6, 7, still more particularly 3, 4, 5 or 6. Advantageously, this number of selected genes is 3, 4 or 5, in particular 4 or 5 (see, for example, the selected genes of combination Nos. 1 to 29 of Table 3 below).

In accordance with one embodiment, the total number of genes selected from said list of twenty-two genes of the invention is 3, 4, 5 or 6 genes, more particularly 4 or 5 genes, with:
  a sensitivity of at least 70%, at least 71%, at least 72%, at least 73%, at least 74%, at least 75%; and/or with
  a specificity of at least 70%, at least 71%, at least 72%, at least 73%, at least 74%, at least 75%; and/or with
  a NPV of at least 80%, at least 81%, at least 82%, at least 83%, at least 84%; (see, for example, the selected genes of combination Nos. 1 to 29 of Table 3 below).

As an example, the application envisages a number of 3, 4, 5 or 6 genes selected from said list of twenty-two genes of the invention, more particularly 4 or 5 genes selected from said list of twenty-two genes of the invention, with:
  a sensitivity of at least 70%, at least 71%, at least 72%, at least 73%, at least 74%, at least 75%; and/or with
  a specificity of at least 70%, at least 71%, at least 72%, at least 73%, at least 74%, at least 75%;
more particularly, a number of 3, 4, 5 or 6 genes selected from said list of twenty-two genes of the invention, more particularly 4 or 5 genes selected from said list of twenty-two genes of the invention, with a sensitivity of at least 70%, at least 71%, at least 72%, at least 73%, at least 74%, at least 75% (see, for example, the selected genes of combination Nos. 1 to 29 of Table 3 below).

Any combinations of the total number of selected genes and/or the sensitivity threshold and/or the specificity threshold and/or the NPV threshold and/or the PPV threshold indicated above are explicitly included in the content of the application.

More particularly, the total number of genes selected from said list of twenty-two genes of the invention is 3, 4, 5 or 6 genes, more particularly 4 or 5 genes, with:
  a sensitivity of at least 73%; and/or with
  a specificity of at least 70%; and/or with
  a NPV of at least 83%;
(see, for example, the selected genes of combination Nos. 1, 4, 7, 10, 13, 19, 21, 23 of Table 3 below).

More particularly, the total number of genes selected from said list of twenty-two genes of the invention is 3, 4, 5 or 6 genes, more particularly 4 or 5 genes, with:
  a sensitivity of at least 75%; and/or with
  a specificity of at least 70%; and/or with
  a NPV of at least 83%;
(see, for example, the selected genes of combination Nos. 1, 4, 7, 13 of Table 3 below).

The genes which are selected in accordance with the invention are:
  SPP1, and
  at least one gene from among A2M and VIM, and
  at least one gene from among IL8, CXCL10 and ENG, and
  optionally, at least one gene from among the following sixteen genes: IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1.

The choice of genes is made as a function of the demands or wishes for the performance to be obtained, for example as a function of the sensitivity and/or specificity and/or NPV and/or PPV which is to be obtained or anticipated. Clearly, the lower the number of selected genes, the simpler the means of the invention are to implement.

All possible choices of genes are explicitly included in the application.

In a manner similar to that indicated above for the sensitivity thresholds, the specificity thresholds, the NPV thresholds, the PPV thresholds and the total number of selected genes, all combinations of genes selected from each of the lists of genes and/or the total numbers of genes selected and/or sensitivity thresholds and/or specificity thresholds and/or NPV thresholds and/or PPV thresholds are explicitly included in the content of the application.

The genes selected from said list of twenty-two genes of the invention are:
  SPP1, and
  at least one gene from among a first list of genes formed by A2M and VIM, and
  at least one gene from among a second list of genes formed by IL8, CXCL10 and ENG, and
  optionally, at least one gene from among a third list of genes formed by the following sixteen genes: IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1,
in addition to SPP1, it is possible to select:
  one or two genes from among A2M and VIM (first list of genes), and
  one, two or three genes from among IL8, CXCL10 and ENG (second list of genes), and
  zero to sixteen genes, for example, zero, one, two or three genes, in particular zero, one or two genes from among said third list of sixteen genes (optional list).

Alternatively or in a complementary manner, the following are selected:
  from zero, one, two or three genes, more particularly zero, one or two genes, from among the list of sixteen optional genes; and/or
  a total number of selected genes of four or five genes;
see for example, combination Nos. 1 to 29 of Table 3 below.

Advantageously, the following is selected:
  SPP1, and
  one or two genes from among A2M and VIM, more particularly at least A2M, and
  one, two or three genes from among IL8, CXCL10 and ENG, more particularly at least IL8, and
  zero, one, two or three genes from among said optional list of sixteen genes, more particularly zero, one or two genes from among this list.

Of the genes of the first list, it is possible to select A2M and/or VIM. Thus, it is possible to select the following:
  A2M, or
  VIM, or
  A2M and VIM,
for example, at least A2M, i.e.:
  A2M, or
  A2M and VIM;
see for example, combination Nos. 1 to 28 of Table 3 below.

Alternatively or in a complementary manner, of the genes of the second list, it is possible to select IL8 and/or CXCL10 and/or ENG. Advantageously, at least IL8 is selected, i.e.:
IL8, or
IL8 and CXCL10, or
IL8 and ENG, or
IL8 and CXCL10 and ENG;
see for example, combination Nos. 1 to 18 and 22 to 29 of Table 3 below.

In accordance with one embodiment of the invention, at least A2M is selected from the first list as indicated above and/or at least IL8 in the second list as indicated above (see for example, combination Nos. 1 to 29 of Table 3 below).

Alternatively or in a complementary manner, of the genes of the third list, i.e. from among the list of sixteen optional genes, zero, one, two or three genes, more particularly zero, one or two genes may in particular be selected.

More particularly, it is possible to select zero, one, two or three genes, in particular zero, one or two genes from among IL6ST, MMP9, S100A4, p14ARF, CHI3L1.

In accordance with one embodiment of the invention, the following is selected:
at least A2M in the first list, and/or at least IL8 in the second list, and
zero genes from the third list, i.e. from the list of sixteen optional genes, or one or more genes from among this list of sixteen optional genes, including at least one or two genes from among IL6ST, MMP9, S100A4, p14ARF and CHI3L1 (for example, one or two of these genes), more particularly at least one or two genes from among IL6ST, MMP9 and S100A4 (for example, one or two of these genes);
see for example, combination Nos. 1 to 17, 19 to 23, 25, 27, more particularly combination Nos. 1 to 17, 19 to 23 of Table 3 below.

In accordance with one embodiment of the invention, the following is selected:
A2M or at least A2M in the first list of genes, and
zero, one, two or three genes, more particularly zero, one or two genes, from among the list of sixteen optional genes, and
a total number of selected genes of four or five genes;
see for example, combination Nos. 1 to 28 of Table 3 below.

In accordance with one embodiment of the invention, the following is selected:
IL8 or at least IL8 in the second list of genes, and
zero, one, two or three genes, more particularly zero, one or two genes, from among the list of sixteen optional genes, and
a total number of selected genes for the whole of the combination, of four or five genes;
see for example, combination Nos. 1 to 18 and 22 to 29 of Table 3 below.

In accordance with one embodiment of the invention, the following is selected:
A2M or at least A2M in the first list, and/or IL8 or at least IL8 in the second list, and
zero genes from the third list, i.e. the list of sixteen optional genes, or one or more genes from among this list of sixteen optional genes, including at least one or two genes from among IL6ST, MMP9, S100A4, p14ARF and CHI3L1 (for example, one or two of these genes), more particularly at least one or two genes from among IL6ST, MMP9 and S100A4 (for example, one or two of these genes), and
a total number of selected genes for the whole of the combination, of four or five genes;
see for example, combination Nos. 1 to 17, 19 to 23, 25, 27, more particularly the combination Nos. 1 to 17, 19 to 23 of Table 3 below.

In accordance with one embodiment of the invention, the following is selected:
A2M or at least A2M in the first list of genes, and
IL8 or at least IL8 in the second list of genes, and/or MMP9 or at least MMP9 from among the list of sixteen optional genes,
the total number of genes selected from the list of sixteen optional genes being zero, one or two genes (for example MMP9, or MMP9 and p14ARF), and
a total number of selected genes for the whole of the combination being four or five genes;
see for example, combination Nos. 1 to 18, 19, 21, and 22 to 29 of Table 3 below.

In accordance with one embodiment of the invention, said selected genes are:
SPP1, and
A2M, or at least A2M from among A2M and VIM, and
IL8, or at least IL8 from among IL8, CXCL10 and ENG,
optionally, at least one gene from the list of sixteen genes mentioned above;
see for example, gene combination Nos. 1 to 18 and 22 to 28 presented in Table 3 below.

In accordance with one embodiment, said genes selected from said list of twenty-two genes of the invention are:
SPP1, and
A2M, or at least A2M from among A2M and VIM, and
CXCL10 and/or ENG, or at least CXCL10 and/or ENG from among IL8, CXCL10 and ENG, and
optionally, at least one gene from among the list of sixteen genes mentioned above;
see for example, gene combination Nos. 4, 7, 8, 13, 16, 18, 19, 20, 21, 25, 28 presented in Table 3 below, more particularly gene combination Nos. 19 to 21.

In accordance with one embodiment, said genes selected from said list of twenty-two genes of the invention are:
SPP1, and
A2M, or at least A2M from among A2M and VIM, and
CXCL10 and/or ENG, or at least CXCL10 and/or ENG from among IL8, CXCL10 and ENG, and
optionally, MMP9 or at least MMP9 from said list of sixteen genes (for example, MMP9 and p14ARF);
see for example, gene combination Nos. 4, 19 and 21 presented in Table 3 below.

Hence, in accordance with one embodiment of the invention, said genes selected from said list of twenty-two genes of the invention may be defined as being:
SPP1, and
at least one gene from among A2M and VIM, and
at least one gene from among IL8, CXCL10 and ENG, and
optionally, at least one gene from among the list of the following sixteen genes: IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1,
while comprising at least:
A2M, and
IL8 and/or MMP9;
see for example, gene combination Nos. 1 to 19 and 21 to 28 presented in Table 3 below.

In accordance with one embodiment, said genes selected from said list of twenty-two genes of the invention may be:
SPP1, and
at least one gene from among A2M and VIM, preferably A2M or at least A2M from among A2M and VIM, and
at least one gene from among IL8, CXCL10 and ENG, and
optionally, at least one gene from among IL6ST, MMP9, S100A4, p14ARF, CHI3L1.

When said genes selected from said list of twenty-two genes of the invention comprise at least one gene from among IL6ST, MMP9, S100A4, p14ARF and CHI3L1, they may also comprise at least one gene from among ANGPT2, CXCL11, MMP2, MMP7, TIMP1, COL1A1, CXCL1, CXCL6, IHH, IRF9 and MMP1.

See, for example, gene combination Nos. 1 to 6, 8 to 9, 11 to 12, 14 to 17, 19, 21 to 23, 25 to 27 presented in Table 3 below.

In accordance with one embodiment, said genes selected from said list of twenty-two genes of the invention may be:
SPP1, and
  at least one gene from among A2M and VIM, preferably A2M or at least A2M from among A2M and VIM, and
  at least one gene from among IL8, CXCL10 and ENG, and
  optionally, at least one gene from among IL6ST, MMP9 and S100A4.

When said genes selected from said list of twenty-two genes of the invention comprise at least one gene from among IL6ST, MMP9 and S100A4, they may also comprise at least one gene from among p14ARF, CHI3L1, ANGPT2, CXCL11, MMP2, MMP7, TIMP1, COL1A1, CXCL1, CXCL6, IHH, IRF9 and MMP1.

See, for example, gene combination Nos. 1 to 6, 8 to 9, 11 to 12, 14 to 17, 19, 21 to 23 presented in Table 3 below.

As an example, said genes selected from said list of twenty-two genes of the invention comprise, or are:
SPP1, A2M, IL8, CHI3L1 and IL6ST (combination No. 1); or
SPP1, A2M, IL8, ANGPT2 and IL6ST (combination No. 2); or
SPP1, A2M, IL8, IL6ST and MMP2 (combination No. 3); or
SPP1, A2M, IL8, VIM and CXCL10 (combination No. 4); or
SPP1, A2M, IL8, IL6ST and MMP9 (combination No. 5); or
SPP1, A2M, IL8, IL6ST and MMP1 (combination No. 6); or
SPP1, A2M, IL8, VIM, and ENG (combination No. 7); or
SPP1, A2M, IL8, CXCL10 and IL6ST, (combination No. 8); or
SPP1, A2M, IL8, CXCL1 and IL6ST (combination No. 9); or
SPP1, A2M, IL8 and VIM (combination No. 10); or
SPP1, A2M, IL8, COL1A1 and IL6ST (combination No. 11); or
SPP1, A2M, IL8, CXCL11 and IL6ST (combination No. 12); or
SPP1, A2M, IL8, CXCL10 and ENG (combination No. 13); or
SPP1, A2M, IL8, IL6ST and TIMP1 (combination No. 14); or
SPP1, A2M, IL8, IHH and IL6ST (combination No. 15); or
SPP1, A2M, IL8, CXCL10 and S100A4 (combination No. 16); or
SPP1, A2M, IL8, IL6ST and MMP7 (combination No. 17); or
SPP1, A2M, IL8, ENG and CXCL11 (combination No. 18); or
SPP1, A2M, ENG and MMP9 (combination No. 19); or
SPP1, A2M, CXCL10 and ENG (combination No. 20); or
SPP1, A2M, CXCL10, p14ARF and MMP9 (combination No. 21); or
SPP1, A2M, IL8, CXCL6 and IL6ST (combination No. 22); or
SPP1, A2M, IL8 and S100A4 (combination No. 23); or
SPP1, A2M, IL8, ANGPT2 and MMP7 (combination No. 24); or
SPP1, A2M, IL8, CXCL10 and p14ARF (combination No. 25); or
SPP1, A2M, IL8 and TIMP1 (combination No. 26); or
SPP1, A2M, IL8 and p14ARF (combination No. 27); or
SPP1, A2M, IL8, CXCL10 and IRF9 (combination No. 28); or
SPP1, IL8, VIM and MMP2 (combination No. 29).

More particularly, said genes selected from said list of twenty-two genes of the invention comprise, or are:
SPP1, A2M, IL8, CHI3L1 and IL6ST, (combination No. 1); or
SPP1, A2M, IL8, VIM and CXCL10 (combination No. 4); or
SPP1, A2M, IL8, VIM, and ENG (combination No. 7); or
SPP1, A2M, IL8 and VIM (combination No. 10); or
SPP1, A2M, IL8, CXCL10 and ENG (combination No. 13); or
SPP1, A2M, ENG and MMP9 (combination No. 19); or
SPP1, A2M, CXCL10, p14ARF and MMP9 (combination No. 21); or
SPP1, A2M, IL8 and S100A4 (combination No. 23).

In a manner similar to that indicated above for the sensitivity thresholds, the specificity thresholds, the NPV thresholds, the total number of selected genes, the number of selected genes in each list of genes, any chosen combinations of genes and/or numbers of genes selected from each of the lists of genes and/or total numbers of selected genes and/or sensitivity thresholds and/or specificity thresholds and/or NPV thresholds are explicitly included in the content of the application.

Twenty-nine examples of gene combinations in accordance with the invention are presented in Table 3 below.

Examples of multivariate classification models were constructed for each of these gene combinations.

Tables 4, 6, 10 and 12 below present the examples (in fact, mROC models with linear Z function):
Tables 4 and 10: combination of the levels of transcription of the genes (RNA measurement, in fact RNAs contained in a sample containing nucleic acids which are susceptible of being obtained from a sample containing a portion of hepatic parenchyma or cells from a tissue of this type);
Tables 6 and 12: combination of the levels of gene translation (measurement of proteins, in fact seric proteins).

For each of the Z functions of Tables 4, 6, 10 and 12:
the value of the area under the ROC curve (AUC),
an example of the decision threshold PT (in fact, threshold maximizing the Youden's index δ), and associated sensitivity values (Se, as a %), specificity values (Spe, as a %), negative predictive values (NPV, as a %) and positive predictive values (PPV, as a %),
are presented in Tables 5, 7, 11 and 13 respectively.

NPV=TN/(TN+FN) with TN=True Negatives and FN=False Negatives;

PPV=TP/(TP+FP) with TP=True Positives and FP=False Positives.

As an example, in the context of a F2 versus F1 detection, the NPV represents the probability of a test subject being F1 knowing that the test is negative (result given by the test=F1 score); and the PPV represents the probability that a test subject will be F2 knowing that the test is positive (result given by the test=F2 score).

TABLE 3

Twenty-nine examples of combinations of gene expression levels

| No. of combination | Selected genes | | | | |
|---|---|---|---|---|---|
| 1 | A2M | CHI3L1 | IL6ST | IL8 | SPP1 |
| 2 | A2M | ANGPT2 | IL6ST | IL8 | SPP1 |
| 3 | A2M | IL6ST | IL8 | MMP2 | SPP1 |
| 4 | A2M | CXCL10 | IL8 | SPP1 | VIM |
| 5 | A2M | IL6ST | IL8 | MMP9 | SPP1 |
| 6 | A2M | IL6ST | IL8 | MMP1 | SPP1 |
| 7 | A2M | ENG | IL8 | SPP1 | VIM |
| 8 | A2M | CXCL10 | IL6ST | IL8 | SPP1 |
| 9 | A2M | CXCL1 | IL6ST | IL8 | SPP1 |
| 10 | A2M | IL8 | SPP1 | VIM | |
| 11 | A2M | COL1A1 | IL6ST | IL8 | SPP1 |
| 12 | A2M | CXCL11 | IL6ST | IL8 | SPP1 |
| 13 | A2M | CXCL10 | ENG | IL8 | SPP1 |
| 14 | A2M | IL6ST | IL8 | SPP1 | TIMP1 |
| 15 | A2M | IHH | IL6ST | IL8 | SPP1 |
| 16 | A2M | CXCL10 | IL8 | S100A4 | SPP1 |
| 17 | A2M | IL6ST | IL8 | MMP7 | SPP1 |
| 18 | A2M | CXCL11 | ENG | IL8 | SPP1 |
| 19 | A2M | ENG | MMP9 | SPP1 | |
| 20 | A2M | CXCL10 | ENG | SPP1 | |
| 21 | A2M | p14ARF | CXCL10 | MMP9 | SPP1 |
| 22 | A2M | CXCL6 | IL6ST | IL8 | SPP1 |
| 23 | A2M | IL8 | S100A4 | SPP1 | |
| 24 | A2M | ANGPT2 | IL8 | MMP7 | SPP1 |
| 25 | A2M | p14ARF | CXCL10 | IL8 | SPP1 |
| 26 | A2M | IL8 | SPP1 | TIMP1 | |
| 27 | A2M | p14ARF | IL8 | SPP1 | |
| 28 | A2M | CXCL10 | IL8 | IRF9 | SPP1 |
| 29 | IL8 | MMP2 | SPP1 | VIM | |

TABLE 4

Examples of classification models (in fact, mROC models) combining the levels of transcription (RNA transcripts, in fact RNA contained in a sample of tissue or hepatic cells)

| No. of combination of genes (see Table 3 above) | Z function combining the levels of transcription (RNA) of the selected genes | Name of function |
|---|---|---|
| 1 | $Z = 0.400 \times A2M^r + 0.003 \times (-CHI3L1) + 0.363 \times (-IL6ST)^r + 0.015 \times IL8 + 0.438 \times SPP1^r$ | Z1ARN |
| 2 | $Z = 0.404 \times A2M^r + 0.062 \times ANGPT2 + 0.414 \times (-IL6ST)^r + 0.015 \times IL8 + 0.316 \times SPP1^r$ | Z2ARN |
| 3 | $Z = 0.392 \times A2M^r + 0.396 \times (-IL6ST)^r + 0.021 \times IL8 + 0.104 \times MMP2^r + 0.271 \times SPP1^r$ | Z3ARN |
| 4 | $Z = 0.297 \times A2M^r - 0.046 \times CXCL10 + 0.020 \times IL8 + 0.274 \times SPP1^r + 0.253 \times VIM^r$ | Z4ARN |
| 5 | $Z = 0.407 \times A2M^r + 0.406 \times (-IL6ST)^r + 0.013 \times IL8 + 0.038 \times MMP9 + 0.309 \times SPP1^r$ | Z5ARN |
| 6 | $Z = 0.406 \times A2M^r + 0.389 \times (-IL6ST)^r + 0.021 \times IL8 + 0.195 \times (-MMP1) + 0.332 \times SPP1^r$ | Z6ARN |
| 7 | $Z = 0.230 \times A2M^r + 0.204 \times ENG^r + 0.012 \times IL8 + 0.262 \times SPP1^r + 0.177 \times VIM^r$ | Z7ARN |
| 8 | $Z = 0.414 \times A2M^r - 0.013 \times CXCL10 + 0.373 \times (-IL6ST)^r + 0.023 \times IL8 + 0.335 \times SPP1^r$ | Z8ARN |
| 9 | $Z = 0.401 \times A2M^r + 0.062 \times CXCL1 + 0.392 \times (-IL6ST)^r + 0.019 \times IL8 + 0.305 \times SPP1^r$ | Z9ARN |
| 10 | $Z = 0.259 \times A2M^r + 0.012 \times IL8 + 0.267 \times SPP1^r + 0.227 \times VIM^r$ | Z10ARN |
| 11 | $Z = 0.427 \times A2M^r - 0.137 \times COL1A1 + 0.369 \times (-IL6ST)^r + 0.020 \times IL8 + 0.397 \times SPP1^r$ | Z11ARN |
| 12 | $Z = 0.397 \times A2M^r + 0.033 \times CXCL11^r + 401 \times (-IL6ST)^r + 0.020 \times IL8 + 0.321 \times SPP1^r$ | Z12ARN |
| 13 | $Z = 0.238 \times A2M^r - 0.050 \times CXCL10 + 0.531 \times ENG^r + 0.023 \times IL8 + 0.320 \times SPP1^r$ | Z13ARN |
| 14 | $Z = 0.373 \times A2M^r + 0.389 \times (-IL6ST)^r + 0.020 \times IL8 + 0.309 \times SPP1^r + 0.105 \times TIMP1^r$ | Z14ARN |
| 15 | $Z = 0.412 \times A2M^r + 0.001 \times IHH + 0.413 \times (-IL6ST)^r + 0.027 \times IL8 + 0.327 \times SPP1^r$ | Z15ARN |
| 16 | $Z = 0.360 \times A2M^r - 0.047 \times CXCL10 + 0.025 \times IL8 + 0.332 \times S100A4 + 0.272 \times SPP1^r$ | Z16ARN |
| 17 | $Z = 0.399 \times A2M^r + 0.406 \times (-IL6ST)^r + 0.017 \times IL8 + 0.540 \times MMP7 + 0.328 \times SPP1^r$ | Z17ARN |
| 18 | $Z = 0.242 \times A2M^r - 0.094 \times CXCL11^r + 0.477 \times ENG^r + 0.016 \times IL8 + 0.323 \times SPP1^r$ | Z18ARN |
| 19 | $Z = 0.221 \times A2M^r + 0.371 \times ENG^r + 0.028 \times MMP9 + 0.316 \times SPP1^r$ | Z19ARN |
| 20 | $Z = 0.239 \times A2M^r - 0.029 \times CXCL10 + 0.489 \times ENG^r + 0.333 \times SPP1^r$ | Z20ARN |
| 21 | $Z = 0.303 \times A2M^r + 2.807 \times p14ARF^r - 0.033 \times CXCL10 + 0.040 \times MMP9 + 0.359 \times SPP1^r$ | Z21ARN |
| 22 | $Z = 0.406 \times A2M^r - 0.001 \times CXCL6 + 0.384 \times (-IL6ST)^r + 0.021 \times IL8 + 0.298 \times SPP1^r$ | Z22ARN |
| 23 | $Z = 0.313 \times A2M^r + 0.016 \times IL8 + 0.280 \times S100A4 + 0.272 \times SPP1^r$ | Z23ARN |
| 24 | $Z = 0.291 \times A2M^r + 0.072 \times ANGPT2 + 0.014 \times IL8 - 0.822 \times MMP7 + 0.361 \times SPP1^r$ | Z24ARN |
| 25 | $Z = 0.305 \times A2M^r + 3.153 \times p14ARF - 0.038 \times CXCL10 + 0.020 \times IL8 + 0.368 \times SPP1^r$ | Z25ARN |
| 26 | $Z = 0.256 \times A2M^r + 0.013 \times IL8 + 0.360 \times SPP1^r + 0.084 \times TIMP1^r$ | Z26ARN |
| 27 | $Z = 0.274 \times A2M^r + 2.545 \times p14ARF + 0.013 \times IL8 + 0.357 \times SPP1^r$ | Z27ARN |
| 28 | $Z = 0.298 \times A2M^r - 0.035 \times CXCL10 + 0.020 \times IL8 + 0.079 \times IRF9^r + 0.375 \times SPP1^r$ | Z28ARN |
| 29 | $Z = 0.015 \times IL8 - 0.047 \times MMP2^r + 0.340 \times SPP1^r + 0.297 \times VIM^r$ | Z29ARN |

TABLE 5

AUC for Z functions of Table 4, example of threshold PT (in fact, threshold maximizing the Youden's index $\delta$) for these functions, and associated values for Se, Spe, NPV, PPV

| No. of gene combination (see Table 3 above) | Name of function (see Table 4 above) | AUC | AUC, lower limit | AUC, upper limit | Selected threshold ($\delta$) | Se | Spe | NPV | PPV |
|---|---|---|---|---|---|---|---|---|---|
| 1 | Z1ARN | 0.8 | 0.72 | 0.862 | 0.561 | 75 | 72 | 84 | 60 |
| 2 | Z2ARN | 0.79 | 0.708 | 0.854 | 0.999 | 70 | 73 | 81 | 59 |
| 3 | Z3ARN | 0.788 | 0.706 | 0.853 | 0.68 | 70 | 74 | 81 | 60 |
| 4 | Z4ARN | 0.787 | 0.705 | 0.852 | −0.764 | 75 | 70 | 83 | 58 |
| 5 | Z5ARN | 0.787 | 0.704 | 0.851 | 0.941 | 70 | 72 | 81 | 58 |

TABLE 5-continued

AUC for Z functions of Table 4, example of threshold PT (in fact, threshold maximizing the Youden's index δ) for these functions, and associated values for Se, Spe, NPV, PPV

| No. of gene combination (see Table 3 above) | Name of function (see Table 4 above) | AUC | AUC, lower limit | AUC, upper limit | Selected threshold (δ) | Se | Spe | NPV | PPV |
|---|---|---|---|---|---|---|---|---|---|
| 6 | Z6ARN | 0.787 | 0.705 | 0.851 | 0.79 | 70 | 70 | 80 | 56 |
| 7 | Z7ARN | 0.786 | 0.703 | 0.851 | −0.605 | 75 | 70 | 83 | 57 |
| 8 | Z8ARN | 0.786 | 0.73 | 0.85 | 0.753 | 70 | 70 | 80 | 55 |
| 9 | Z9ARN | 0.786 | 0.703 | 0.85 | 0.874 | 71 | 70 | 81 | 56 |
| 10 | Z10ARN | 0.785 | 0.701 | 0.851 | −0.699 | 73 | 70 | 83 | 57 |
| 11 | Z11ARN | 0.785 | 0.701 | 0.85 | 0.82 | 71 | 70 | 81 | 56 |
| 12 | Z12ARN | 0.785 | 0.702 | 0.85 | 0.797 | 70 | 73 | 81 | 59 |
| 13 | Z13ARN | 0.784 | 0.702 | 0.848 | −0.301 | 75 | 70 | 83 | 57 |
| 14 | Z14ARN | 0.784 | 0.701 | 0.849 | 0.649 | 71 | 72 | 82 | 58 |
| 15 | Z15ARN | 0.784 | 0.702 | 0.849 | 0.88 | 70 | 70 | 80 | 55 |
| 16 | Z16ARN | 0.783 | 0.7 | 0.848 | 0.321 | 70 | 75 | 81 | 60 |
| 17 | Z17ARN | 0.783 | 0.701 | 0.848 | 0.838 | 70 | 70 | 80 | 56 |
| 18 | Z18ARN | 0.781 | 0.698 | 0.846 | −0.066 | 71 | 70 | 81 | 56 |
| 19 | Z19ARN | 0.779 | 0.694 | 0.845 | −0.222 | 73 | 70 | 83 | 57 |
| 20 | Z20ARN | 0.779 | 0.695 | 0.845 | −0.327 | 71 | 70 | 81 | 57 |
| 21 | Z21ARN | 0.778 | 0.692 | 0.845 | −0.162 | 73 | 70 | 83 | 57 |
| 22 | Z22ARN | 0.786 | 0.703 | 0.851 | 0.778 | 71 | 70 | 81 | 56 |
| 23 | Z23ARN | 0.777 | 0.692 | 0.844 | 0.236 | 73 | 70 | 83 | 57 |
| 24 | Z24ARN | 0.775 | 0.689 | 0.842 | −0.133 | 71 | 70 | 81 | 56 |
| 25 | Z25ARN | 0.775 | 0.691 | 0.842 | −0.181 | 70 | 70 | 80 | 55 |
| 26 | Z26ARN | 0.773 | 0.688 | 0.841 | −0.354 | 71 | 70 | 81 | 57 |
| 27 | Z27ARN | 0.771 | 0.685 | 0.839 | −0.132 | 71 | 71 | 82 | 58 |
| 28 | Z28ARN | 0.771 | 0.685 | 0.838 | −0.39 | 70 | 70 | 81 | 56 |
| 29 | Z29ARN | 0.759 | 0.671 | 0.829 | −1.202 | 71 | 70 | 81 | 56 |

TABLE 6

Examples of classification models (in fact, mROC models) combining levels of translation (proteins, in fact seric proteins)

| No. of gene combination (see Table 3 above) | Z function combining the levels of translation (seric protein) of the selected genes | Name of function |
|---|---|---|
| 16 | Z = 0.241 × A2M$^t$ + 0.137 × CXCL10$^t$ + 0.001 × IL8$^t$ + 0.062 × SPP1$^t$ + 0.226 × S100A4$^t$ | Z16prot |

TABLE 7

AUC for the Z function of Table 6, example of threshold PT (in fact, threshold maximizing the Youden's index δ) for this function, and associated values for Se, Spe, NPV, PPV (see Example 3a) below)

| No. of gene combination (see Table 3 above) | Name of function (see Table 6 above) | AUC | AUC, lower limit | AUC, upper limit | Selected threshold (δ) | Se | Spe | NPV | PPV |
|---|---|---|---|---|---|---|---|---|---|
| 16 | Z16PROT | 0.694 | 0.612 | 0.765 | 2.905 | 68 | 67 | 81 | 50 | uct (RNA) of that gene, i.e. the quantity of RNA of the gene concerned with respect to the total quantity of RNA initially contained in the sample, more particularly the Ct value which was measured for the transcripts of that gene and which has been normalized using the $2^{-\Delta Ct}$ method. If the symbol BMK (biomarker) is used to designate each of these variables in a generic manner, it may be considered that BMK=the value obtained for the RNA of this gene using the $2^{-\Delta Ct}$ method (see Example 1 below).

In Table 6 above, the samples from individuals that were used to allow a classification model to be constructed (Z function) were blood samples, and it was the level of translation (protein) of the selected genes which was measured. The measurement values were thus those obtained for samples containing the proteins of a biological sample which is susceptible of being obtained from a blood sample (for example, by separation and harvest of the serum fraction of that blood sample).

In Table 6 above, the name of each of the genes indicated as variables in a Z function (for the Z function of combination No. 16: A2M, CXCL10, IL8, SPP1 and S100A4) symbolises the measurement value for the translation product of that gene (protein product), i.e. the concentration of that translation product, more particularly the concentration of the protein coded by that gene measured in a biological In Table 4 above, the samples from individuals that were used to allow a classification model to be constructed (Z function) were samples of tissue or hepatic cells, and it was the level of RNA transcription of the selected genes which was measured. The measurement values were thus those obtained for samples containing RNAs from a biological sample susceptible of being obtained by HBP or hepatic cytopuncture (for example by extraction of RNAs from this biological sample).

In Table 4 above, the name of each of the genes indicated as variables in a Z function (for example, for the Z function of combination No. 1: A2M, CHI3L1, IL6ST, IL8 and SPP1) symbolises the measurement value for a transcription prodfluid of the patient, such as the serum. If the symbol BMK (biomarker) is used to designate each of these variables in a generic manner, it may be considered that BMK=the concentration obtained for the transcription product of that gene (see Example 3 below).

In Tables 4 and 6 above, the exponent t associated with a BMK value ("BMK$^t$") indicates a Box-Cox transformation (BMK$^t$=(BMK$^\lambda$-1)/$\lambda$); see Box and Cox, 1964.

Table 8 below indicates a list des genes, for which it is advised to normalize the measurement values for the assayed levels of transcription (RNA) (in fact, A2M, ENG, SPP1, VIM, IRF9, CXCL11, TIMP1, MMP2, IL6ST, TIMP1, COL1A1 AND MMP1), for example by a Box-Cox normalisation, and presents an example of the value of the Box-Cox parameter ($\lambda$) which can be used in the Z functions indicated in Table 4 above.

TABLE 8

List of genes for which it is advised to normalize the assayed measurement values (in particular, the measurements for the levels of RNA transcription, more particularly when these RNAs are susceptible of being obtained from a sample of tissue or hepatic cells), for example by a Box-Cox normalisation, and example of values for the Box-Cox parameter ($\lambda$) which can be used in the Z functions indicated in Table 4 above.

| Genes for which it is advised to normalize the value of the level of transcription (RNA) | Example of value for the Box-Cox parameter ($\lambda$) which can be used for the Z functions of Table 4 above |
|---|---|
| A2M | 0.33 |
| ENG | 0.08 |
| SPP1 | 0.12 |
| VIM | −0.23 |
| IRF9 | 0.17 |
| CXCL11 | 0.06 |
| TIMP1 | 0.02 |
| MMP2 | −0.03 |
| IL6ST | 0 |
| TIMP1 | 0.02 |
| COL1A1 | 0.24 |
| MMP1 | 0.02 |

Table 9 below indicates a list of genes for which it is advised to normalize the assayed measurement values for the levels of translation (protein) (in fact, A2M, CXCL10, IL8, SPP1 and S100A4), for example by a Box-Cox normalisation, and presents an example of a value for the Box-Cox parameter ($\lambda$) which can be used in the Z functions indicated in Table 6 above.

TABLE 9

List of genes for which it is advised to normalize the assayed measurement values (in particular, the measurements for the levels of protein translation, more particularly when these proteins are susceptible of being obtained from a sample of blood, serum or plasma), for example by a Box-Cox normalisation, and example of values for the Box-Cox parameter ($\lambda$) which can be used in the Z functions indicated in Table 6 above.

| Genes for which it is advised to normalize the value of the level of translation (protein) | Example of value for the Box-Cox parameter ($\lambda$) which can be used for the Z functions of Table 6 above |
|---|---|
| A2M | 0.46 |
| CXCL10 | 0.08 |
| IL8 | 0.05 |
| SPP1 | 0.43 |
| S100A4 | −0.15 |

In addition to the levels of expression of said selected genes, the means of the invention can also comprise a combination of one or more factors other than the levels of expression of said selected genes, such as:
  one or more clinical factors, such as:
    sex (female, F or male, M),
    age at the date of sampling (Age), for example, age at the date of HBP, age at the date of hepatic cytopuncture, age at the date of sampling blood, serum, plasma or urine,
    age of patient at the date of contamination,
    age of patient at the start of treatment,
    body mass index (BMI),
    insulin sensitivity index (HOMA),
    diabetes,
    alcohol consumption,
    level of steatosis,
    mode of contamination,
    Metavir activity,
  and/or
  one or more virological factors, such as:
    viral genotype,
    duration of infection,
    viral load measured for patient at treatment start date (viral load at D0),
    viral load measured for the patient at the date of sampling;
  and/or
  one or more biological factors other than the levels of expression of said selected genes, which may in particular be selected from the concentrations, contents or quantities of intracorporal proteins, concentrations, contents or quantities of intracorporal metabolites, concentrations, contents or quantities of elements occurring in blood, and assays representative of the quantity of circulating iron, such as:
    concentration of haptoglobin (Hapto),
    concentration of apolipoprotein A1 (ApoA1),
    total quantity of bilirubin (BLT),
    concentration of gamma glutamyl transpeptidase (GGT),
    concentration of aspartate aminotransferase (AST),
    concentration of alanine aminotransferase (ALT),
    platelet count (PLQ),
    quantity of prothrombin (TP),
    quantity of HDL cholesterol (Chol-HDL),
    total quantity of cholesterol,
    concentration of ferritin (Ferritin),
    level of glycaemia (glycaemia),
    concentration of peptide C,
    quantity of insulin (insulinaemia),
    concentration of triglycerides (TG),
    quantity of albumin,
    transferrin saturation (TSAT),
    concentration of alkaline phosphatase (ALP).

This or these other factors may be assayed for a sample with a nature which differs from that used to assay the levels of expression of said selected genes. As an example, the biological sample for assaying the levels of expression of said genes selected from said list of twenty-two genes of the invention may be a HBP or hepatic cytopuncture sample, and the biological sample for assaying the values of said other factors may be a sample of a biological fluid such as blood, plasma or serum or urine. Similarly, the nature of the assayed level of expression may be different; as an example, to assay the level of expression of said selected genes, it is possible to assay the levels of their transcription into RNA, while for those of said other factors which are biological factors, the assayed level of expression will generally be a protein concentration.

Advantageously, this or these other factors are or comprise one or more biological factors, from among:
the following clinical factors:
sex (female, F or male, M),
age at the date of sampling,
body mass index (BMI),
insulin sensitivity index (HOMA),
diabetes,
alcohol consumption,
level of steatosis,
and/or
the following virological factors:
viral genotype,
duration of infection,
and/or
the following biological factors:
concentration of haptoglobin (Hapto),
concentration of apolipoprotein A1 (ApoA1),
total quantity of bilirubin (BLT),
concentration of gamma glutamyl transpeptidase (GGT),
concentration of aspartate aminotransferase (AST),
concentration of alanine aminotransferase (ALT),
platelet count (PLQ),
quantity of prothrombin (TP),
total quantity of cholesterol,
quantity of HDL cholesterol (Chol-HDL),
concentration of ferritin (Ferritin),
level of glycaemia (glycaemia),
concentration of peptide C,
concentration of triglycerides (TG), The measurement of certain of these factors could sometimes be considered to be the measurement of the level of translation (protein concentration assay) of a gene other than a gene selected in accordance with the invention (for example ALT).

The number of genes the level of expression of which is measured and which are not genes selected in accordance with the application (for example the gene coding for ALT), is preferably a maximum of 18, more particularly 14 or fewer, more particularly 11 or fewer, more particularly 6 or fewer, more particularly 4 or 3 or 2, more particularly 1 or 0.

Advantageously, this or these other factors are or comprise one or more biological factors, in particular one or more factors from among the following biological factors:
concentration of gamma glutamyl transpeptidase (GGT),
concentration of alanine aminotransferase (ALT),
concentration of ferritin (Ferritin),
concentration of triglycerides (TG),
more particularly, one or more factors from among the following biological factors:
concentration of alanine aminotransferase (ALT),
concentration of triglycerides (TG).

Alternatively or in a complementary manner, this or these factors may more particularly be or comprise the clinical factor age at the date of sampling (Age).

Examples 2c), 2d) and 3b) below provide an illustration of such combinations.

The examples 2c), 2d) and 3b) below also provide examples of multivariate classification models (in fact, des mROC models) for combinations involving:
the levels of expression (measurement of RNA or of proteins) of genes selected from said list of twenty-two genes of the invention, as well as
biological factors other than the level of expression of genes selected from said list of twenty-two genes of the invention (in fact, several factors selected from concentration of triglycerides (TG), concentration of alanine aminotransferase (ALT), concentration of gamma glutamyl transpeptidase (GGT), concentration of ferritin), and,
optionally, a clinical factor (in fact, the clinical factor age at the date of sampling).

In accordance with one embodiment of the invention, said genes selected from said list of twenty-two genes of the invention are or comprise A2M, CXCL10, IL8, SPP1 and S100A4 (combination No. 16 in Table 3 above), and the combination of the value for their respective levels of expression (measurement of RNA or of proteins, in particular hepatic RNAs or seric proteins) is also combined with at least one or more biological factors other than the levels of expression of genes selected from said list of twenty-two genes of the invention, in particular with at least one or more biological factors from among:
concentration of gamma glutamyl transpeptidase (GGT),
concentration of alanine aminotransferase (ALT),
concentration of triglycerides (TG),
optionally, concentration of ferritin (Ferritin),
more particularly with at least one or more of these biological factors and in addition one or more clinical factors (such as age at the date of sampling).

The examples 2c) and 3b) below provide an illustration of such combinations.

In accordance with one embodiment of the invention, said genes selected from said list of twenty-two genes of the invention are or comprise A2M, CXCL10, IL8, SPP1 and VIM (combination No. 4 in Table 3 above), and the combination of the value for their respective levels of expression (more particularly, measurement of RNAs, in particular of hepatic RNAs) is also combined with at least one or more biological factors other than the levels of expression of genes selected from said list of twenty-two genes of the invention, in particular with at least one or more biological factors from among:
concentration of gamma glutamyl transpeptidase (GGT),
concentration of alanine aminotransferase (ALT),
concentration of triglycerides (TG),
concentration of ferritin (Ferritin).

Example 2d) below provides an illustration of such combinations.

Examples of multivariate classification models for such combinations comprise the Z linear functions (mROC models) presented in Tables 10 and 12 below (see also, Examples 2c), 3b) and 2d) below).

In Table 10 below, the samples from individuals used to construct the classification model (Z function) were tissue or hepatic cell samples, and the level of RNA transcription of the selected genes was that which was measured. As was the case for Table 4 above, the name of each of the genes indicated as the variables in a Z function (for example for the Z function of combination No. 16: A2M, CXCL10, IL8, SPP1 and S100A4) symbolises the measurement value for a transcription product (RNA) of that gene, i.e. the quantity of RNA of the gene concerned with respect to the total quantity of RNA initially contained in the sample, more particularly the value of Ct which was measured for the transcripts of that gene and which had been normalized using the $2^{-\Delta Ct}$ method.

In Table 12 below, the samples from individuals used to construct the classification model (Z function) were blood samples, and the level of translation (protein) of the selected genes was that which was measured. As was the case for Table 6 above, the name of each of the genes indicated as the variables in a Z function (for example for the Z function of combination No. 16: A2M, CXCL10, IL8, SPP1 and S100A4) symbolises the measurement value for a translation product of that gene (protein product), i.e. the concentration of that translation product, more particularly the concentration of the protein encoded by that gene assayed in a biological fluid of the patient, such as the serum. Tables 11 and 13 below present examples for the values for the parameter, lambda, for the Box-Cox transformations for use for the Z functions of Tables 10 and 12, give the AUC for these Z functions, and indicate an example of the value of the PT threshold (in fact, the threshold maximizing the Youden's index, δ), as well as the associated values of Se, Sp, NPV and PPV.

Hence, in accordance with one embodiment of the invention, the genes selected in step i) are the genes of one of said combination Nos. 1 to 29, for example the genes for combination No. 16 or 4, in step i), the level at which each of these selected genes is transcribed or translated is measured, the value of several other factors other than the levels of expression of the genes selected from said list of twenty-two genes of the invention is determined, including at least one of the following factors:

concentration of alanine aminotransferase (ALT), concentration of triglycerides (TG), optionally, concentration of gamma glutamyl transpeptidase (GGT) and/or concentration of ferritin (Ferritin) and/or age at the date of sampling, the values for the other factors determined thereby and the measurement values obtained in step i) then being combined together in step ii) in order to be compared with their values or with the distribution of their values in said reference cohorts.

TABLE 10

Combination of selected genes in accordance with the invention (measurement of their levels of transcription to RNA), also combined with other factors

| Selected genes and nature of level of expression assayed for these genes | | Other factors | Example of multivariate classification model (mROC model) | Name of function |
|---|---|---|---|---|
| combination No. 16 of Table 3 above | RNA (&) | Age<br>GGT (protein)<br>ALT (protein)<br>TG (protein)<br>Ferritin (protein) | $Z = 0.272 \times A2M^t - 0.032 \times CXCL10 + 0.058 \times IL8 + 0.419 \times SPP1^t + 0.012 \times S100A4^t + 0.025 \times Age^t + 0.566 \times TG^t + 3.874 \times ALT^t - 0.039 \times Ferritin^t$ | Z16ARNsupp |
| combination No. 4 of Table 3 above | RNA (&) | GGT (protein)<br>ALT (protein)<br>TG (protein)<br>Ferritin (protein) | $Z = 0.315 \times A2M^t - 0.043 \times CXCL10 + 0.058 \times IL8 + 0.383 \times SPP1^t + 0.064 \times VIM^t + 0.56 \times TG^t + 3.657 \times ALT^t + 0.188 \times GGT^t - 0.05 \times Ferritin^t$ | Z4ARNsupp |

(&): more particularly, RNAs contained in a sample of tissue or hepatic cells
Age = age at the date of sampling;
GGT = concentration of gamma glutamyl transpeptidase in serum;
ALT = concentration of alanine aminotransferase in serum;
TG = concentration of triglycerides (TG) in serum;
Ferritin = concentration of ferritin in serum.

TABLE 11

For the functions of Table 10, example of value of the parameter lambda, AUC values, examples of PT thresholds (in fact, threshold maximizing the Youden's index δ) for these functions, and associated values for Se, Spe, NPV, PPV

| Name of function | Example of value of the parameter lambda (*) | AUC | AUC, lower limit | AUC, upper limit | Threshold (δ) | Se | Spe | NPV | PPV |
|---|---|---|---|---|---|---|---|---|---|
| Z16ARNsupp (see Table 10) | 0.21 for A2M<br>0.04 for SPP1<br>0.48 for S100A4<br>0.79 for Age<br>−0.22 for TG<br>−0.41 for ALT<br>0.15 for Ferritin | 0.840 | 0.760 | 0.897 | 8.014 | 72 | 82 | 85 | 67 |
| Z4ARNsupp (see Table 10) | 0.21 for A2M<br>0.04 for SPP1<br>−0.26 for VIM<br>−0.22 for TG<br>−0.41 for ALT<br>−0.12 for GGT<br>0.15 for Ferritin | 0.841 | 0.764 | 0.896 | 7.016 | 80 | 71 | 88 | 59 |

(*) lambda, parameter for Box-Cox transformations [$BMK^t = (BMK^\lambda - 1)/\lambda$]

TABLE 12

Combination of selected genes in accordance with the invention (measurement of their levels of translation into proteins), also combined with factors

| Selected genes and nature of level of expression assayed for these genes | Other factors | Example of multivariate classification model (mROC model) | Name of function |
|---|---|---|---|
| combination No. 16 of Table 3 above | Proteins (§) Age GGT (protein) ALT (protein) TG (protein) | $Z = 0.2 \times A2M^t + 0.05 \times CXCL10^t - 0.026 \times IL8^t + 0.051 \times SPP1^t + 0.204 \times S100A4^t + 0.020 \times Age^t + 0.266 \times TG^t + 3.354 \times ALT^t + 0.141 \times GGT^t$ | Z16PROTsupp |

(§): more particularly, proteins contained in a blood sample, in fact in the seric portion of that sample
Age = age at the date of sampling;
GGT = concentration of gamma glutamyl transpeptidase in the serum;
ALT = concentration of alanine aminotransferase in the serum;
TG = concentration of triglycerides (TG) in the serum;
Ferritin = concentration of ferritin in the serum.

TABLE 13

For the function of Table 12, example of lambda parameters, AUC value, example of threshold PT (in fact, threshold maximizing the Youden's index δ) for this function, and associated values for Se, Spe, NPV, PPV

| Name of function | Example of value of the parameter lambda (*) | AUC | AUC, lower limit | AUC, upper limit | Threshold (δ) | Se | Spe | NPV | PPV |
|---|---|---|---|---|---|---|---|---|---|
| Z16PROTsupp (see Table 12) | 0.46 for A2M 0.08 for CXCL10 0.05 for IL8 0.43 for SPP1 −0.15 for S100A4 0.9 for Age −0.27 for TG −0.13 for GGT −0.47 for ALT | 0.743 | 0.666 | 0.809 | 8.792 | 67 | 72 | 83 | 52 |

(*) lambda, parameter for Box-Cox transformations $[BMK^t = (BMK^\lambda - 1)/\lambda]$ The factor "Metavir activity" is a semi-quantitative evaluation of the activity of the hepatitis taking piecemeal necrosis and lobular necrosis into account, for example using the method described by Bedossa et al. 1996, which provides a resulting score of 0 to 3:
A0: no activity,
A1: minimal activity,
A2: moderate activity,
A3: severe activity.

The "steatosis" factor is a semi-quantitative evaluation of the percentage of hepatocytes containing steatosis vacuoles during an anatomo-pathologic study of a biopsy, for example using the following score system:
Grade 0: <1% of hepatocytes damaged,
Grade 1: 1-33% of hepatocytes damaged,
Grade 2: 33-66% of hepatocytes damaged,
Grade 3: >66% of hepatocytes damaged.

This or these other factors may be associated, by way of co-variables, with the combination of the levels of expression of said selected genes. The values for these factors and levels of expression may, for example, be combined into a multivariate classification model combining both the parameters relating to the levels of expression of said selected genes and the parameters relating to this or these factors (see examples 2c), 2d) and 3b) below).

In accordance with a complementary aspect of the invention, the application relates to products or reagents for the detection and/or determination and/or measurement of the levels of expression of said selected genes, and to manufactured articles, compositions, pharmaceutical compositions, kits, tubes or solid supports comprising such reagents, as well as to computer systems (in particular, computer program product and computer device), which are specially adapted to carrying out a method of the invention.

The application is in particular relative to a reagent which specifically detects a transcription product (RNA) of one of said genes selected from said list of twenty-two genes of the invention, or a translation product of one of said genes selected from said list of twenty-two genes of the invention (protein, or post-translational form of this protein, such as a specific fragment of this protein).

In particular, the application pertains to reagents which specifically detect each of the transcription products (RNA) of said genes selected from said list of twenty-two genes of the invention, or each of the translation products of said genes selected from said list of twenty-two genes of the invention (protein, or post-translational form of this protein, as a specific fragment of this protein).

Advantageously, a set of such reagents is formed which detects each of said transcription products of said selected genes and/or which detects each of said translation products of said genes selected from said list of twenty-two genes of the invention, i.e. a set of reagents which specifically detects at least one expression product for each of these genes.

Preferably, said reagents not only specifically detect a transcription or translation product, but can also quantify it.

In particular, the application pertains to a manufactured article comprising said reagents as a combination product (or combined form, or combined preparation), in particular for their simultaneous, separate or sequential use. This manufactured article may, for example, be in the form of a set of reagents, or a kit.

Clearly, the characteristics of combinations of selected genes described above and those illustrated below are applicable to the reagents of the invention mutatis mutandis.

Said reagents may, for example, hybridize specifically to the RNA of said selected genes and/or to the cDNA corresponding to these RNAs (under at least stringent hybridization conditions), or bind specifically to proteins encoded by said selected genes (or to specific fragments of these proteins), for example in an antigen-antibody type reaction.

At least stringent hybridization conditions are known to the skilled person. The conditions may, for example, be as follows:

for filter hybridization: in 5×SSC, 2% sodium dodecyl sulphate (SDS), 100 micrograms/mL single strand DNA at 55-65° C. for 8 hours, and washing in 0.2×SSC and 0.2% SDS at 60-65° C. for thirty minutes;

for a hybridization by PCR: the PCR conditions indicated in Example 1 below.

Said reagents of the invention may in particular be:

nucleic acids (DNA, RNA, mRNA, cDNA), including oligonucleotide aptamers, optionally tagged to allow them to be detected, in particular with fluorescent tags which are well known to the skilled person, or protein ligands such as proteins, polypeptides or peptides, for example aptamers, and/or antibodies or fragments of antibodies.

The nucleic acids of the invention may, for example, be primers and/or probes (see SEQ ID NO: 1 to 44 in Table 17 below), in particular pairs of primers (see the pairs of primers indicated in Table 17 below). For each of said genes selected from said list of twenty-two genes of the invention, the skilled person can construct a pair of primers and/or a probe which specifically hybridizes to this gene. A manufactured article of the invention may thus comprise the number of primers and/or probes necessary for the detection of the RNA or cDNA of each of said selected genes.

The sequence of nucleic acids of the invention may, for example, be constituted by 9 to 40 nucleotides, more particularly 10 to 30 nucleotides, more particularly 14 to 29 nucleotides, more particularly 19 to 24 nucleotides.

The primer sequences of one pair may, for example, be the sequences of a fragment of the sequence of one of said selected genes and a fragment of its complementary sequence (see Table 2 indicating the accession numbers of the sequences for these genes). One and/or the other of these two primer sequences might not be strictly identical to the sequence of a gene fragment or its complementary sequence; one and/or the other of these two primer sequences may:

be derived from one or more nucleotide substitutions and/or additions and/or deletions, more particularly one or more nucleotide substitutions, and/or have a sequence identity of at least 80%, or at least 85%, or at least 90%, or at least 95% with the sequence for this fragment or its complementary sequence (identity calculated over the longest of the two aligned sequences–optimal alignment), provided that the resulting pair of primers has conserved the capacity to specifically hybridize to one of said selected genes.

A primer pair of the invention advantageously has a delta Tm of approximately 1° C. or less. In one embodiment of the invention, a primer pair of the invention targets an approximately 70 to 120 bp amplicon (i.e. the sense primer and the anti-sense primer hybridize at such positions on the target nucleic acid that the amplicon produced by elongation of these hybridized primers has a length of approximately 70 to 120 bp).

Examples of such primers and primer pairs are presented in Table 17 below (SEQ ID NO: 1 to 44, forming 22 primer pairs).

The sequence for a probe of the invention may, for example, be:

the sequence for a fragment of the sequence of one of said selected genes (see Table 2 indicating the accession numbers for sequences for these genes), said fragment hybridizing specifically to the sequence for that gene;

a sequence:

which derives from the sequence for such a fragment by one or more nucleotide substitutions and/or additions and/or deletions, more particularly by one or more nucleotide substitutions, and/or a sequence which has a sequence identity of at least 80%, or at least 85%, or at least 90%, or at least 95% with the sequence for this fragment or its complementary sequence (identity calculated for the longest of the two aligned sequences–optimal alignment), but which has conserved the capacity to hybridize specifically to one of said selected genes;

and/or a complementary sequence of such sequences.

A probe of the invention may in particular be a probe for real time amplification, intended for use with a primer pair in accordance with the invention. Alternatively, detection by real time PCR may use molecules known as intercalating (for example; SYB green) which have the ability of interposing themselves into double stranded structures.

The ligands of the invention, which bind specifically to proteins encoded by the genes selected from said list of twenty-two genes of the invention (or to specific fragments of these proteins) may, for example, be proteins, polypeptides or peptides, for example aptamers or antibodies or antibody fragments.

The skilled person can produce such a ligand for each of said selected genes.

The antibodies may, for example, be produced by immunization of a non-human mammal (such as a rabbit) with a protein encoded by said selected gene or with an antigenic fragment of such a protein, optionally associated or coupled with an immunization adjuvant (such as a Freund's adjuvant or KLH—keyhole limpet haemocyanin), for example by intraperitoneal or subcutaneous injection, and by collecting the antibodies obtained thereby in the serum of said mammal.

Monoclonal antibodies may be produced using a lymphocyte hybridization technique (hybridomas), for example using the technique by Köhler and Milstein 1975 (see also U.S. Pat. No. 4,376,110), the human B cell hybridoma technique (Kosbor et al. 1983; Cole et al. 1983), or the technique for immortalizing lymphocytes with the aid of the Epstein-Barr virus—EBV—(Cole et al. 1985). Examples of such antibodies are IgG, IgM, IgE, IgA, IgD or any sub-class of these immunoglobulins.

Antibodies modified by genetic engineering may be produced, such as recombinant antibodies or chimeras, humanized by grafting one or more CDRs (Complementary Determining Region).

The antibodies used in the invention may be fragments of antibodies or artificial derivatives of such fragments, provided that these fragments or derivatives have said specific binding property. Such fragments may, for example, be Fab, F(ab')2, Fv, Fab/c or scFv (single chain fragment variable) fragments.

Examples of antibodies are given in Table 14 below.

TABLE 14

Examples of specific antibodies

| Encoding gene | Antibody | Example of supplier | Catalogue reference of product |
|---|---|---|---|
| A2M | human anti-alpha 2 macroglobulin polyclonal antibody from goat, 100 μg | R&D systems 77, boulevard Vauban 59041 Lille Cedex France | AF1938 |
| SPP1 | human anti-osteopontin polyclonal antibody from goat, 100 μg | R&D systems | AF1433 |
| VIM | Polyclonal antibody from rabbit anti-vimentine, 1 mL (0.2 mg/mL) | Abcam 24, rue Louis Blanc 75010 Paris; France | ab15248-1 |
| p14ARF transcript No. 4 of gene CDKN2A | anti-CDKN2A/p14ARF polyclonal antibody from rabbit, 100 μL (1 mg/mL) | Abcam | ab53031-100 |
| CXCL10 | human anti-CXCL10/IP-10 polyclonal antibody (IgG from goat) | R&D systems | AB-266-PB |
| CXCL11 | human anti-CXCL11/I-TAC monoclonal antibody (clone 87328) (mouse IgG2A) | R&D systems | MAB672 |
| ENG | anti-ENG monoclonal antibody produced in the mouse (clone 4C11) | Sigma-Aldrich | WH0002022M1 |
| IL8 | anti-IL8 monoclonal antibody produced in the mouse (clone 6G4) | Sigma-Aldrich | WH0003576M5 |
| IRF9 | anti-transcription factor IRF9 antibody | Abcam | ab56677 |
| MMP2 | anti-MMP2 antibody [EP1329Y] | Abcam | ab51127 |
| MMP9 | anti-MMP9 antibody | Abcam | ab7299 |
| S100A4 | anti-S100A4 polyclonal antibody from rabbit, 250 μL (0.72 mg/mL) | Abcam | ab27957-250 |
| TIMP1 | anti-TIMP1 antibody | Abcam | ab77847 |
| ANGPT2 | human anti-angiopoietin 2 monoclonal antibody (clone 180102), (mouse IgG2B) | R&D systems | MAB0983 |
| IL6ST | human anti-gp130 monoclonal antibody (clone 29104), (mouse IgG1) | R&D systems | MAB2281 |
| CXCL1 | human anti-CXCL1/GRO alpha monoclonal antibody (mouse IgG2B) | R&D systems | MAB275 |
| COL1A1 | anti-COL1A1 polyclonal antibody produced in the rabbit | Sigma-Aldrich | HPA011795 |
| IHH | anti-IHH polyclonal antibody from rabbit | Abcam | ab39634 |
| CHI3L1 | anti-CHI3L1 polyclonal antibody produced in the rabbit | Sigma-Aldrich | AV51929 |
| MMP1 | human anti-Pro-MMP1 monoclonal antibody (clone 36660), (mouse IgG1) | R&D systems | MAB900 |
| MMP7 | human anti-Pro-MMP7 monoclonal antibody (clone 6A4), (mouse IgG1) | R&D systems | MAB907 |
| CXCL6 | human anti-CXCL6/GCP2 monoclonal antibody (clone 60910), (mouse IgG1) | R&D systems | MAB333 |

Other examples of means for measuring the levels of transcription of selected genes (A2M, CXCL10, CXCL8, SPP1 and S100A4) are also presented in Table 29 below (immunoassay kits).

Said reagents may also comprise a tag for their detection (for example a fluorophore).

Said reagents may be in the form of composition(s), pharmaceutical composition(s), for example in one or more tube(s) or in (a) well(s) of a nucleic acid amplification plate.

Said reagents may be as a mixture, or in distinct forms, or physically separated from each other.

Said reagents may be fixed to a solid support, for example a support formed from a polymer, from plastic, in particular polystyrene, from glass or from silicon.

Said reagents may be directly or indirectly attached to said solid support, for example via a binding agent or capture agent which is attached to the solid support. This binding or capture agent may comprise a portion fixed to said solid support and a portion which comprises a ligand which binds specifically to one of said selected genes. Such a ligand may, for example, be an antibody, a monoclonal antibody, in particular a human antibody such as a IgG, IgM or IgA, or a fragment of an antibody of this type which has conserved the binding specificity.

Said solid support may, for example, be a plastic plate, in particular formed from polystyrene, comprising a plurality of analytical wells, such as a protein titre or microtitre plate, for example an ELISA plate.

Said solid support may also be formed by magnetic or non-magnetic microbeads, for microtitration, for example using the technique described by Luminex.

Said solid support may, for example, be a nucleic acid, protein or peptide chip, for example a plastic, glass or silicon chip.

Said reagents do not have to be fixed to a solid support and may, for example, be contained in a solution such as a buffer, for example to store them until use. More particularly, the reagents may be nucleic acids which are not bound to a solid support the nucleotide sequence of which is adapted to specific amplification (the case of primers or primer pairs) and/or to specific hybridization (in the case of probes) of the transcription product (RNA) of one of said genes selected from said list of twenty-two genes of the invention.

In addition to reagents which detect the transcription or translation products of mammalian genes, more particularly human genes, and in particular genes selected from said list of twenty-two genes of the invention, a manufactured article in accordance with the application may optionally comprise other reagents, for example reagents that can be used to measure or determine one or more virological factors and/or one or more clinical factors.

As an example, an article manufactured in accordance with the application may comprise reagents which specifically detect one or more hepatitis viruses, and/or its or their genotype.

In one embodiment, the application pertains to a manufactured article comprising reagents in a combined preparation for their simultaneous, separate or sequential use, said reagents being constituted by:
  reagents which specifically detect (preferably, which specifically detect and can be used for quantification) each of the transcription or translation products of 3 to 40 mammalian genes, more particularly 3 to 40 human genes, (for example, by specifically hybridizing to the RNA of these genes and/or to the cDNA obtained by reverse transcription of these RNA, or by specifically binding to proteins encoded by these genes), said 3 to 40 mammalian genes, or, if appropriate, said 3 to 40 human genes, comprising said genes selected from said list of twenty-two genes of the invention,
and
  optionally, reagents which specifically detect (preferably which specifically detect and can be used for quantification) a hepatitis virus and/or the genotype of a hepatitis virus.

In this manufactured article, the number of mammalian genes, more particularly human genes the transcription or translation products of which may be detected, is 3 to 40, more particularly 3 to 36, more particularly 3 to 33, more particularly 3 to 28, more particularly 3 to 26, more particularly 3 to 25, more particularly 3 to 24, more particularly 3 to 23, more particularly 3 to 22, more particularly 3 to 20, more particularly 3 to 21, more particularly 3 to 20, more particularly 3 to 19, more particularly 3 to 18, more particularly 3 to 17, more particularly 3 to 16, more particularly 3 to 15, more particularly 3 to 14, more particularly 3 to 13, more particularly 3 to 12, more particularly 3 to 11, more particularly 3 to 10, more particularly 3 to 9, more particularly 3 to 8, more particularly 3 to 7, more particularly 3 to 6, more particularly 3 to 5, for example 3, 4 or 5, in particular 4 or 5.

The mammalian genes, more particularly the human genes, the transcription or translation products of which may be detected by the reagents contained in the manufactured article of the application comprise said genes selected from said list of twenty-two genes of the invention, and optionally other genes, which are not the genes selected from said list of twenty-two genes of the invention, but for which the expression product, more particularly of translation, may be of interest, such as the genes listed here as "other biological factors" (for example, the gene coding for alanine-amino transferase).

The number of genes selected from said list of twenty-two genes of the invention is a maximum of 22 genes (SPP1, and at least one gene from among A2M and VIM, and at least one gene from among IL8, CXCL10 and ENG, and optionally, at least one gene from among the list of sixteen genes). Advantageously, this number may be less than 22: this number may more particularly be 3 to 10, more particularly 3 to 9, more particularly 3 to 8, more particularly 3 to 7, more particularly 3 to 6, more particularly 3 to 5, for example 3, 4 or 5, in particular 4 or 5.

In the manufactured article of the application, the number of reagents which specifically detect the expression product of mammalian genes (more particularly human genes) which are not genes selected from said list of twenty-two genes of the invention (for example a reagent specifically detecting ALT) is preferably a maximum of 18, more particularly 14 or fewer, more particularly 11 or fewer, more particularly 6 or fewer, more particularly 4 or 3 or 2, more particularly 1 or 0.

Said manufactured article may thus, for example, be:
  one or more tubes,
  a kit, in particular a kit comprising one or more tubes,
  a solid support, for example, formed from plastic, polystyrene, glass, silicon or polymer or comprising a magnetic material such as iron oxide, such as:
    a plate formed from plastic comprising a plurality of analysis wells, such as
      a nucleic acid amplification plate comprising wells for receiving a biological sample and a reaction mixture for nucleic acid amplification,
      a titration or microtitration plate, more particularly an ELISA plate,
    magnetic microbeads (for example microbeads formed from iron oxide and coated with a polymer to which the proteins or polypeptides can adhere or be attached by chemical coupling);
    a nucleic acid, protein, polypeptide or peptide chip.

Optionally, the manufactured article of the invention further comprises instructions (for example, an instruction sheet) for measuring the level of expression of said selected genes on a biological sample collected or obtained from said subject, more particularly to carry out a method of the invention.

Said manufactured article may further comprise one or more of the following elements:
- an instrument for removing said sample, in particular:
  - a needle and/or a syringe, more particularly a needle and/or a syringe for taking a sample of an intracorporal liquid such as blood, and/or
  - a needle adapted for hepatic cytopuncture, for example a needle with a diameter of 18 to 22G), and/or
  - a needle and/or a catheter and/or a biopsy gun adapted for HBP;
- a computer program product or software product, in particular a computer program product or statistical analysis software, for example a computer program product of the invention as described below;
- RNA extraction reagents;
- a reverse transcriptase;
- a polymerase, for example a Taq polymerase;
- nucleotides (dNTP).

In particular, the application pertains to said manufactured article or to said reagents for their use in a method for detecting or diagnosing a hepatopathy which comprises liver tissue damage, more particularly a hepatic fibrosis, more particularly to determine the hepatic fibrosis score of a subject, advantageously to determine whether the hepatic fibrosis of a subject has a Metavir fibrosis score of at most F1 or indeed at least F2.

The application pertains in particular to said manufactured article or to said reagents for their use in a method of the invention.

In particular, this use may comprise:
- taking a biological sample from said subject, in particular by inserting a needle or catheter into the body of said subject, and
- using said reagents in said method on this biological sample, or on a sample comprising nucleic acids and/or proteins and/or polypeptides and/or peptides extracted or purified from said biological sample, or on a sample comprising cDNAs which are susceptible of having been obtained by reverse transcription of said nucleic acids.

This use may, for example, comprise:
- taking a biological sample of said subject, optionally transformed by:
  - extraction or purification of RNAs of said removed sample and optionally by reverse transcription of the extracted RNAs, or by
  - extraction or purification of its proteins from said sample, and
- using said reagents of the invention on this optionally transformed biological sample.

Said biological sample may be taken by inserting a sampling instrument, in particular by inserting a needle or a catheter, into the body of said subject.

The sampling instrument is primarily inserted in order to remove intracorporal fluid from said subject (such as blood, for example) and/or a portion of hepatic tissue from said subject (for example by HBP) and/or hepatic cells from said subject (for example by hepatic cytopuncture).

This instrument may thus be inserted, for example:
- into a vein, an artery or a blood vessel of said subject to remove blood from said subject; and/or
- into the liver of said subject, in order to take a sample of hepatic parenchyma, i.e. to carry out a hepatic biopsy puncture (HBP), for example transjugularly or transparietally; and/or
- through the skin to the liver of said subject, so as to carry out a hepatic cytopuncture.

The application pertains in particular to said manufactured article or to said reagents for their use in a method for the treatment of a hepatopathy which comprises liver tissue damage, more particularly a hepatic fibrosis.

This use may in particular comprise
- using said reagents in a method of the invention in order to determine the hepatic fibrosis score of said subject, and
- the fact of administering to said subject a treatment aimed at blocking the progress of the hepatic fibrosis, such as standard or pegylated interferon, in a monotherapy or in a polytherapy combined with ribavirin, if the subject has a hepatic fibrosis score which, when expressed in accordance with the Metavir system, is at least F2.

This use may, for example, comprise:
- using said reagents of the invention on a biological sample which has been taken from said subject, and which optionally has been transformed, for example:
  - by extraction and/or purification of the RNAs of said sample and, optionally, by reverse transcription of the extracted RNAs, or
  - by extraction and/or purification of proteins and/or polypeptides and/or peptides of said sample which has been taken,
- for detecting or diagnosing a hepatopathy which comprises a hepatic fibrosis, more particularly for determining the hepatic fibrosis score of said subject, advantageously for determining whether the hepatic fibrosis of said subject has a Metavir fibrosis score:
  - of at most F1 (i.e. a hepatic fibrosis without septa), or
  - at least F2 (i.e. a hepatic fibrosis with septa),
  - optionally, in the case of a hepatopathy involving a hepatitis virus, in particular a HCV and/or a HBV and/or a HDV, in particular at least a HCV, determining the genotype of that virus, and
- the fact of administering a treatment aimed at blocking or slowing down the progress of the hepatic fibrosis if the stabbing guide has a Metavir fibrosis score of at least F2.

This method may in addition comprise the fact of not administering this treatment if or while this score is at most F1.

Said treatment may, for example, be a treatment with standard interferon or pegylated interferon in a monotherapy or in polytherapy combining one or more other active principles, in particular ribavirin and/or a viral protease inhibitor and/or a viral polymerase inhibitor (for example in therapeutic combination, in particular as a bitherapy or tritherapy).

This treatment may, for example, be:
- pegylated alpha-2b interferon (such as PEG-INTRON®; Schering Plough Corporation; Kenilworth, N.J.; U.S.A.) in a dose of approximately 1.5 g/kg/week, and ribavirin (REBETOL®; Schering Plough Corporation; Kenilworth, N.J.; U.S.A.) in a dose of approximately 800 to 1200 mg/kg/day (if the hepatopathy involves a HCV with genotype 2 or 3, a dose of approximately 800 mg/kg/day is generally recommended), or
- pegylated alpha-2a interferon (PEGASYS®; Roche Corporation; F. Hoffmann-La Roche Ltd.; Basel, Switzerland) in a concentration of 180 g/kg/week, and ribavirin (COPEGUS®; Roche Corporation; F. Hoffmann-La Roche Ltd.; Basel, Switzerland) in a concentration of 1000 to 1200 mg/kg/day.

The treatment period may, for example, be at least 24 weeks, for example 24 weeks for a HCV hepatopathy with genotype 2 or 3, or 48 weeks for a HCV hepatopathy with genotype 4 or 5, or for a patient who does not respond to treatment after 24 weeks have passed.

The application also pertains to a drug or drug combination for the treatment of a hepatopathy comprising liver tissue damage, more particularly a hepatic fibrosis (such as standard interferon or pegylated interferon, in a monotherapy or polytherapy combining one or more other active principles, in particular ribavirin) for its use in the treatment method of the invention.

In the application, the term "hepatopathy" should be given its usual meaning, namely liver damage, more particularly liver tissue damage, more particularly lesions of the liver, in particular a hepatic fibrosis.

More particularly, the invention is directed towards chronic hepatopathies (chronic attacks of the liver of 6 or more months).

Various diseases cause and/or result in lesions of the liver, such as a hepatic fibrosis. Particular examples which may be cited are:
  chronic viral hepatitis (in particular the chronic hepatitis B, chronic hepatitis C, chronic hepatitis D,
  steatoses and steato-hepatites (associated with metabolic syndrome or obesity or diabetes),
  alcoholic hepatitis,
  genetic haematochromatosis and secondary iron overload,
  auto-immune diseases,
  biliary diseases (primary biliary cirrhosis and primary sclerosing cholangitis),
  drug or toxic substance intoxication,
  metabolic diseases.

The invention is more particularly suited to viral hepatites, in particular to hepatitis C viruses (HCV) and/or B viruses (HBV) and/or D viruses (HDV), in particular to at least HCV (and optionally HBV and/or HDV).

The application also pertains to a computer program product to be stored in a memory of a processing unit or on a removable memory support for cooperation with a reader of said processing unit. The computer program product of the invention comprises instructions for carrying out a method of the invention, in particular for carrying out a statistical analysis adapted to carrying out a method of the invention (in particular adapted for the multivariate statistical analysis of the measurements, and more particularly the levels of expression of said selected genes) and/or for the construction of a multivariate classification model adapted to carrying out a method in accordance with the invention.

The application also pertains to a computer unit, a computer device, or computer, comprising a processing unit with the following stored or recorded in its memory:
  a computer program product of the invention, and, optionally,
  measurements, or measurement values, of the levels of expression (transcription and/or translation) of said selected genes.

The term "comprising", which is synonymous with "including" or "containing", is an open term and does not exclude the presence of one or more additional element(s), ingredient(s) or step(s) of the method which are not explicitly indicated, while the term "consisting" or "constituted" is a closed term which excludes the presence of any other additional element, step or ingredient which is not explicitly disclosed. The term "essentially consisting" or "essentially constituted" is a partially open term which does not exclude the presence of one or more additional element(s), ingredient(s) or step(s) provided that this (these) additional element(s), ingredient(s) or step(s) do not materially affect the basic properties of the invention.

As a consequence, the term "comprising" (or "comprise(s)") includes the terms "consisting", "constituted" as well as the terms "essentially consisting" and "essentially constituted by".

With the aim of facilitating reading of the application, the description has been separated into various paragraphs, sections and embodiments. It should not be assumed that these separations disconnect the substance of one paragraph, section or embodiment from that of another paragraph, section or embodiment. On the contrary, the description encompasses all possible combinations of the various paragraphs, sections, phrases and embodiments which it contains.

The content of the bibliographic references cited in the application is specifically incorporated into the content of the application by reference.

The following examples are given purely by way of illustration. They do not in any way limit the invention.

EXAMPLES

Example 1

Construction of Classification Models

1. Populations and Patients, Measurement of Hepatic Fibrosis Score, Measurement of Level of Gene Expression The liver biopsies were carried out using a cohort of adult patients monitored at the Hôpital Beaujon (Clichy, France), presenting with a chronic hepatitis Due to infection with hepatitis C virus (HCV). The biopsies were immediately stored at −80° C. in order to extract total RNA, and treated with paraffin for the histological studies.

The study was approved by the local Ethics Committee in accordance with the Helsinki Declaration and all of the patients gave their informed written consent. The hepatic biopsy punctures were carried out in accordance with good clinical practice and the histological studies were interpreted by an anatomo-pathologist using the activity and fibrosis score (Metavir score).

Presentation of Patients

The clinical diagnosis of infection with the hepatitis C virus of the selected patients was established on the basis of the detection of antibodies directed against HCV proteins and the detection of circulating HCV RNA.

The serology of the HCV to be detected was carried out using the "VERSANT® HCV-RNA 3.0 (bDNA) ASSAY" HCV RNA quantification test from Siemens Healthcare Diagnostics (quantification limit=615-7 690 000 IU/mL).

The patients were patients infected with hepatitis C virus. In order to establish a homogeneous cohort which was entirely representative of the exemplified pathology, patients susceptible of presenting chronic hepatic diseases of origins other than the hepatitis C virus (such as a chronic hepatic disease due to an infection with hepatitis B virus) were excluded from the study.

Other exclusion criteria were also applied, namely excessive alcohol consumption, haemochromatosis, auto-immune hepatitis, Wilson's disease, α-1 antitrypsin deficiency, primary sclerosing cholangitis, primary biliary cirrhosis or subsequent anti-HCV treatment. Patients who had already undergone an antiviral treatment in the context of their chronic hepatitis C were also excluded from the study.

The stage of the hepatic fibrosis was determined by an anatomo-pathologic examination of a sample of hepatic tissue (hepatic biopsy puncture, HBP). This examination was carried out by means of two independent readings by a qualified anatomo-pathologist. The stage of hepatic fibrosis was defined in accordance with the Metavir classification as well as using the Ishak classification (see Table 1 above for the correlation between the two score systems).

A serum sample was taken for each patient included in the study in a period of ±6 months from the biopsy date.

Two hundred and forty-four patients were selected on the basis of their hepatic fibrosis stage determined using the Metavir and Ishak classifications. The two hundred and forty four patients selected had a Metavir fibrosis score of F1 or F2, and/or a Ishak fibrosis score of F1/F2 or F3.

Table 15 below presents the clinical, biological and virological data of the patients selected in this manner.

TABLE 15

| Clinical, biological and virological data | Patients | F1 patients | F2 patients |
|---|---|---|---|
| Cohort (n) | 244 | 162 | 82 |
| male (%)/female (%) | 114 (47)/130(53) | 69(43)/93(57) | 45(55)/37(45) |
| Age | | | |
| mean ± SD | 50.2 ± 11.1 | 50 ± 10.5 | 50.5 ± 12.1 |
| Min-Max | 18-71 | 21-71 | 18-70 |
| Source of infection (n(%)) | | | |
| Blood transfusion | 62 (25) | 41 (25) | 21 (26) |
| Toxicomania | 49 (20) | 34 (21) | 15 (18) |
| Unknown | 133 (55) | 87 (54) | 46 (56) |
| Alanine aminotransferase (ALT) IU/L: | | | |
| mean ± SD | 92 ± 78 | 87 ± 89 | 101 ± 55 |
| Min-Max | 22-647 | 22-510 | 32-647 |
| HCV genotypes, n (%) | | | |
| 1 | 135 (55.3) | 81 (50) | 54 (65.9) |
| 2 | 27 (11.1) | 23 (14.2) | 4 (4.9) |
| 3 | 26 (10.7) | 15 (9.3) | 11 (13.4) |
| 4 | 49 (20.1) | 38 (23.4) | 11 (13.4) |
| 5 | 4 (1.6) | 3 (1.9) | 1 (1.2) |
| 6 | 2 (0.8) | 1 (0.6) | 1 (1.2) |
| Unknown | 1 (0.4) | 1 (0.6) | 0 (0) |
| Number of viral copies per mL of serum: Mean (Min-Max) | $2.28.10^6$ $(3.2.10^3\text{-}1.9.10^8)$ | $1.83.10^6$ $(3.1.10^4\text{-}1.9.10^8)$ | $3.28.10^6$ $(3.2.10^3\text{-}5.9.10^7)$ |

IU = International Unit

The levels of expression of the genes was measured for each of the 244 biopsies (1 biopsy per patient).

Treatment of Samples

The hepatic biopsies were ground in nitrogen using a ceramic pestle and mortar (100% manual grinding).

The powder was recovered using a scalpel (Swann Morton 22, Reference 0208).

a) Extraction of RNAs

The powder obtained was dissolved in 1 mL of RNAble® Ref. GEXEXT00, Laboratoires Eurobio, France, to which 100 μL of chloroform had been added.

The mixture obtained was placed in ice or at 4° C. for 5 minutes, then was centrifuged at 13 000 g for 15 minutes.

The upper aqueous phase containing the RNAs was recovered into a fresh tube and 1 volume of isopropanol was added to it.

The tube was agitated by repeated inversion and was kept at 4° C. overnight, then was centrifuged at 13 000 g for 15 minutes. The supernatant was eliminated and the pellet containing the RNAs was taken up in a volume of 70% ethanol (extemporaneously prepared) and centrifuged again.

The pellet of RNA precipitate obtained was dried in the open air for approximately 1 hour then dissolved in 15 μL of water and stored at −80° C.

b) Measurement of RNAs

The evaluation of the concentration of extracted RNAs was carried out by measuring the optical density using a spectrometer (Nanodrop), and was verified after a freeze/thaw cycle.

The extracted RNAs were then diluted to obtain a 50 ng/μL solution.

Quality controls of the RNA were carried out by real time PCR (see below) by screening a ubiquitous expression control gene (known as endogenous), to verify that the RNA had not degraded (in fact, screening RPLP0).

Reverse Transcription or RT Step:

The reverse transcription was carried out on 200 ng of RNA in a reaction mixture produced in a volume of 20 μL, comprising the following reagents:

TABLE 16

| Reagent and reference product | Starting solution | Volume |
|---|---|---|
| SUPERSCRIPT II RNase H reverse transcriptase, Invitrogen, ref: 18064014 | 200 U/μL | 0.5 μL |
| SUPER SCRIPT 5× buffer Invitrogen, ref: 18064014 | — | 4.0 μL |
| RNAsin Promega, ref: N2111 | 40 U/μL | 0.5 μL |
| DTT | 100 mM | 2.0 μL |
| The 4 dNTPs GE Healthcare, ref: 28406552 | 10 mM | 1 μL |
| Pd(N) primers RANDOM HEXAMERS | 0.5 μg/μL | 6.0 μL |
| 50 (A260) units, 51 Perbio, ref: MB216601 | | |
| RNA | 50 ng/μL | 4.0 μL |
| H$_2$O | | qs 20 μL |

The reverse transcription reactions were carried out at the following temperatures:
at 20° C. for 10 minutes, then
at 42° C. for 30 minutes, and
at 99° C. for 5 minutes.

At this stage, the reaction mixtures were frozen or aliquoted or used directly for real time PCR amplification.

Quantitative Real Time PCR Step (qPCR):

The amplification was carried out using a Light Cycler® 480 (Roche Diagnostics, Mannheim, Germany). The results were generated using Light Cycler® Software 4.05/4.1.

Light Cycler® technology can be used to continuously monitor the appearance of the amplification products due to emission of a quantity of fluorescence which is proportional to the quantity of amplified product, which is itself dependent on the quantity of targets initially present in the sample to be analysed. Quantification (in relative values) of the gene expression was carried out using the method which is known by the name $2^{-\Delta Ct}$ ($2^{-\Delta Ct}=2^{-(Ct_{target}-Ct_{reference})}$; see Livak and Schmittgen 2001; Schmitten and Livak 2008), utilizing the values for "Cycle Threshold", or Ct, determined by the quantitative real time PCR apparatus. The smaller the value of Ct, the higher the initial quantity of transcribed RNA.

The reaction mixtures and the protocol used are described in the instruction leaflet in the LIGHT CYCLER® 480 SYBR GREEN I MASTER MIX kit (Roche Diagnostics, Mannheim, Germany; U.S. Pat. No. 4,683,202; U.S. Pat. No. 4,683,195; U.S. Pat. No. 4,965,188; U.S. Pat. No. 6,569,627).

After the reverse transcription step, the reaction mixtures (cDNAs) were diluted to ¼₀th (to verify the quality) or to ¹⁄₁₀₀th (for the target genes) before using them in qPCR. For each gene, the qPCRs were carried out in a reaction volume of 10 μL on a 384 well plate:
- 5 μL of reverse transcription reaction, diluted to ¼₀th (or ¹⁄₁₀₀th);
- 4.8 μL of reaction mixture from the Light Cycler® 480 SYBR Green I Master mix kit;
- 0.1 μL of a 50 μM solution for each of the two primers, i.e. a final volume of 0.5 μM for each primer.

The reaction mixtures were generally prepared for the 384 well plates.

The following primers were used:

The qPCRs were carried out using the following temperature conditions:
- a step for initiating denaturing at 95° C. for 10 minutes;
- 50 cycles of:
  - denaturing at 95° C. for 15 seconds;
  - hybridization/elongation at 65° C. for 30 seconds.

Each target sample was amplified in duplicate.

In order to overcome variations in the initial quantities of total RNA from one sample to another, at the same time a duplicate amplification was carried out of the RNAs of a gene used as an endogenous control, such as a gene involved in cellular metabolic cascades, for example RPLP0 (also known by the name 36B4; GENBANK accession number NM_001002) or TBP (GENBANK accession number NM_003194). In fact, the gene RPLP0 was used here as the endogenous control.

The quality of RNA extraction from the 244 biopsies was evaluated on the basis of the value of Ct of the reference gene, RPLP0. The classification was carried out as follows:
- RPLP0 Ct less than 22: very good RNA quality;
- RPLP0 Ct from 22 to 24: good RNA quality;

TABLE 17

| Symbol | Sense primer | SEQ ID NO: | Antisense primer | SEQ ID NO: |
|---|---|---|---|---|
| A2M | GCAAGTAAAAACCAAGGTCTTCCA | 1 | TCCAGTCAATTCCACCACTGTTC | 2 |
| SPP1 | TCGCAGACCTGACATCCAGTACC | 3 | CCATTCAACTCCTCGCTTTCCAT | 4 |
| VIM | CTCCCTCTGGTTGATACCCACTC | 5 | AGAAGTTTCGTTGATAACCTGTCCA | 6 |
| CXCL10 | CTGACTCTAAGTGGCATTCAAGGAG | 7 | GGTTGATTACTAATGCTGATGCAGG | 8 |
| IL8 | CACCGGAAGGAACCATCTCACTGT | 9 | TCCTTGGCAAAACTGCACCTTCA | 10 |
| ENG | CACAACATGCAGATCTGGACCACT | 11 | TGGGAGCTTGAAGCCACGAA | 12 |
| ANGPT2 | ACGTGAGGATGGCAGCGTT | 13 | GAAGGGTTACCAAATCCCACTTTAT | 14 |
| p14ARF | GGTTTTCGTGGTTCACATCCC | 15 | CCCATCATCATGACCTGGTCTT | 16 |
| CHI3L1 | GACCACAGGCCATCACAGTCC | 17 | TGTACCCCACAGCATAGTCAGTGTT | 18 |
| COL1A1 | CCTCCGGCTCCTGCTCCTCTT | 19 | GGCAGTTCTTGGTCTCGTCACA | 20 |
| CXCL1 | TCGAAAAGATGCTGAACAGTGACA | 21 | CTTCAGGAACAGCCACCAGTGA | 22 |
| CXCL6 | GTTTACGCGTTACGCTGAGAGTAAA | 23 | CGTTCTTCAGGGAGGCTACCA | 24 |
| CXCL11 | GTGTGCTACAGTTGTTCAAGGCTT | 25 | CTCAATATCTGCCACTTTCACTGCT | 26 |
| IHH | AGGCCGGCTTTGACTGGGTGTATT | 27 | GCGGCCGAGTGCTCGGACTT | 28 |
| IL6ST | CCTGCCTGTGACTTTCAAGCTACT | 29 | CATTCCACCCAAAGCATGTTATCT | 30 |
| IRF9 | GGCCGCATGGATGTTGCTGAG | 31 | TCTGAGTCCCTGGCTGGCCAGA | 32 |
| MMP1 | GGCTTGAAGCTGCTTACGAATTT | 33 | ACAGCCCAGTACTTATTCCCTTTGA | 34 |
| MMP2 | ACTGCGGTTTTCTCGAATCCA | 35 | GGTATCCATCGCCATGCTCC | 36 |
| MMP7 | AGTGGGAACAGGCTCAGGACTATC | 37 | GGTAGGCCAAAGAATTTTTGCATC | 38 |
| MMP9 | CGGCTTGCCCTGGTGCAGT | 39 | CGTCCCGGGTGTAGAGTCTCTCG | 40 |
| S100A4 | CTCGGGCAAAGAGGGTGACAA | 41 | GCTTCATCTGTCCTTTTCCCCAA | 42 |
| TIMP1 | GAGCCCCTGGCTTCTGGCA | 43 | GCCCTGATGACGAGGTCGGAA | 44 |
| RPLP0 | GGCGACCTGGAAGTCCAACT | 45 | CCATCAGCACCACAGCCTT | 46 |

RPLP0 Ct more than 24 and less than 26: average RNA quality;

RPLP0 Ct of 26 or more: poor RNA quality.

In order to increase the reliability of the bio-statistical analyses, only the data from RNA extraction of very good and good quality (RPLP0 Ct<22) were retained; there were 158 biopsies (64.8% of the 244 samples)

The quantity of transcripts of a target gene was deduced from the Ct ("Cycle threshold") which corresponded to the number of PCR cycles necessary in order to obtain a significant fluorescence signal. The target samples were normalized on the basis of their RPLP0 (or, if necessary, TBP) content, using the $2^{-\Delta Ct}$ method.

The measurement values for the biomarkers, or BMK (concentration of RNA, in fact value of Ct normalized using the $2^{-\Delta Ct}$ method) obtained for each of the 158 patients are presented in Tables 24 to 27 below.

TABLE 24

Clinical, biological and virological data

| Clinical, biological and virological data | Patients | F1 patients | F2 patients |
|---|---|---|---|
| n | 158 | 102 | 56 |
| Sex: male (%)/female (%) | 71 (45)/87 (55) | 41 (40)/61 (60) | 30 (54)/26 (46) |
| Age [mean ± standard deviation (Min-Max)] | 48.3 ± 11.0 (19-71) | 51.2 ± 11.2 (19-71) | 46.7 ± 11.0 (24-70) |
| Source of infection [n(%)] | | | |
| Blood transfusion | 37 (23) | 23 (23) | 14 (25) |
| toxicomania | 33 (21) | 23 (23) | 10 (18) |
| unknown | 88 (56) | 56 (55) | 32 (57) |
| Alanine amino-transferase (ALT) IU/L [mean ± standard deviation (Min-Max)] | 85 ± 60 (22-458) | 75 ± 48 (22-299) | 104 ± 73 (36-458) |
| HCV genotypes [n(%)] | | | |
| 1 | 86 (54) | 49 (48) | 37 (66) |
| 2 | 21 (13) | 18 (18) | 3 (5) |
| 3 | 15 (9) | 9 (9) | 6 (11) |
| 4 | 31 (20) | 23 (23) | 8 (14) |
| 5 | 2 (1) | 1 (1) | 1 (2) |
| 6 | 2 (1) | 1 (1) | 1 (2) |
| unknown | 1 (1) | 1 (1) | 0 (0) |
| Number of viral copies per mL of serum: | | | |
| mean | $6.2 \cdot 10^6$ | $6.5 \cdot 10^6$ | $5.8 \cdot 10^6$ |
| (Min-Max) | ($3.2 \cdot 10^3$-$1.9 \cdot 10^8$) | ($4.8 \cdot 10^4$-$1.9 \cdot 10^8$) | ($3.2 \cdot 10^3$-$5.9 \cdot 10^7$) |

TABLE 25

Patient's BMK values for the genes SPP1, A2M, VIM, IL8, CXCL10 and ENG (Ct normalised using the $2^{-\Delta Ct}$ method)

| Patient | Status (F1 or F2) | SPP1 | A2M | VIM | IL8 | CXCL10 | ENG |
|---|---|---|---|---|---|---|---|
| 1 | F1 | 0.228 | 3.387 | 0.346 | 4.332 | 0.574 | 1.141 |
| 8 | F1 | 0.050 | 4.141 | 0.170 | 0.000 | 1.297 | 1.371 |
| 9 | F1 | 0.071 | 1.495 | 0.117 | 0.625 | 2.078 | 0.997 |
| 11 | F1 | 0.242 | 4.014 | 0.360 | 2.971 | 1.860 | 1.454 |
| 16 | F1 | 0.105 | 1.352 | 0.120 | 1.237 | 0.000 | 0.388 |
| 22 | F1 | 0.133 | 1.676 | 0.176 | 6.791 | 0.346 | 0.674 |
| 25 | F1 | 0.054 | 6.543 | 0.167 | 1.546 | 0.357 | 1.597 |
| 26 | F1 | 0.755 | 8.754 | 0.380 | 0.923 | 2.370 | 1.899 |
| 32 | F1 | 0.167 | 3.399 | 0.125 | 4.515 | 0.549 | 1.157 |
| 33 | F1 | 0.551 | 3.643 | 0.256 | 69.878 | 17.692 | 0.946 |
| 38 | F1 | 0.143 | 1.347 | 0.177 | 0.967 | 2.780 | 1.000 |
| 40 | F1 | 0.117 | 2.151 | 0.142 | 0.423 | 4.857 | 1.014 |
| 41 | F1 | 0.277 | 1.653 | 0.129 | 1.264 | 0.333 | 0.163 |
| 46 | F1 | 0.200 | 5.081 | 0.221 | 3.362 | 4.141 | 1.094 |
| 48 | F1 | 0.100 | 0.509 | 0.119 | 1.805 | 2.567 | 0.880 |
| 56 | F1 | 0.129 | 4.790 | 0.232 | 4.088 | 3.193 | 0.901 |
| 65 | F1 | 0.196 | 5.205 | 0.124 | 2.218 | 1.003 | 1.010 |
| 66 | F1 | 0.779 | 2.289 | 0.161 | 1.847 | 0.700 | 1.177 |
| 69 | F1 | 0.223 | 1.664 | 0.068 | 2.936 | 0.509 | 0.901 |
| 74 | F1 | 0.067 | 2.063 | 0.119 | 5.772 | 1.765 | 0.674 |
| 83 | F1 | 0.156 | 2.959 | 0.166 | 4.918 | 6.255 | 1.400 |
| 86 | F1 | 0.124 | 3.446 | 0.179 | 3.789 | 2.858 | 1.266 |
| 88 | F1 | 0.157 | 1.597 | 0.087 | 0.766 | 0.735 | 0.667 |
| 91 | F1 | 0.224 | 3.543 | 0.171 | 0.595 | 1.641 | 1.079 |
| 95 | F1 | 0.069 | 3.931 | 0.116 | 3.118 | 0.264 | 0.727 |
| 98 | F1 | 0.163 | 1.173 | 0.089 | 3.717 | 0.292 | 0.847 |
| 105 | F1 | 0.176 | 0.383 | 0.079 | 2.017 | 0.149 | 0.782 |
| 107 | F1 | 0.324 | 1.414 | 0.173 | 0.443 | 0.727 | 1.613 |
| 109 | F1 | 0.092 | 0.644 | 0.082 | 1.610 | 1.275 | 0.722 |
| 113 | F1 | 0.144 | 2.558 | 0.133 | 1.725 | 0.434 | 0.798 |
| 116 | F1 | 0.094 | 1.537 | 0.228 | 0.792 | 18.316 | 1.343 |
| 125 | F1 | 0.010 | 0.382 | 0.063 | 1.421 | 0.234 | 0.241 |
| 126 | F1 | 0.158 | 2.204 | 0.074 | 0.450 | 0.460 | 1.039 |
| 134 | F1 | 0.390 | 1.270 | 0.108 | 3.028 | 0.345 | 0.633 |
| 135 | F1 | 0.048 | 0.690 | 0.115 | 8.625 | 1.032 | 0.425 |
| 139 | F1 | 0.067 | 1.079 | 0.087 | 0.410 | 1.197 | 0.664 |
| 141 | F1 | 0.066 | 1.664 | 0.059 | 2.615 | 1.352 | 0.362 |
| 143 | F1 | 0.089 | 1.873 | 0.343 | 1.184 | 0.301 | 0.732 |
| 144 | F1 | 0.269 | 1.899 | 0.113 | 1.206 | 1.676 | 0.655 |
| 145 | F1 | 0.438 | 5.315 | 0.235 | 5.681 | 0.626 | 1.347 |
| 146 | F1 | 0.029 | 0.153 | 0.331 | 0.509 | 0.027 | 0.465 |
| 151 | F1 | 0.034 | 1.597 | 0.075 | 0.297 | 1.288 | 0.406 |
| 152 | F1 | 0.074 | 1.892 | 0.074 | 0.887 | 1.068 | 0.818 |
| 153 | F1 | 0.128 | 2.297 | 0.064 | 1.004 | 0.200 | 0.509 |
| 154 | F1 | 0.168 | 3.204 | 0.089 | 2.011 | 0.639 | 0.616 |
| 155 | F1 | 0.199 | 2.918 | 0.072 | 0.694 | 1.324 | 1.007 |
| 157 | F1 | 0.044 | 1.939 | 0.076 | 1.257 | 3.182 | 0.465 |
| 159 | F1 | 0.449 | 5.897 | 0.117 | 4.345 | 1.853 | 0.599 |
| 161 | F1 | 0.187 | 2.949 | 0.082 | 0.707 | 0.256 | 0.622 |
| 163 | F1 | 0.700 | 5.959 | 0.076 | 3.998 | 2.258 | 0.570 |
| 164 | F1 | 0.378 | 1.395 | 0.084 | 2.616 | 0.745 | 0.766 |
| 165 | F1 | 0.176 | 0.901 | 0.043 | 0.757 | 0.033 | 0.593 |
| 167 | F1 | 0.147 | 5.483 | 0.111 | 4.209 | 2.354 | 1.474 |
| 169 | F1 | 0.009 | 0.914 | 0.042 | 0.415 | 0.574 | 0.637 |
| 170 | F1 | 0.066 | 2.639 | 0.060 | 1.308 | 0.083 | 0.509 |
| 171 | F1 | 0.530 | 4.213 | 0.089 | 6.820 | 0.664 | 0.505 |
| 172 | F1 | 0.066 | 1.873 | 0.086 | 0.000 | 0.774 | 0.838 |
| 175 | F1 | 0.231 | 1.966 | 0.134 | 10.676 | 0.257 | 0.697 |
| 178 | F1 | 0.211 | 3.824 | 0.089 | 0.671 | 1.057 | 0.886 |
| 182 | F1 | 0.055 | 1.821 | 0.059 | 0.544 | 0.236 | 0.793 |
| 189 | F1 | 0.182 | 3.031 | 0.073 | 0.828 | 3.771 | 0.963 |
| 210 | F1 | 0.043 | 2.338 | 0.073 | 0.325 | 0.355 | 0.448 |
| 214 | F1 | 0.031 | 3.694 | 0.071 | 1.456 | 5.637 | 0.766 |
| 216 | F1 | 0.030 | 1.404 | 0.042 | 0.844 | 0.333 | 0.349 |
| 217 | F1 | 0.026 | 1.815 | 0.085 | 1.033 | 1.068 | 0.674 |
| 219 | F1 | 0.101 | 2.990 | 0.088 | 0.577 | 1.688 | 0.707 |
| 223 | F1 | 0.052 | 2.042 | 0.043 | 2.416 | 1.429 | 0.437 |
| 224 | F1 | 0.241 | 2.250 | 0.090 | 2.211 | 1.025 | 1.007 |
| 226 | F1 | 0.060 | 1.017 | 0.095 | 0.000 | 0.735 | 0.737 |
| 227 | F1 | 0.079 | 2.181 | 0.052 | 1.629 | 0.336 | 0.695 |
| 229 | F1 | 0.136 | 6.521 | 0.093 | 2.709 | 14.074 | 0.835 |
| 235 | F1 | 0.078 | 3.294 | 0.047 | 0.787 | 0.597 | 0.603 |
| 240 | F1 | 0.150 | 5.011 | 0.110 | 2.478 | 7.336 | 0.865 |
| 241 | F1 | 0.052 | 0.624 | 0.036 | 0.865 | 0.750 | 0.457 |

TABLE 25-continued

Patient's BMK values for the genes SPP1, A2M, VIM, IL8, CXCL10 and ENG (Ct normalised using the $2^{-\Delta Ct}$ method)

| Patient | Status (F1 or F2) | SPP1 | A2M | VIM | IL8 | CXCL10 | ENG |
|---|---|---|---|---|---|---|---|
| 243 | F1 | 0.105 | 4.199 | 0.120 | 4.407 | 1.449 | 1.028 |
| 244 | F1 | 0.299 | 9.318 | 0.093 | 1.121 | 2.828 | 0.956 |
| 245 | F1 | 0.049 | 0.388 | 0.336 | 0.517 | 0.211 | 0.586 |
| 246 | F1 | 0.125 | 4.708 | 0.069 | 1.103 | 5.598 | 1.007 |
| 247 | F1 | 0.174 | 2.000 | 0.076 | 1.916 | 1.682 | 0.603 |
| 248 | F1 | 0.080 | 4.127 | 0.056 | 1.969 | 1.185 | 0.337 |
| 249 | F1 | 0.106 | 0.669 | 0.026 | 0.402 | 0.105 | 0.236 |
| 250 | F1 | 0.068 | 2.858 | 0.038 | 0.848 | 0.367 | 0.434 |
| 257 | F1 | 0.065 | 3.160 | 0.094 | 0.000 | 0.476 | 0.853 |
| 263 | F1 | 0.068 | 3.375 | 0.262 | 1.506 | 0.607 | 0.868 |
| 264 | F1 | 0.066 | 2.437 | 0.133 | 1.856 | 3.106 | 0.678 |
| 265 | F1 | 0.012 | 0.771 | 0.037 | 0.000 | 0.454 | 0.722 |
| 269 | F1 | 0.041 | 1.469 | 0.098 | 1.135 | 1.602 | 0.671 |
| 273 | F1 | 0.014 | 1.169 | 0.061 | 0.973 | 0.519 | 0.732 |
| 275 | F1 | 0.075 | 2.129 | 0.069 | 3.144 | 0.416 | 0.674 |
| 276 | F1 | 0.116 | 0.395 | 0.087 | 5.860 | 0.284 | 0.633 |
| 277 | F1 | 0.033 | 1.072 | 0.060 | 4.183 | 0.195 | 0.413 |
| 285 | F1 | 0.158 | 2.107 | 0.132 | 3.584 | 0.611 | 0.993 |
| 286 | F1 | 0.179 | 1.297 | 0.209 | 7.950 | 1.275 | 0.892 |
| 297 | F1 | 0.016 | 2.313 | 0.110 | 7.908 | 3.422 | 0.983 |
| 305 | F1 | 0.026 | 0.850 | 0.072 | 6.873 | 0.241 | 0.519 |
| 337 | F1 | 0.074 | 0.801 | 0.039 | 4.015 | 0.174 | 0.395 |
| 338 | F1 | 0.036 | 3.352 | 0.153 | 2.986 | 0.441 | 1.218 |
| 339 | F1 | 0.074 | 4.056 | 0.094 | 3.178 | 0.722 | 1.449 |
| 340 | F1 | 0.043 | 6.431 | 0.246 | 5.234 | 4.547 | 2.648 |
| 351 | F1 | 0.029 | 1.181 | 0.081 | 4.623 | 0.180 | 0.818 |
| 357 | F1 | 0.099 | 2.858 | 0.139 | 4.456 | 0.853 | 1.253 |
| 361 | F1 | 0.077 | 5.560 | 0.135 | 10.793 | 0.787 | 0.807 |
| 2 | F2 | 2.979 | 7.235 | 0.572 | 4.613 | 1.939 | 2.428 |
| 6 | F2 | 0.210 | 6.821 | 0.149 | 34.819 | 8.225 | 1.653 |
| 7 | F2 | 0.366 | 1.693 | 0.190 | 4.161 | 1.548 | 0.880 |
| 10 | F2 | 0.366 | 4.272 | 0.280 | 1.632 | 3.519 | 1.270 |
| 12 | F2 | 2.219 | 4.377 | 0.516 | 9.754 | 6.821 | 2.189 |
| 13 | F2 | 0.168 | 1.000 | 0.131 | 5.083 | 1.905 | 0.678 |
| 14 | F2 | 0.239 | 1.664 | 0.149 | 1.802 | 0.457 | 1.169 |
| 17 | F2 | 0.209 | 11.672 | 0.214 | 2.986 | 3.272 | 1.815 |
| 20 | F2 | 0.203 | 7.438 | 0.186 | 2.584 | 0.061 | 1.424 |
| 23 | F2 | 0.821 | 7.013 | 0.344 | 7.993 | 2.151 | 1.361 |
| 27 | F2 | 0.653 | 3.283 | 0.443 | 8.377 | 1.032 | 0.990 |
| 28 | F2 | 0.678 | 4.112 | 0.247 | 7.404 | 9.781 | 1.129 |
| 31 | F2 | 0.168 | 1.682 | 1.490 | 6.551 | 1.324 | 1.979 |
| 34 | F2 | 0.067 | 3.329 | 0.085 | 0.806 | 0.184 | 1.007 |
| 39 | F2 | 0.936 | 3.972 | 0.177 | 0.000 | 1.257 | 1.133 |
| 42 | F2 | 0.142 | 3.294 | 0.075 | 2.525 | 1.361 | 0.815 |
| 43 | F2 | 0.235 | 1.840 | 0.195 | 4.416 | 1.424 | 0.930 |
| 44 | F2 | 0.202 | 4.547 | 0.242 | 0.000 | 2.878 | 1.218 |
| 45 | F2 | 0.599 | 3.931 | 0.470 | 3.963 | 2.219 | 3.042 |
| 50 | F2 | 0.081 | 5.408 | 0.250 | 2.339 | 0.451 | 1.526 |
| 55 | F2 | 0.747 | 3.193 | 0.109 | 8.586 | 0.809 | 0.553 |
| 58 | F2 | 0.275 | 2.676 | 0.191 | 5.677 | 1.283 | 1.248 |
| 60 | F2 | 0.154 | 1.121 | 0.118 | 1.219 | 1.711 | 1.636 |
| 63 | F2 | 0.110 | 7.413 | 0.254 | 1.073 | 6.940 | 1.000 |
| 67 | F2 | 0.299 | 3.986 | 0.133 | 5.520 | 0.563 | 0.956 |
| 72 | F2 | 0.232 | 0.880 | 0.115 | 2.042 | 0.257 | 0.917 |
| 75 | F2 | 0.702 | 16.000 | 0.410 | 5.710 | 8.846 | 2.136 |
| 76 | F2 | 0.148 | 5.205 | 0.227 | 0.506 | 4.392 | 0.997 |
| 80 | F2 | 0.462 | 1.939 | 0.147 | 6.084 | 2.751 | 0.914 |
| 87 | F2 | 1.575 | 7.413 | 0.271 | 12.800 | 9.815 | 1.972 |
| 90 | F2 | 0.150 | 7.781 | 0.263 | 1.357 | 2.196 | 1.586 |
| 92 | F2 | 0.033 | 0.693 | 0.096 | 1.853 | 0.618 | 0.568 |
| 97 | F2 | 0.144 | 1.087 | 0.134 | 1.234 | 0.459 | 0.722 |
| 114 | F2 | 0.662 | 4.925 | 0.408 | 3.995 | 15.889 | 2.979 |
| 148 | F2 | 0.115 | 4.908 | 0.151 | 6.687 | 5.046 | 1.464 |
| 160 | F2 | 0.340 | 3.745 | 0.138 | 6.966 | 1.548 | 0.502 |
| 166 | F2 | 0.973 | 0.313 | 0.545 | 0.895 | 0.003 | 0.835 |
| 168 | F2 | 0.068 | 2.612 | 0.172 | 5.740 | 0.538 | 0.742 |
| 174 | F2 | 0.505 | 4.228 | 0.112 | 12.409 | 3.106 | 0.997 |
| 176 | F2 | 0.232 | 4.959 | 0.072 | 1.981 | 1.039 | 0.714 |
| 177 | F2 | 0.146 | 5.389 | 0.102 | 0.825 | 2.378 | 0.959 |
| 179 | F2 | 0.262 | 6.476 | 0.087 | 3.246 | 2.799 | 0.724 |
| 185 | F2 | 0.269 | 1.409 | 0.052 | 0.963 | 0.388 | 0.593 |
| 194 | F2 | 0.088 | 6.892 | 0.123 | 2.131 | 0.920 | 0.678 |
| 213 | F2 | 0.241 | 6.105 | 0.089 | 14.082 | 3.758 | 0.986 |
| 218 | F2 | 0.406 | 6.298 | 0.134 | 2.276 | 1.390 | 0.969 |
| 225 | F2 | 0.129 | 3.127 | 0.057 | 5.396 | 2.166 | 0.620 |
| 232 | F2 | 0.599 | 8.969 | 0.177 | 8.744 | 5.187 | 1.014 |
| 237 | F2 | 0.201 | 7.701 | 0.053 | 1.224 | 0.605 | 1.106 |
| 239 | F2 | 0.296 | 4.423 | 0.113 | 2.604 | 3.084 | 1.057 |
| 279 | F2 | 0.002 | 2.136 | 0.058 | 11.209 | 0.204 | 0.557 |
| 294 | F2 | 0.056 | 1.919 | 0.092 | 7.272 | 0.753 | 0.700 |
| 298 | F2 | 0.063 | 2.395 | 0.076 | 10.422 | 0.369 | 0.530 |
| 325 | F2 | 0.056 | 3.668 | 0.108 | 4.756 | 1.306 | 1.113 |
| 333 | F2 | 0.014 | 8.282 | 0.168 | 7.291 | 6.589 | 1.102 |
| 343 | F2 | 0.238 | 4.213 | 0.189 | 7.357 | 1.873 | 1.157 |

TABLE 26

Patient's BMK values for the genes IL6ST, p14ARF, MMP9, ANGPT2, CXCL11 and MMP2 (Ct normalised using the $2^{-\Delta Ct}$ method)

| Patient | Status (F1 or F2) | IL6ST | p14ARF | MMP9 | ANGPT2 | CXCL11 | MMP2 |
|---|---|---|---|---|---|---|---|
| 1 | F1 | 0.101 | 0.000 | 7.336 | 1.772 | 0.168 | 0.204 |
| 8 | F1 | 0.488 | 0.000 | 0.568 | 2.107 | 1.079 | 0.109 |
| 9 | F1 | 0.213 | 0.026 | 0.853 | 4.228 | 0.082 | 0.077 |
| 11 | F1 | 0.190 | 0.036 | 3.138 | 2.078 | 0.892 | 0.159 |
| 16 | F1 | 0.049 | 0.003 | 1.091 | 1.061 | 0.420 | 0.064 |
| 22 | F1 | 0.069 | 0.344 | 5.897 | 2.021 | 0.149 | 0.111 |
| 25 | F1 | 0.155 | 0.009 | 0.244 | 1.952 | 0.031 | 0.095 |
| 26 | F1 | 0.175 | 0.031 | 1.288 | 4.807 | 0.307 | 0.332 |
| 32 | F1 | 0.143 | 0.027 | 3.053 | 5.081 | 0.175 | 0.180 |
| 33 | F1 | 0.376 | 0.000 | 1.218 | 1.853 | 2.648 | 0.267 |
| 38 | F1 | 0.236 | 0.013 | 0.595 | 4.611 | 0.441 | 0.083 |
| 40 | F1 | 0.316 | 0.029 | 0.611 | 3.643 | 0.850 | 0.069 |
| 41 | F1 | 0.060 | 0.024 | 1.834 | 0.997 | 0.094 | 0.141 |
| 46 | F1 | 0.174 | 0.032 | 10.411 | 1.469 | 0.202 | 0.210 |
| 48 | F1 | 0.115 | 0.034 | 1.197 | 3.681 | 0.572 | 0.085 |
| 56 | F1 | 0.167 | 0.000 | 0.236 | 1.860 | 0.396 | 0.085 |
| 65 | F1 | 0.093 | 0.038 | 2.612 | 3.531 | 0.345 | 0.096 |
| 66 | F1 | 0.085 | 0.041 | 1.419 | 1.149 | 0.153 | 0.229 |
| 69 | F1 | 0.124 | 0.000 | 0.933 | 1.828 | 0.183 | 0.109 |
| 74 | F1 | 0.203 | 0.037 | 3.021 | 1.759 | 0.419 | 0.197 |

TABLE 26-continued

Patient's BMK values for the genes IL6ST, p14ARF, MMP9, ANGPT2, CXCL11 and MMP2 (Ct normalised using the $2^{-\Delta Ct}$ method)

| Patient | Status (F1 or F2) | IL6ST | p14ARF | MMP9 | ANGPT2 | CXCL11 | MMP2 |
|---|---|---|---|---|---|---|---|
| 83 | F1 | 0.307 | 0.020 | 2.888 | 2.685 | 0.662 | 0.111 |
| 86 | F1 | 0.127 | 0.034 | 4.469 | 3.824 | 0.405 | 0.226 |
| 88 | F1 | 0.144 | 0.000 | 2.158 | 2.454 | 0.144 | 0.040 |
| 91 | F1 | 0.068 | 0.019 | 2.908 | 0.540 | 0.261 | 0.058 |
| 95 | F1 | 0.129 | 0.037 | 2.594 | 2.378 | 0.066 | 0.104 |
| 98 | F1 | 0.102 | 0.020 | 0.222 | 1.625 | 0.099 | 0.093 |
| 105 | F1 | 0.042 | 0.023 | 0.717 | 1.613 | 0.023 | 0.005 |
| 107 | F1 | 0.154 | 0.005 | 1.283 | 2.751 | 0.060 | 0.247 |
| 109 | F1 | 0.070 | 0.011 | 1.235 | 1.602 | 0.126 | 0.100 |
| 113 | F1 | 0.146 | 0.047 | 0.344 | 2.129 | 0.100 | 0.156 |
| 116 | F1 | 0.177 | 0.132 | 0.000 | 8.056 | 1.735 | 0.128 |
| 125 | F1 | 0.074 | 0.010 | 0.161 | 0.826 | 0.042 | 0.013 |
| 126 | F1 | 0.076 | 0.025 | 0.798 | 1.464 | 0.074 | 0.061 |
| 134 | F1 | 0.015 | 0.007 | 1.091 | 0.276 | 0.036 | 0.030 |
| 135 | F1 | 0.067 | 0.011 | 1.121 | 1.809 | 0.195 | 0.027 |
| 139 | F1 | 0.074 | 0.018 | 0.143 | 0.103 | 0.116 | 0.099 |
| 141 | F1 | 0.067 | 0.025 | 3.238 | 0.180 | 0.766 | 0.024 |
| 143 | F1 | 0.117 | 0.009 | 1.297 | 0.176 | 0.444 | 0.078 |
| 144 | F1 | 0.128 | 0.012 | 0.653 | 0.366 | 0.597 | 0.142 |
| 145 | F1 | 0.253 | 0.038 | 3.317 | 0.498 | 0.131 | 0.245 |
| 146 | F1 | 0.032 | 0.028 | 0.534 | 0.143 | 0.007 | 1.352 |
| 151 | F1 | 0.120 | 0.008 | 0.292 | 0.181 | 0.123 | 0.043 |
| 152 | F1 | 0.188 | 0.012 | 0.444 | 0.403 | 0.165 | 0.029 |
| 153 | F1 | 0.076 | 0.006 | 1.361 | 0.124 | 0.065 | 0.014 |
| 154 | F1 | 0.263 | 0.017 | 0.093 | 0.312 | 0.182 | 0.018 |
| 155 | F1 | 0.106 | 0.023 | 1.094 | 0.104 | 0.235 | 0.025 |
| 157 | F1 | 0.156 | 0.019 | 0.473 | 0.534 | 0.898 | 0.029 |
| 159 | F1 | 0.253 | 0.026 | 4.469 | 0.073 | 0.186 | 0.049 |
| 161 | F1 | 0.171 | 0.013 | 0.853 | 0.097 | 0.061 | 0.038 |
| 163 | F1 | 0.282 | 0.022 | 0.841 | 0.033 | 0.188 | 0.012 |
| 164 | F1 | 0.188 | 0.007 | 0.758 | 0.097 | 0.166 | 0.041 |
| 165 | F1 | 0.107 | 0.013 | 0.249 | 0.044 | 0.045 | 0.007 |
| 167 | F1 | 0.160 | 0.035 | 3.618 | 0.041 | 0.390 | 0.057 |
| 169 | F1 | 0.200 | 0.015 | 0.529 | 0.029 | 0.033 | 0.029 |
| 170 | F1 | 0.162 | 0.010 | 0.507 | 0.042 | 0.007 | 0.046 |
| 171 | F1 | 0.098 | 0.016 | 1.197 | 0.047 | 0.246 | 0.051 |
| 172 | F1 | 1.741 | 0.000 | 8.664 | 0.000 | 0.147 | 0.030 |
| 175 | F1 | 0.116 | 0.013 | 0.821 | 0.120 | 0.124 | 0.022 |
| 178 | F1 | 0.202 | 0.016 | 0.345 | 0.088 | 0.087 | 0.024 |
| 182 | F1 | 0.063 | 0.005 | 1.046 | 0.054 | 0.080 | 0.049 |
| 189 | F1 | 0.202 | 0.015 | 0.127 | 0.076 | 0.300 | 0.052 |
| 210 | F1 | 0.134 | 0.010 | 0.361 | 0.031 | 0.124 | 0.009 |
| 214 | F1 | 0.157 | 0.005 | 0.247 | 0.132 | 0.379 | 0.039 |
| 216 | F1 | 0.039 | 0.014 | 0.324 | 0.173 | 0.069 | 0.006 |
| 217 | F1 | 0.454 | 0.006 | 0.053 | 1.521 | 0.092 | 0.053 |
| 219 | F1 | 0.114 | 0.010 | 0.155 | 0.676 | 0.231 | 0.023 |
| 223 | F1 | 0.112 | 0.009 | 0.053 | 0.702 | 0.277 | 0.031 |
| 224 | F1 | 0.207 | 0.015 | 1.137 | 1.558 | 0.256 | 0.053 |
| 226 | F1 | 0.314 | 0.013 | 1.711 | 1.315 | 0.208 | 0.036 |
| 227 | F1 | 0.134 | 0.012 | 0.438 | 2.676 | 0.059 | 0.052 |
| 229 | F1 | 0.257 | 0.022 | 1.061 | 1.490 | 2.454 | 0.027 |
| 235 | F1 | 0.151 | 0.012 | 0.183 | 4.155 | 0.324 | 0.040 |
| 240 | F1 | 0.355 | 0.023 | 0.940 | 0.862 | 1.608 | 0.051 |
| 241 | F1 | 0.169 | 0.009 | 0.582 | 0.940 | 0.115 | 0.018 |
| 243 | F1 | 0.240 | 0.039 | 0.766 | 1.580 | 0.338 | 0.075 |
| 244 | F1 | 0.631 | 0.037 | 0.722 | 2.549 | 0.574 | 0.064 |
| 245 | F1 | 0.219 | 0.005 | 0.212 | 1.670 | 0.050 | 0.637 |
| 246 | F1 | 0.215 | 0.012 | 0.182 | 0.593 | 0.315 | 0.053 |
| 247 | F1 | 0.202 | 0.005 | 1.064 | 0.717 | 0.626 | 0.028 |
| 248 | F1 | 0.151 | 0.007 | 3.605 | 0.247 | 0.184 | 0.033 |
| 249 | F1 | 0.177 | 0.009 | 0.135 | 0.547 | 0.061 | 0.021 |
| 250 | F1 | 0.041 | 0.000 | 0.350 | 1.209 | 0.079 | 0.022 |
| 257 | F1 | 0.194 | 0.009 | 0.177 | 1.145 | 0.275 | 0.021 |
| 263 | F1 | 0.354 | 0.003 | 0.351 | 2.395 | 0.277 | 0.030 |
| 264 | F1 | 0.133 | 0.017 | 0.509 | 0.712 | 0.380 | 0.053 |
| 265 | F1 | 0.047 | 0.009 | 0.291 | 0.923 | 0.024 | 0.008 |
| 269 | F1 | 0.240 | 0.014 | 0.207 | 0.555 | 0.280 | 0.019 |
| 273 | F1 | 0.238 | 0.004 | 0.091 | 0.584 | 0.135 | 0.015 |
| 275 | F1 | 0.122 | 0.006 | 0.371 | 0.790 | 0.053 | 0.022 |
| 276 | F1 | 0.115 | 0.007 | 1.165 | 0.267 | 0.084 | 0.054 |
| 277 | F1 | 0.277 | 0.011 | 0.076 | 0.576 | 0.062 | 0.008 |
| 285 | F1 | 0.122 | 0.011 | 0.774 | 0.859 | 0.101 | 0.053 |
| 286 | F1 | 0.138 | 0.008 | 0.480 | 2.858 | 0.354 | 0.071 |
| 297 | F1 | 0.205 | 0.012 | 0.590 | 1.202 | 0.521 | 0.035 |

TABLE 26-continued

Patient's BMK values for the genes IL6ST, p14ARF, MMP9, ANGPT2, CXCL11 and MMP2 (Ct normalised using the $2^{-\Delta Ct}$ method)

| Patient | Status (F1 or F2) | IL6ST | p14ARF | MMP9 | ANGPT2 | CXCL11 | MMP2 |
|---|---|---|---|---|---|---|---|
| 305 | F1 | 0.092 | 0.008 | 0.337 | 0.712 | 0.149 | 0.024 |
| 337 | F1 | 0.116 | 0.000 | 0.163 | 0.463 | 0.059 | 0.013 |
| 338 | F1 | 0.151 | 0.005 | 2.346 | 0.904 | 0.076 | 0.067 |
| 339 | F1 | 0.313 | 0.006 | 0.804 | 1.952 | 0.182 | 0.093 |
| 340 | F1 | 0.342 | 0.008 | 0.396 | 2.462 | 0.357 | 0.272 |
| 351 | F1 | 0.206 | 0.000 | 0.332 | 2.204 | 0.111 | 0.014 |
| 357 | F1 | 0.241 | 0.004 | 0.113 | 1.735 | 0.203 | 0.058 |
| 361 | F1 | 0.144 | 0.004 | 1.014 | 0.653 | 0.148 | 0.094 |
| 2 | F2 | 0.214 | 0.000 | 2.908 | 3.494 | 0.620 | 0.584 |
| 6 | F2 | 0.601 | 0.000 | 36.002 | 20.749 | 0.490 | 0.152 |
| 7 | F2 | 0.087 | 0.000 | 2.266 | 2.007 | 0.360 | 0.059 |
| 10 | F2 | 0.049 | 0.012 | 1.772 | 12.553 | 0.712 | 0.136 |
| 12 | F2 | 0.148 | 0.034 | 1.873 | 1.670 | 0.695 | 0.495 |
| 13 | F2 | 0.050 | 0.037 | 0.460 | 2.049 | 0.225 | 0.014 |
| 14 | F2 | 0.048 | 0.029 | 6.364 | 1.602 | 0.075 | 0.169 |
| 17 | F2 | 0.261 | 0.039 | 4.332 | 2.000 | 0.349 | 0.171 |
| 20 | F2 | 0.142 | 0.028 | 3.127 | 2.959 | 0.184 | 0.052 |
| 23 | F2 | 0.207 | 0.148 | 1.320 | 2.144 | 0.440 | 0.296 |
| 27 | F2 | 0.090 | 0.077 | 1.439 | 1.035 | 0.198 | 0.246 |
| 28 | F2 | 0.080 | 0.137 | 12.168 | 1.053 | 1.106 | 0.166 |
| 31 | F2 | 0.131 | 0.044 | 1.279 | 2.732 | 0.644 | 0.124 |
| 34 | F2 | 0.067 | 0.016 | 0.826 | 2.266 | 0.025 | 0.125 |
| 39 | F2 | 0.159 | 0.000 | 1.784 | 3.329 | 0.144 | 0.290 |
| 42 | F2 | 0.075 | 0.000 | 0.563 | 0.644 | 0.174 | 0.045 |
| 43 | F2 | 0.108 | 0.038 | 2.676 | 2.049 | 0.378 | 0.264 |
| 44 | F2 | 0.282 | 0.020 | 1.464 | 3.375 | 1.361 | 0.137 |
| 45 | F2 | 0.286 | 0.068 | 8.515 | 5.081 | 0.927 | 0.326 |
| 50 | F2 | 0.044 | 0.039 | 8.369 | 0.662 | 0.050 | 0.232 |
| 55 | F2 | 0.086 | 0.065 | 0.986 | 1.647 | 0.164 | 0.132 |
| 58 | F2 | 0.120 | 0.062 | 3.630 | 1.602 | 0.234 | 0.200 |
| 60 | F2 | 0.191 | 0.000 | 2.594 | 10.339 | 0.222 | 0.076 |
| 63 | F2 | 0.200 | 0.015 | 0.177 | 1.439 | 0.486 | 0.068 |
| 67 | F2 | 0.098 | 0.068 | 1.682 | 3.010 | 0.146 | 0.129 |
| 72 | F2 | 0.073 | 0.012 | 1.079 | 3.329 | 0.047 | 0.064 |
| 75 | F2 | 0.175 | 0.121 | 1.091 | 3.732 | 1.790 | 0.491 |
| 76 | F2 | 0.360 | 0.004 | 0.829 | 2.078 | 0.476 | 0.273 |
| 80 | F2 | 0.116 | 0.041 | 0.969 | 0.648 | 0.425 | 0.046 |
| 87 | F2 | 0.184 | 0.035 | 3.972 | 1.986 | 0.611 | 0.202 |
| 90 | F2 | 0.176 | 0.017 | 4.611 | 3.918 | 0.301 | 0.198 |
| 92 | F2 | 0.063 | 0.014 | 0.616 | 0.543 | 0.146 | 0.036 |
| 97 | F2 | 0.077 | 0.017 | 1.227 | 4.000 | 0.089 | 0.064 |
| 114 | F2 | 0.253 | 0.070 | 12.817 | 4.773 | 5.205 | 0.642 |
| 148 | F2 | 0.363 | 0.072 | 0.551 | 0.525 | 0.351 | 0.125 |
| 160 | F2 | 0.189 | 0.040 | 7.490 | 0.021 | 0.543 | 0.045 |
| 166 | F2 | 0.054 | 0.000 | 8.515 | 0.000 | 0.007 | 0.278 |
| 168 | F2 | 0.136 | 0.053 | 4.807 | 0.146 | 0.103 | 0.094 |
| 174 | F2 | 0.100 | 0.047 | 1.137 | 0.000 | 0.688 | 0.034 |
| 176 | F2 | 0.137 | 0.013 | 0.532 | 0.040 | 0.182 | 0.049 |
| 177 | F2 | 0.158 | 0.032 | 0.502 | 0.064 | 0.387 | 0.033 |
| 179 | F2 | 0.268 | 0.023 | 0.428 | 0.054 | 0.685 | 0.026 |
| 185 | F2 | 0.132 | 0.005 | 0.432 | 0.023 | 0.100 | 0.036 |
| 194 | F2 | 0.138 | 0.023 | 1.257 | 0.061 | 0.191 | 0.050 |
| 213 | F2 | 0.254 | 0.030 | 0.304 | 0.043 | 0.432 | 0.018 |
| 218 | F2 | 0.108 | 0.017 | 0.057 | 4.405 | 0.257 | 0.113 |
| 225 | F2 | 0.059 | 0.025 | 0.568 | 0.409 | 0.361 | 0.011 |
| 232 | F2 | 0.419 | 0.036 | 1.809 | 1.699 | 0.886 | 0.138 |
| 237 | F2 | 0.140 | 0.000 | 0.378 | 6.080 | 0.236 | 0.084 |
| 239 | F2 | 0.290 | 0.034 | 0.620 | 1.094 | 0.502 | 0.057 |
| 279 | F2 | 0.132 | 0.007 | 0.273 | 1.206 | 0.071 | 0.014 |
| 294 | F2 | 0.211 | 0.010 | 0.260 | 1.404 | 0.087 | 0.020 |
| 298 | F2 | 0.182 | 0.007 | 0.218 | 0.590 | 0.093 | 0.020 |
| 325 | F2 | 0.162 | 0.011 | 1.449 | 1.039 | 0.228 | 0.090 |
| 333 | F2 | 0.662 | 0.050 | 1.329 | 0.911 | 1.257 | 0.075 |
| 343 | F2 | 0.173 | 0.006 | 2.445 | 1.490 | 0.186 | 0.126 |

TABLE 27

Patient's BMK values for the genes MMP7, S100A41, TIMP1, CHI3L1, COL1A1 and CXCL1 (Ct normalised using the $2^{-\Delta Ct}$ method)

| Patient | Status (F1 or F2) | MMP7 | S100A41 | TIMP1 | CHI3L1 | COL1A1 | CXCL1 |
|---|---|---|---|---|---|---|---|
| 1 | F1 | 0.150 | 1.338 | 0.252 | 0.547 | 0.727 | 2.329 |
| 8 | F1 | 0.023 | 0.821 | 0.347 | 1.912 | 0.295 | 1.474 |
| 9 | F1 | 0.018 | 0.979 | 0.198 | 0.009 | 0.226 | 0.151 |
| 11 | F1 | 0.129 | 2.505 | 0.626 | 1.145 | 0.465 | 0.871 |
| 16 | F1 | 0.007 | 1.083 | 0.121 | 0.011 | 0.151 | 0.200 |
| 22 | F1 | 0.010 | 0.451 | 0.168 | 1.231 | 0.204 | 0.549 |
| 25 | F1 | 0.005 | 0.717 | 0.288 | 1.459 | 0.637 | 0.448 |
| 26 | F1 | 0.002 | 1.459 | 0.807 | 1.227 | 1.821 | 2.505 |
| 32 | F1 | 0.026 | 1.000 | 0.383 | 1.366 | 0.446 | 0.688 |
| 33 | F1 | 0.000 | 0.669 | 0.540 | 0.495 | 0.553 | 4.257 |
| 38 | F1 | 0.023 | 0.877 | 0.195 | 0.856 | 0.184 | 0.409 |
| 40 | F1 | 0.019 | 0.478 | 0.136 | 0.201 | 0.151 | 0.154 |
| 41 | F1 | 0.009 | 0.880 | 0.263 | 0.017 | 0.369 | 0.555 |
| 46 | F1 | 0.073 | 1.185 | 0.551 | 0.338 | 2.078 | 0.815 |
| 48 | F1 | 0.006 | 0.821 | 0.241 | 0.313 | 0.227 | 0.296 |
| 56 | F1 | 0.034 | 0.683 | 0.204 | 0.350 | 0.354 | 0.000 |
| 65 | F1 | 0.033 | 1.161 | 0.296 | 0.051 | 0.344 | 0.429 |
| 66 | F1 | 0.073 | 1.125 | 0.285 | 0.151 | 0.901 | 0.760 |
| 69 | F1 | 0.020 | 0.471 | 0.176 | 0.191 | 0.325 | 0.536 |
| 74 | F1 | 0.058 | 0.507 | 0.207 | 0.379 | 0.246 | 1.490 |
| 83 | F1 | 0.020 | 0.933 | 0.244 | 0.801 | 0.790 | 0.431 |
| 86 | F1 | 0.049 | 2.078 | 0.514 | 0.973 | 0.512 | 0.753 |
| 88 | F1 | 0.065 | 0.572 | 0.158 | 0.065 | 0.293 | 0.252 |
| 91 | F1 | 0.100 | 1.061 | 0.298 | 1.137 | 0.563 | 0.265 |
| 95 | F1 | 0.029 | 0.683 | 0.245 | 0.688 | 0.470 | 0.285 |
| 98 | F1 | 0.014 | 0.541 | 0.173 | 0.009 | 0.277 | 0.362 |
| 105 | F1 | 0.010 | 0.580 | 0.166 | 0.012 | 0.387 | 0.187 |
| 107 | F1 | 0.020 | 0.437 | 0.242 | 0.085 | 0.753 | 0.280 |
| 109 | F1 | 0.012 | 0.940 | 0.182 | 0.350 | 0.378 | 0.247 |
| 113 | F1 | 0.011 | 0.613 | 0.174 | 0.074 | 0.320 | 0.568 |
| 116 | F1 | 0.007 | 1.014 | 0.388 | 0.712 | 0.514 | 0.396 |
| 125 | F1 | 0.009 | 0.370 | 0.078 | 0.000 | 0.121 | 0.130 |
| 126 | F1 | 0.017 | 0.467 | 0.276 | 0.178 | 0.177 | 0.503 |
| 134 | F1 | 0.012 | 0.529 | 0.137 | 0.091 | 0.220 | 0.290 |
| 135 | F1 | 0.021 | 1.032 | 0.133 | 0.247 | 0.149 | 0.669 |
| 139 | F1 | 0.009 | 0.493 | 0.186 | 0.370 | 0.210 | 0.184 |
| 141 | F1 | 0.036 | 1.042 | 0.142 | 0.275 | 0.139 | 0.148 |
| 143 | F1 | 0.021 | 0.607 | 0.228 | 0.184 | 0.246 | 0.252 |
| 144 | F1 | 0.013 | 0.807 | 0.111 | 0.136 | 0.328 | 0.295 |
| 145 | F1 | 0.237 | 1.380 | 0.232 | 0.225 | 1.079 | 1.454 |
| 146 | F1 | 0.000 | 1.231 | 0.033 | 0.011 | 0.376 | 0.191 |
| 151 | F1 | 0.013 | 0.607 | 0.076 | 0.226 | 0.260 | 0.071 |
| 152 | F1 | 0.029 | 0.132 | 0.032 | 0.074 | 0.255 | 0.331 |
| 153 | F1 | 0.003 | 0.226 | 0.140 | 0.106 | 0.278 | 0.213 |
| 154 | F1 | 0.074 | 0.966 | 0.125 | 0.378 | 0.313 | 0.142 |
| 155 | F1 | 0.008 | 1.181 | 0.284 | 0.277 | 0.382 | 0.251 |
| 157 | F1 | 0.016 | 0.269 | 0.091 | 0.010 | 0.252 | 0.212 |
| 159 | F1 | 0.124 | 0.669 | 0.135 | 0.164 | 0.382 | 0.267 |
| 161 | F1 | 0.063 | 0.267 | 0.098 | 0.054 | 0.176 | 0.523 |
| 163 | F1 | 0.051 | 0.000 | 0.184 | 1.380 | 0.578 | 0.519 |
| 164 | F1 | 0.073 | 0.676 | 0.143 | 0.012 | 0.426 | 0.428 |
| 165 | F1 | 0.013 | 0.362 | 0.088 | 0.035 | 0.061 | 0.104 |
| 167 | F1 | 0.092 | 0.787 | 0.979 | 6.320 | 1.079 | 0.904 |
| 169 | F1 | 0.029 | 0.295 | 0.136 | 0.004 | 0.168 | 0.062 |
| 170 | F1 | 0.022 | 0.419 | 0.094 | 0.135 | 0.168 | 0.191 |
| 171 | F1 | 0.093 | 0.904 | 0.184 | 0.232 | 0.440 | 0.838 |
| 172 | F1 | 0.285 | 0.742 | 0.206 | 0.387 | 0.221 | 0.338 |
| 175 | F1 | 0.292 | 0.678 | 0.222 | 1.145 | 0.258 | 0.787 |
| 178 | F1 | 0.082 | 0.398 | 0.164 | 0.028 | 0.275 | 0.329 |
| 182 | F1 | 0.019 | 0.481 | 0.170 | 0.022 | 0.325 | 0.207 |
| 189 | F1 | 0.023 | 0.798 | 0.475 | 1.469 | 0.253 | 0.683 |
| 210 | F1 | 0.035 | 0.434 | 0.088 | 0.111 | 0.090 | 0.055 |
| 214 | F1 | 0.008 | 0.490 | 0.198 | 0.171 | 0.362 | 0.457 |
| 216 | F1 | 0.013 | 0.454 | 0.089 | 0.082 | 0.102 | 0.110 |
| 217 | F1 | 0.017 | 0.374 | 0.151 | 0.008 | 0.122 | 0.529 |
| 219 | F1 | 0.022 | 0.534 | 0.158 | 0.023 | 0.164 | 0.221 |
| 223 | F1 | 0.004 | 0.476 | 0.189 | 0.467 | 0.153 | 0.121 |
| 224 | F1 | 0.042 | 0.856 | 0.177 | 0.277 | 0.865 | 0.829 |
| 226 | F1 | 0.011 | 0.305 | 0.082 | 0.033 | 0.128 | 0.566 |
| 227 | F1 | 0.021 | 0.169 | 0.045 | 0.012 | 0.070 | 0.136 |
| 229 | F1 | 0.029 | 1.098 | 0.221 | 0.090 | 0.367 | 0.671 |
| 235 | F1 | 0.019 | 0.229 | 0.108 | 0.943 | 0.134 | 0.225 |
| 240 | F1 | 0.026 | 0.710 | 0.310 | 0.252 | 0.418 | 0.818 |
| 241 | F1 | 0.035 | 0.283 | 0.071 | 0.044 | 0.156 | 0.516 |

TABLE 27-continued

Patient's BMK values for the genes MMP7, S100A41, TIMP1, CHI3L1, COL1A1 and CXCL1 (Ct normalised using the $2^{-\Delta Ct}$ method)

| Patient | Status (F1 or F2) | MMP7 | S100A41 | TIMP1 | CHI3L1 | COL1A1 | CXCL1 |
|---|---|---|---|---|---|---|---|
| 243 | F1 | 0.076 | 0.599 | 0.306 | 1.986 | 0.618 | 1.320 |
| 244 | F1 | 0.167 | 0.378 | 0.350 | 0.315 | 0.616 | 0.543 |
| 245 | F1 | 0.002 | 5.152 | 0.785 | 0.030 | 4.014 | 0.719 |
| 246 | F1 | 0.046 | 0.578 | 0.380 | 2.732 | 0.662 | 0.714 |
| 247 | F1 | 0.067 | 0.434 | 0.188 | 0.033 | 0.340 | 0.337 |
| 248 | F1 | 0.055 | 0.369 | 0.101 | 0.055 | 0.242 | 0.541 |
| 249 | F1 | 0.006 | 0.135 | 0.268 | 1.699 | 0.121 | 0.072 |
| 250 | F1 | 0.219 | 0.234 | 0.095 | 0.559 | 0.176 | 1.371 |
| 257 | F1 | 0.015 | 0.237 | 0.167 | 0.275 | 0.195 | 0.444 |
| 263 | F1 | 0.046 | 0.344 | 0.131 | 0.001 | 0.062 | 0.398 |
| 264 | F1 | 0.023 | 0.518 | 0.250 | 0.146 | 0.473 | 0.099 |
| 265 | F1 | 0.000 | 0.130 | 0.060 | 0.004 | 0.004 | 0.000 |
| 269 | F1 | 0.013 | 0.559 | 0.116 | 4.925 | 0.150 | 0.176 |
| 273 | F1 | 0.008 | 0.339 | 0.140 | 0.020 | 0.180 | 0.146 |
| 275 | F1 | 0.022 | 0.366 | 0.159 | 0.576 | 0.092 | 0.117 |
| 276 | F1 | 0.011 | 0.470 | 0.112 | 0.745 | 0.139 | 0.275 |
| 277 | F1 | 0.014 | 0.418 | 0.055 | 0.102 | 0.087 | 0.077 |
| 285 | F1 | 0.029 | 0.478 | 0.249 | 0.049 | 0.145 | 0.557 |
| 286 | F1 | 0.037 | 0.572 | 0.228 | 0.639 | 0.252 | 0.127 |
| 297 | F1 | 0.005 | 0.002 | 0.140 | 0.162 | 0.115 | 0.651 |
| 305 | F1 | 0.037 | 0.241 | 0.121 | 0.245 | 0.107 | 0.286 |
| 337 | F1 | 0.009 | 0.135 | 0.090 | 0.129 | 0.035 | 0.076 |
| 338 | F1 | 0.026 | 0.370 | 0.277 | 0.116 | 0.483 | 0.338 |
| 339 | F1 | 0.031 | 0.457 | 0.215 | 0.013 | 0.419 | 0.193 |
| 340 | F1 | 0.099 | 0.812 | 0.465 | 0.239 | 0.847 | 0.336 |
| 351 | F1 | 0.063 | 0.419 | 0.176 | 0.024 | 0.142 | 0.272 |
| 357 | F1 | 0.017 | 0.478 | 0.255 | 0.057 | 0.669 | 0.204 |
| 361 | F1 | 0.052 | 0.549 | 0.233 | 0.144 | 0.976 | 0.874 |
| 2 | F2 | 0.151 | 1.664 | 0.631 | 0.460 | 1.828 | 4.891 |
| 6 | F2 | 1.197 | 0.532 | 0.415 | 0.798 | 0.521 | 0.346 |
| 7 | F2 | 0.072 | 1.189 | 0.245 | 0.082 | 0.408 | 1.181 |
| 10 | F2 | 0.000 | 1.248 | 0.333 | 0.208 | 0.553 | 1.521 |
| 12 | F2 | 0.119 | 2.868 | 0.787 | 0.914 | 2.412 | 1.429 |
| 13 | F2 | 0.000 | 1.177 | 0.118 | 0.402 | 0.075 | 1.490 |
| 14 | F2 | 0.015 | 1.253 | 0.293 | 0.000 | 0.000 | 0.416 |
| 17 | F2 | 0.006 | 0.883 | 0.616 | 0.401 | 0.288 | 0.467 |
| 20 | F2 | 0.047 | 0.664 | 0.418 | 0.058 | 0.012 | 0.319 |
| 23 | F2 | 0.020 | 0.862 | 0.856 | 0.092 | 0.657 | 1.500 |
| 27 | F2 | 0.017 | 1.886 | 0.305 | 1.210 | 0.908 | 1.210 |
| 28 | F2 | 0.042 | 1.753 | 0.710 | 3.719 | 0.188 | 0.375 |
| 31 | F2 | 0.016 | 1.240 | 0.402 | 0.106 | 0.193 | 1.007 |
| 34 | F2 | 0.003 | 0.398 | 0.197 | 0.124 | 0.334 | 0.094 |
| 39 | F2 | 0.024 | 0.923 | 0.275 | 0.350 | 0.693 | 0.676 |
| 42 | F2 | 0.012 | 0.416 | 0.199 | 0.429 | 0.174 | 0.226 |
| 43 | F2 | 0.032 | 1.521 | 0.361 | 0.246 | 0.491 | 0.956 |
| 44 | F2 | 0.035 | 1.400 | 0.305 | 0.235 | 0.258 | 0.540 |
| 45 | F2 | 0.027 | 2.395 | 0.758 | 0.125 | 0.793 | 2.289 |
| 50 | F2 | 0.009 | 1.210 | 0.396 | 0.166 | 1.892 | 0.747 |
| 55 | F2 | 0.024 | 0.576 | 0.232 | 2.558 | 0.432 | 0.953 |
| 58 | F2 | 0.024 | 0.664 | 0.211 | 0.386 | 0.807 | 0.413 |
| 60 | F2 | 0.036 | 0.719 | 0.171 | 0.086 | 0.543 | 0.651 |
| 63 | F2 | 0.023 | 0.880 | 0.310 | 3.084 | 0.175 | 0.420 |
| 67 | F2 | 0.065 | 0.983 | 0.228 | 0.188 | 0.529 | 0.601 |
| 72 | F2 | 0.025 | 0.620 | 0.207 | 0.244 | 0.374 | 0.067 |
| 75 | F2 | 0.094 | 1.729 | 1.682 | 2.990 | 2.732 | 1.257 |
| 76 | F2 | 0.050 | 0.859 | 0.415 | 5.579 | 0.671 | 0.844 |
| 80 | F2 | 0.044 | 0.824 | 0.192 | 0.369 | 0.646 | 0.678 |
| 87 | F2 | 0.093 | 1.575 | 0.639 | 1.564 | 1.288 | 1.735 |
| 90 | F2 | 0.104 | 1.113 | 0.449 | 0.570 | 0.868 | 0.776 |
| 92 | F2 | 0.017 | 0.874 | 0.185 | 0.025 | 0.113 | 0.157 |
| 97 | F2 | 0.053 | 0.648 | 0.081 | 0.249 | 0.378 | 0.388 |
| 114 | F2 | 0.165 | 2.211 | 0.609 | 0.807 | 1.439 | 3.494 |
| 148 | F2 | 0.069 | 0.410 | 0.333 | 0.405 | 1.028 | 1.459 |
| 160 | F2 | 0.110 | 1.083 | 0.228 | 0.370 | 0.536 | 1.165 |
| 166 | F2 | 0.021 | 3.797 | 0.041 | 0.237 | 1.257 | 0.175 |
| 168 | F2 | 0.102 | 1.253 | 0.212 | 0.432 | 0.883 | 1.366 |
| 174 | F2 | 0.074 | 1.400 | 0.372 | 4.332 | 0.976 | 1.729 |
| 176 | F2 | 0.051 | 0.467 | 0.173 | 0.437 | 0.454 | 0.732 |
| 177 | F2 | 0.039 | 0.877 | 0.164 | 0.026 | 0.296 | 0.263 |
| 179 | F2 | 0.036 | 0.563 | 0.255 | 0.114 | 0.523 | 0.366 |
| 185 | F2 | 0.059 | 0.357 | 0.097 | 0.032 | 0.270 | 0.514 |
| 194 | F2 | 0.030 | 0.422 | 0.209 | 0.346 | 0.309 | 1.072 |
| 213 | F2 | 0.105 | 0.660 | 0.475 | 5.028 | 0.444 | 0.886 |
| 218 | F2 | 0.144 | 0.719 | 0.326 | 0.431 | 0.859 | 0.853 |

TABLE 27-continued

Patient's BMK values for the genes MMP7, S100A41, TIMP1, CHI3L1, COL1A1 and CXCL1 (Ct normalised using the $2^{-\Delta Ct}$ method)

| Patient | Status (F1 or F2) | MMP7 | S100A41 | TIMP1 | CHI3L1 | COL1A1 | CXCL1 |
|---|---|---|---|---|---|---|---|
| 225 | F2 | 0.168 | 1.025 | 0.386 | 2.639 | 0.434 | 0.766 |
| 232 | F2 | 0.139 | 0.920 | 0.521 | 2.313 | 0.760 | 1.952 |
| 237 | F2 | 0.188 | 0.605 | 0.232 | 0.275 | 0.534 | 0.438 |
| 239 | F2 | 0.042 | 0.238 | 0.195 | 0.184 | 0.570 | 1.310 |
| 279 | F2 | 0.012 | 0.192 | 0.125 | 0.000 | 0.004 | 0.105 |
| 294 | F2 | 0.019 | 0.312 | 0.133 | 0.296 | 0.068 | 0.311 |
| 298 | F2 | 0.000 | 0.006 | 0.133 | 0.006 | 0.060 | 0.152 |
| 325 | F2 | 0.010 | 0.660 | 0.237 | 0.089 | 0.221 | 0.366 |
| 333 | F2 | 0.249 | 0.646 | 0.403 | 0.262 | 0.361 | 0.555 |
| 343 | F2 | 0.022 | 0.470 | 0.152 | 0.015 | 0.574 | 0.292 |

TABLE 28

Patient's BMK values for the genes CXCL6, IHH, IRF9 and MMP1 (Ct normalised using the $2^{-\Delta Ct}$ method)

| Patient | Status (F1 or F2) | CXCL6 | IHH | IRF9 | MMP1 |
|---|---|---|---|---|---|
| 1 | F1 | 7.863 | 0.259 | 0.120 | 0.000 |
| 8 | F1 | 0.760 | 0.727 | 0.227 | 0.243 |
| 9 | F1 | 3.084 | 0.212 | 0.176 | 0.044 |
| 11 | F1 | 3.986 | 0.339 | 0.213 | 0.000 |
| 16 | F1 | 1.608 | 0.044 | 0.109 | 2.828 |
| 22 | F1 | 13.454 | 1.129 | 0.182 | 0.409 |
| 25 | F1 | 0.737 | 0.155 | 0.102 | 0.000 |
| 26 | F1 | 2.549 | 0.173 | 0.362 | 0.020 |
| 32 | F1 | 20.821 | 0.847 | 0.177 | 0.509 |
| 33 | F1 | 22.706 | 0.000 | 0.308 | 0.000 |
| 38 | F1 | 1.057 | 0.166 | 0.254 | 0.042 |
| 40 | F1 | 2.107 | 0.737 | 0.191 | 0.000 |
| 41 | F1 | 4.807 | 0.162 | 0.082 | 0.000 |
| 46 | F1 | 9.254 | 0.105 | 0.354 | 0.129 |
| 48 | F1 | 1.091 | 0.164 | 0.192 | 0.061 |
| 56 | F1 | 3.668 | 0.071 | 0.182 | 0.019 |
| 65 | F1 | 1.772 | 0.292 | 0.334 | 0.073 |
| 66 | F1 | 4.993 | 0.142 | 0.184 | 0.107 |
| 69 | F1 | 3.719 | 0.742 | 0.142 | 0.000 |
| 74 | F1 | 2.403 | 0.142 | 0.333 | 0.133 |
| 83 | F1 | 10.411 | 0.124 | 0.302 | 0.000 |
| 86 | F1 | 15.137 | 0.211 | 0.248 | 0.080 |
| 88 | F1 | 3.117 | 0.271 | 0.159 | 0.000 |
| 91 | F1 | 9.190 | 0.157 | 0.120 | 0.195 |
| 95 | F1 | 4.925 | 0.221 | 0.092 | 0.082 |
| 98 | F1 | 4.141 | 0.236 | 0.144 | 0.000 |
| 105 | F1 | 2.858 | 0.307 | 0.121 | 0.000 |
| 107 | F1 | 6.845 | 0.697 | 0.225 | 0.000 |
| 109 | F1 | 3.411 | 0.352 | 0.149 | 0.000 |
| 113 | F1 | 4.362 | 0.269 | 0.122 | 0.076 |
| 116 | F1 | 2.523 | 0.176 | 0.525 | 0.000 |
| 125 | F1 | 0.000 | 0.000 | 0.037 | 0.000 |
| 126 | F1 | 47.177 | 0.153 | 0.115 | 0.027 |
| 134 | F1 | 1.548 | 0.112 | 0.056 | 0.000 |
| 135 | F1 | 6.409 | 0.000 | 0.074 | 0.133 |
| 139 | F1 | 1.075 | 0.072 | 0.130 | 0.000 |
| 141 | F1 | 0.486 | 0.230 | 0.163 | 0.140 |
| 143 | F1 | 2.114 | 0.235 | 0.093 | 0.036 |
| 144 | F1 | 0.717 | 0.266 | 0.093 | 0.040 |
| 145 | F1 | 26.723 | 0.356 | 0.273 | 0.000 |
| 146 | F1 | 18.831 | 0.027 | 0.028 | 0.000 |
| 151 | F1 | 0.454 | 0.000 | 0.132 | 0.035 |
| 152 | F1 | 4.112 | 0.121 | 0.084 | 0.022 |
| 153 | F1 | 0.045 | 0.100 | 0.092 | 0.000 |
| 154 | F1 | 2.042 | 0.286 | 0.091 | 0.021 |
| 155 | F1 | 0.776 | 0.203 | 0.148 | 0.063 |
| 157 | F1 | 0.032 | 0.249 | 0.135 | 0.157 |
| 159 | F1 | 3.249 | 0.166 | 0.246 | 0.055 |
| 161 | F1 | 8.785 | 0.529 | 0.062 | 0.055 |
| 163 | F1 | 6.892 | 0.184 | 0.128 | 0.025 |
| 164 | F1 | 5.502 | 0.155 | 0.126 | 0.000 |
| 165 | F1 | 4.377 | 0.050 | 0.059 | 0.074 |
| 167 | F1 | 2.121 | 0.233 | 0.187 | 0.086 |
| 169 | F1 | 1.357 | 0.271 | 0.053 | 0.109 |
| 170 | F1 | 1.659 | 0.444 | 0.079 | 0.027 |
| 171 | F1 | 23.344 | 0.109 | 0.136 | 0.057 |
| 172 | F1 | 30.169 | 9.747 | 0.106 | 0.037 |
| 175 | F1 | 1.279 | 0.126 | 0.136 | 0.055 |
| 178 | F1 | 20.252 | 0.336 | 0.160 | 0.037 |
| 182 | F1 | 2.235 | 0.173 | 0.067 | 0.057 |
| 189 | F1 | 4.098 | 0.117 | 0.247 | 0.000 |
| 210 | F1 | 1.537 | 0.119 | 0.111 | 0.032 |
| 214 | F1 | 1.129 | 0.117 | 0.214 | 0.036 |
| 216 | F1 | 0.060 | 0.108 | 0.047 | 0.093 |
| 217 | F1 | 0.664 | 0.256 | 0.091 | 0.089 |
| 219 | F1 | 4.317 | 0.050 | 0.140 | 0.057 |
| 223 | F1 | 0.892 | 0.072 | 0.166 | 0.107 |
| 224 | F1 | 1.329 | 0.131 | 0.163 | 0.027 |
| 226 | F1 | 0.380 | 0.232 | 0.180 | 0.146 |
| 227 | F1 | 0.369 | 0.415 | 0.100 | 0.000 |
| 229 | F1 | 1.297 | 0.057 | 0.221 | 0.000 |
| 235 | F1 | 1.061 | 0.141 | 0.119 | 0.066 |
| 240 | F1 | 1.619 | 0.324 | 0.186 | 0.000 |
| 241 | F1 | 1.553 | 0.310 | 0.064 | 0.016 |
| 243 | F1 | 10.520 | 0.114 | 0.098 | 0.093 |
| 244 | F1 | 4.056 | 0.134 | 0.252 | 0.069 |
| 245 | F1 | 0.785 | 0.018 | 0.058 | 0.064 |
| 246 | F1 | 5.979 | 0.211 | 0.187 | 0.071 |
| 247 | F1 | 1.945 | 0.107 | 0.094 | 0.109 |
| 248 | F1 | 18.063 | 0.238 | 0.039 | 0.000 |
| 249 | F1 | 1.125 | 0.242 | 0.091 | 0.000 |
| 250 | F1 | 0.572 | 0.288 | 0.076 | 0.187 |
| 257 | F1 | 0.000 | 0.215 | 0.091 | 0.000 |
| 263 | F1 | 1.479 | 0.058 | 0.052 | 0.034 |
| 264 | F1 | 8.456 | 0.164 | 0.211 | 0.071 |
| 265 | F1 | 1.333 | 0.312 | 0.039 | 0.000 |
| 269 | F1 | 0.000 | 0.099 | 0.079 | 0.058 |
| 273 | F1 | 0.588 | 0.405 | 0.063 | 0.084 |
| 275 | F1 | 0.182 | 0.061 | 0.029 | 0.000 |
| 276 | F1 | 0.760 | 0.198 | 0.049 | 0.000 |
| 277 | F1 | 0.000 | 0.093 | 0.082 | 0.000 |
| 285 | F1 | 0.280 | 0.218 | 0.096 | 0.099 |
| 286 | F1 | 0.653 | 0.316 | 0.111 | 0.107 |
| 297 | F1 | 0.681 | 0.255 | 0.085 | 0.236 |
| 305 | F1 | 0.298 | 0.279 | 0.033 | 0.064 |
| 337 | F1 | 0.133 | 0.301 | 0.031 | 0.067 |
| 338 | F1 | 0.467 | 0.165 | 0.038 | 0.036 |
| 339 | F1 | 0.405 | 0.349 | 0.089 | 0.125 |
| 340 | F1 | 0.771 | 0.367 | 0.201 | 0.041 |
| 351 | F1 | 0.237 | 0.075 | 0.089 | 0.000 |
| 357 | F1 | 2.042 | 0.419 | 0.060 | 0.049 |
| 361 | F1 | 0.332 | 0.242 | 0.049 | 0.000 |
| 2 | F2 | 6.409 | 0.309 | 0.486 | 0.265 |
| 6 | F2 | 68.832 | 2.918 | 0.343 | 0.114 |

TABLE 28-continued

Patient's BMK values for the genes CXCL6, IHH, IRF9 and MMP1 (Ct normalised using the $2^{-\Delta Ct}$ method)

| Patient | Status (F1 or F2) | CXCL6 | IHH | IRF9 | MMP1 |
|---|---|---|---|---|---|
| 7 | F2 | 5.579 | 0.182 | 0.132 | 0.000 |
| 10 | F2 | 4.790 | 0.000 | 0.374 | 0.000 |
| 12 | F2 | 16.622 | 0.405 | 0.285 | 0.862 |
| 13 | F2 | 1.035 | 0.057 | 0.131 | 0.000 |
| 14 | F2 | 2.181 | 0.207 | 0.092 | 0.000 |
| 17 | F2 | 1.474 | 0.257 | 0.399 | 0.000 |
| 20 | F2 | 3.745 | 0.137 | 0.168 | 0.096 |
| 23 | F2 | 3.784 | 0.278 | 0.294 | 0.150 |
| 27 | F2 | 6.727 | 0.049 | 0.125 | 0.115 |
| 28 | F2 | 8.664 | 0.323 | 0.219 | 0.000 |
| 31 | F2 | 13.642 | 0.719 | 0.310 | 0.104 |
| 34 | F2 | 3.668 | 0.261 | 0.086 | 0.000 |
| 39 | F2 | 4.028 | 0.616 | 0.206 | 0.000 |
| 42 | F2 | 1.003 | 0.345 | 0.129 | 0.000 |
| 43 | F2 | 6.892 | 0.150 | 0.134 | 0.000 |
| 44 | F2 | 2.266 | 0.264 | 0.326 | 0.122 |
| 45 | F2 | 6.298 | 1.028 | 0.339 | 0.463 |
| 50 | F2 | 2.979 | 0.491 | 0.219 | 0.103 |
| 55 | F2 | 5.426 | 0.075 | 0.149 | 0.000 |
| 58 | F2 | 6.233 | 0.422 | 0.358 | 0.000 |
| 60 | F2 | 11.713 | 0.667 | 0.269 | 0.000 |
| 63 | F2 | 3.053 | 0.144 | 0.283 | 0.236 |
| 67 | F2 | 3.618 | 0.000 | 0.115 | 0.126 |
| 72 | F2 | 5.187 | 0.514 | 0.064 | 0.225 |
| 75 | F2 | 9.221 | 0.174 | 0.497 | 0.000 |
| 76 | F2 | 13.177 | 0.648 | 0.276 | 0.074 |
| 80 | F2 | 3.681 | 0.120 | 0.119 | 0.193 |
| 87 | F2 | 12.906 | 0.216 | 0.388 | 0.053 |
| 90 | F2 | 7.781 | 0.478 | 0.247 | 0.000 |
| 92 | F2 | 0.624 | 0.200 | 0.083 | 0.000 |
| 97 | F2 | 1.469 | 0.199 | 0.136 | 0.024 |
| 114 | F2 | 11.081 | 0.416 | 0.963 | 0.000 |
| 148 | F2 | 7.621 | 0.140 | 0.132 | 0.072 |
| 160 | F2 | 10.483 | 0.171 | 0.167 | 0.055 |
| 166 | F2 | 0.511 | 0.000 | 0.020 | 0.000 |
| 168 | F2 | 2.313 | 0.209 | 0.093 | 0.113 |
| 174 | F2 | 9.918 | 0.418 | 0.241 | 0.081 |
| 176 | F2 | 10.375 | 0.347 | 0.127 | 0.049 |
| 177 | F2 | 2.219 | 0.127 | 0.228 | 0.112 |
| 179 | F2 | 5.483 | 0.158 | 0.214 | 0.028 |
| 185 | F2 | 1.753 | 0.148 | 0.091 | 0.021 |
| 194 | F2 | 5.696 | 0.184 | 0.198 | 0.079 |
| 213 | F2 | 2.878 | 0.081 | 0.272 | 0.080 |
| 218 | F2 | 3.506 | 0.107 | 0.149 | 0.031 |
| 225 | F2 | 3.352 | 0.056 | 0.095 | 0.109 |
| 232 | F2 | 47.340 | 0.074 | 0.208 | 0.000 |
| 237 | F2 | 41.499 | 0.197 | 0.190 | 0.000 |
| 239 | F2 | 6.190 | 0.247 | 0.219 | 0.000 |
| 279 | F2 | 0.412 | 0.088 | 0.047 | 0.051 |
| 294 | F2 | 0.150 | 0.262 | 0.084 | 0.090 |
| 298 | F2 | 0.000 | 0.253 | 0.023 | 0.107 |
| 325 | F2 | 0.622 | 0.768 | 0.136 | 0.000 |
| 333 | F2 | 1.185 | 0.250 | 0.115 | 0.250 |
| 343 | F2 | 0.712 | 0.220 | 0.081 | 0.000 |

2. Comparison of Measurement Values for the Sub-Populations F1 and F2 in Order to Set Up a Multivariate Classification Model The measurement values obtained in §1 above for the sub-populations F1 and F2 were compared in order to construct a multivariate classification model which, starting from the combination of these values, infers a hepatic fibrosis score.

A classification model may, for example, be obtained by following a multivariate statistical analysis method or a multivariate mathematical analysis method.

mROC Models:

A suitable multivariate mathematical analysis method is the mROC method (multivariate Receiver Operating Characteristic method).

By using the measurement values obtained in §1 above for the F1 and F2 sub-populations, mROC models were constructed as described in Kramar et al. 1999 and Kramar et al. 2001. To this end, the mROC version 1.0 software, available commercially from the designers (Andrew Kramar, Antoine Fortune, David Farragi and Benjamin Reiser), was used.

Andrew Kramar and Antoine Fortune may be contacted at or via the Unité de Biostatistique du Centre Régional de Lutte contre le Cancer (CRLC) [Biostatistics Unit, Regional Cancer Fighting Centre] Val d'Aurelle—Paul Lamarque (208, rue des Apothicaires; Parc Euromédecine; 34298 Montpellier Cedex 5; France).

David Faraggi and Benjamin Reiser may be contacted at or via the Department of Statistics, University of Haifa (Mount Carmel; Haifa 31905; Israel).

Starting from the input measurement data, the mROC method generates a decision rule in the form of a linear function $[Z=f(BMK_1, BMK_2, BMK_3, \ldots)]$ of the type $Z=\alpha.BMK_1+\beta.BMK_2+\gamma.BMK_3 \ldots$, where $BMK_1, BMK_2, BMK_3 \ldots$ are the measurement values for the levels of expression of each of the selected genes, and the user identifies the reference or threshold value ($\delta$) which provides this combination with the best performance.

This function and this threshold constitute a multivariate classification model.

The function $f$ calculated by the mROC method was then applied to the measurement values of the level of expression of the genes $BMK_1, BMK_2, BMK_3 \ldots$ measured for a test subject p. The value Z calculated for a test subject p was then compared with the threshold $\delta$.

For example, when the mean value of the combination of the levels of expression of said selected genes in the cohort "F2" is higher than that of the cohort of individuals "F1" (see graph at top of FIG. 2):

if $Z \geq \delta$, the test is positive ("pathological" subject): the subject p is declared to have a hepatic fibrosis score of F2;

if $Z < \delta$, the test is negative ("healthy" subject): the subject p is declared to have a hepatic fibrosis score of F1.

Conversely, when the mean value of the combination of the levels of expression of said selected genes in the cohort "F2" is lower than that of the cohort of "F1" individuals:

if $Z \geq \delta$, the test is negative ("healthy" subject): the subject p is declared to have a hepatic fibrosis score of F1; and if $Z < \delta$, the test is positive ("pathological" subject): the subject p is declared to have a hepatic fibrosis score of F2.

WKNN Models:

A suitable multivariate statistical analysis method is the WKNN (Weighted k Nearest Neighbours) method.

WKNN models were constructed as described by Hechenbichler and Schliep, 2004 using the measurement values obtained in §1 above for the sub-populations F1 and F2.

In outline, a WKNN method attributes each new case (y,x) to the class l of maximum weight in a neighbourhood of k neighbours in accordance with the formula:

$$l = max_r \left( \sum_{i=1}^{k} K(D(x, x_{(i)})) I(y_{(i)} = r) \right)$$

where r represents the index of the clinical classes of interest (in fact, the hepatic fibrosis score of F1 or F2), and is equal to 0 or 1.

In order to construct the WKNN models, R software (WKNN library), which is freely available from http://www.r-project.org/, was used. The following control parameters were used:
Kernel (K): epanechnikov;
Parameter of Minkowski distance (D): 2;
Number of neighbours (k): 3;
or
Kernel (K): triangular;
Parameter of Minkowski distance (D): 2;
Number of neighbours (k): 6;

The WKNN models constructed in this manner were then used to determine the hepatic fibrosis score of the subjects by inputting the measurement values for these subjects into the WKNN models constructed in this manner.

The measurement values for the levels of expression of the selected genes of a test subject p were compared with those of these neighbours (k). The WKNN model calculates the weight which has to be attributed to the "F1 score" class and that which has to be attributed to the "F2 score" for this subject p. The subject p is then classified by the WKNN model into the major class, (for example into the "F2 score" class if the weights of the F1 and F2 classes calculated by the WKNN method are 0.3 and 0.7 respectively).

Random Forest Models:

Random Forest or RF models were constructed using the measurement values obtained in §1 above for the F1 and F2 sub-populations as described in Breiman in 2001, Liaw and Wiener in 2002.

To this end, R software, which is freely available from http://www.r-project.org/, was used.

The following parameters were used:
NumberOfTrees=500;
NumberOfDescriptors=sqrt(D).

The digital data listed in the output file from R could be used to evaluate the signatures by calculating the following parameters: True Positive (TP), False Positive (FP), True Negative (TN) and False Negative (FN) (see below).

The data extracted from the output file for the RF models constructed thereby had the following form:
"OOB estimate of error rate: 34.18%
Confusion Matrix:

|    | NR | R  | Classification error |
|----|----|----|---------------------|
| NR | 71 | 31 | 0.3039216           |
| R  | 23 | 33 | 0.4107143           |

ROC score (out-of-bag data): 0.673"

OOB is the acronym for Out-Of-Bag, and represents an evaluation of the error.

These output data directly indicate the values for the parameters TP (number of F2 patients who have been classified as F2), FP (number of F1 patients who have been classified as F2), TN (number of F1 patients who have been classified as F1) and FN (number of F2 patients who have been classified as F1).

For the example presented above, it can be seen that:

TP=33;FP=31;FN=71 and FN=23

The formulae below are used to calculate the values for sensitivity (Se), specificity (Spe), positive predictive value (PPV), and negative predictive value (NPV):

$Se = TP/(TP+FN);$ $Sp = TN/(TN+FP);$ $PPV = TP/(TP+FP);$ $NPV = TN/(TN+FN).$

The output data also directly indicate the error rate and the ROC score of the constructed model.

The RF models constructed in this manner were then used to determine the hepatic fibrosis score of test subjects. The measurement values of the levels of expression of the genes of these test subjects were input into a RF model, which generated output data as presented above and classified the test subject into the "score F1" or "score F2" class.

Neural Network Models

Another appropriate method for multivariate statistical analysis is a neural network method. In brief, a neural network comprises an orientated weighted graph the nodes of which symbolize neurons. The network is constructed from sub-population measurement values (in this case F2 versus F1) and is then used to determine to which class (in this case F1 or F2) a new element (in this case a test patient p) belongs.

Neural network models were constructed as described by Intrator and Intrator 1993, Riedmiller and Braun 1993, Riedmiller 1994, Anastasiadis et al. 2005 using the measurement values obtained in §1 above for the F1 and F2 sub-populations; see http://cran.r-project.org/web/packages/neuralnet/index.html.

To this end, R software which is freely available from http://www.r-project.org/, was used (version 1.3 of Neuralnet, written by Stefan Fritsch and Frauke Guenther, following the work by Marc Suling).

The following computation options were used:
"NumberOfHiddenNodes=1 and 2
WeightDecayFactor=0.001
Cross Validate=True
Cross ValidationFolds=5
MaxNumberIterations=2000
MaxNumberWeights=2000".

For each of the combinations, the confusion matrix was extracted in the following format:
"Cross-Validation Results (5-Fold):

| Nodes | Decay | ROC    | Score Best |
|-------|-------|--------|------------|
| 1     | 1     | 0.001  | 0.7033     |
| 2     | 2     | 0.001  | 0.7305     | ***

Contingency Table (Best CV Model):

|        | Predicted |    |
|--------|-----------|----|
| Actual | F2        | F1 |
| F2     | 25        | 19 |
| F1     | 12        | 51 |

In this example, it will be observed that the best model is model 2, indicated by "***" in the "ScoreBest" column These output data directly indicate the values for the parameters TP (number of F2 patients who have been classified as F2), FP (number of F1 patients who have been classified as F2), TN (number of F1 patients who have been classified as F1) and FN (number of F2 patients who have been classified as F1). For the example presented above, it can be seen that:

TP=25;FP=12;FN=51 and FN=19

The evaluation parameters were computed: the sensitivity (Se), the specificity (Spe), the positive predictive value (PPV) and the negative predictive value (NPV) (see formulae for Se, Spe, PPV and NPV above).

The ROC score was extracted directly from the output file on the line identified by "***" which corresponded to the best model. The error was calculated by the following formula:

Class_err=(FP+FN)/(FP+TP+FN+TN).

The neural network models constructed thereby were then used to determine the hepatic fibrosis score of the test subjects. The measurement values for the levels of expression of the genes of these test subjects were entered into a neural network model which generated output data as presented above and classified the test subject into the "F1 score" or "F2 score" class.

3. Examples of Classification Models Obtained

The inventors thus identified the genes for which the levels of expression constitute biomarkers which, when taken in combination, are pertinent to determining the degree of hepatic fibrosis of a subject.

These genes are the following twenty-two genes: SPP1, A2M, VIM, IL8, CXCL10, ENG, IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1.

Particularly advantageously, it will be observed that these twenty-two genes are all genes coding for non-membrane proteins, i.e. genes which code for a protein with an intracellular and/or extracellular location and which is thus susceptible of being detected in a biological fluid of the subject such as the blood.

The inventors have further identified that the most pertinent combinations comprise all or some genes selected from a sub-group of six genes, namely SPP1, A2M, VIM, IL8, CXCL10 and ENG, more particularly:
  at least two genes from among SPP1, A2M and VIM, and
  at least one gene from among IL8, CXCL10 and ENG.

The inventors thus identified that particularly pertinent combinations comprise the combinations having the following characteristics:
  at least two genes from among SPP1, A2M and VIM,
  at least one gene from among IL8, CXCL10 and ENG,
  optionally at least one gene from among the following sixteen genes:
IL6ST, p14ARF, MMP9, ANGPT2, CXCL11, MMP2, MMP7, S100A4, TIMP1, CHI3L1, COL1A1, CXCL1, CXCL6, IHH, IRF9 and MMP1.

By way of illustration, examples of appropriate combinations of biomarkers in particular comprise 29 combinations of biomarkers (combinations of the levels of gene expression) presented in Table 3 above, in the description section.

Examples of classification models which may be used with these combinations of biomarkers are presented in:
  Tables 4, 5 and 8 above,
  Tables 6, 7 and 9 above,
  Tables 10 and 11 above,
  Tables 12 and 13 above,
(in fact, examples of mROC models).

Other examples of classification models may be constructed using the mROC method or another classification method (for example the WKNN or RF method or neural network method; see paragraph 2 above).

The predictive combinations of the invention are combinations of the levels of gene expression selected as indicated above.

However, it may be elected to involve one or more factors in these combinations other than the levels of expression of these genes, in order to combine this or these other factors and the levels of expression of the selected genes into one decision rule.

This or these other factors are preferably selected so as to construct a classification model the predictive power of which is further improved compared with the model which did not comprise this or these other factors.

This or these other factors may, for example, be clinical, biological, or virological factors, for example:
  one or more clinical factors, such as sex (feminine F or masculine M), age at the date of sampling (age at HBP), body mass index (BMI), insulin sensitivity index (HOMA), diabetes, alcohol consumption, degree of steatosis, mode of contamination, Metavir activity,
and/or
  one or more biological factors, such as concentration of haptoglobin (Hapto), concentration of apolipoprotein A1 (ApoA1), total quantity of bilirubin (BLT), concentration of gamma glutamyl transpeptidase (GGT), concentration of aspartate aminotransferase (AST), concentration of alanine aminotransferase (ALT), platelet count (PLQ), quantity of prothrombin (TP), quantity of HDL cholesterol (Chol-HDL), total quantity of cholesterol, concentration of ferritin (Ferritin), level of glycaemia (glycaemia), concentration of peptide C, quantity of insulin (insulinaemia), concentration of triglycerides (TG), quantity of albumin, transferrin saturation (TSAT), or concentration of alkaline phosphatase (ALP);
and/or
  one or more virological factors, such as viral genotype, duration of infection, viral load assayed for the patient at the treatment start date (viral load at D0), viral load assayed for the patient at the date of sampling (viral load at HBP).

Example 2

RNA from Hepatic Biopsy Puncture (HBP)/Applications of Constructed Models to Test Patients a) Example of Application of the Combination of the Levels of Expression (RNA) of the Genes A2M, SPP1, CXCL10, IL8 and S100A4 (Combination No. 16 in Table 3 Above)

The AUC relative to the combination of the levels of expression of the genes A2M, SPP1, CXCL10, IL8 and S100A4 computed for the complete study population of Example 1 (n=158 patients) is 0.783 (see Table 5 above).

Using the mROC method (see Example 1 above), the threshold maximizing the Youden's index ($\delta$) is 0.321 (see Table 5 above). In order to select this threshold, the performances of the combination are as follows: sensitivity (Se)=70%; specificity (Sp)=76% (see Table 5 above).

The following rule is an example of a decision rule:

$$Z = 0.360 \times A2M^t - 0.047 \times CXCL10 + 0.025 \times IL8 + 0.332 \times S100A4 + 0.272 \times SPP1^t$$

(function Z16ARN; see Table 4 above), where:
- A2M, CXCL10, IL8, S100A4 and SPP1 are the measurement values for the biomarkers BMK, i.e. the measurement values for the levels of expression of the indicated genes (in fact, the value of Ct normalised by the $2^{-\Delta Ct}$ method), and where
- the exponent t (carried here by A2M and SPP1) indicates that the value to be applied in the decision rule is the Box-Cox transformation (Box and Cox, 1964) of the measurement value of the level of expression (BMK) of the gene under consideration, in order to normalize it using the following formula:

$$BMK^t = (BMK^\lambda - 1)/\lambda.$$

In the example of a decision rule indicated above, the parameters λ are 0.33 for A2M and 0.12 for SPP1 (see Table 8 above).

If Z≥0.321: the diagnostic test is positive (mROC prediction=1), the subject is declared to be "F2".

If Z<0.321: the test is negative (mROC prediction=0), the subject is declared to be "F1".

An example of a prediction for 20 subjects (human patients) is given in Table 18 below, which presents the measurement values for the levels of expression of the selected genes (BMK values obtained by the $2^{-\Delta Ct}$ method; see Example 1 above).

One or more clinical, biological and virological factors may be combined with the five biomarkers indicated above (levels of expression of five genes), and lead to a decision rule the predictive power of which is much better than that of the rule presented above.

Tables 19 to 21 below present examples of such clinical, biological and virological factors, as well as their values for the test subjects of Table 18.

ND=not determined

TABLE 18

Example of application of a classification model based on the combination of the levels of expression of the genes A2M, SPP1, CXCL10, IL8 and S100A4 (combination No. 16 of Table 3 above)

| No. of test subject | Hepatic fibrosis score established by HBP | A2M | CXCL10 | IL8 | S100A4 | SPP1 | Z | mROC prediction |
|---|---|---|---|---|---|---|---|---|
| 8 | F1 | 4.141 | 1.297 | 0.000 | 0.821 | 0.050 | 0.179 | 0 |
| 9 | F1 | 1.495 | 2.078 | 0.625 | 0.979 | 0.071 | -0.220 | 0 |
| 16 | F1 | 1.352 | 0.000 | 1.237 | 1.083 | 0.105 | -0.032 | 0 |
| 22 | F1 | 1.676 | 0.346 | 6.791 | 0.451 | 0.133 | 0.019 | 0 |
| 38 | F1 | 1.347 | 2.780 | 0.967 | 0.877 | 0.143 | -0.174 | 0 |
| 40 | F1 | 2.151 | 4.857 | 0.423 | 0.478 | 0.117 | -0.260 | 0 |
| 41 | F1 | 1.653 | 0.333 | 1.264 | 0.880 | 0.277 | 0.181 | 0 |
| 48 | F1 | 0.509 | 2.567 | 1.805 | 0.821 | 0.100 | -0.569 | 0 |
| 69 | F1 | 1.664 | 0.509 | 2.936 | 0.471 | 0.223 | 0.032 | 0 |
| 74 | F1 | 2.063 | 1.765 | 5.772 | 0.507 | 0.067 | -0.104 | 0 |
| 177 | F2 | 5.389 | 2.378 | 0.825 | 0.877 | 0.146 | 0.543 | 1 |
| 179 | F2 | 6.476 | 2.799 | 3.246 | 0.563 | 0.262 | 0.730 | 1 |
| 194 | F2 | 6.892 | 0.920 | 2.131 | 0.422 | 0.088 | 0.548 | 1 |
| 213 | F2 | 6.105 | 3.758 | 14.082 | 0.660 | 0.241 | 0.929 | 1 |
| 218 | F2 | 6.298 | 1.390 | 2.276 | 0.719 | 0.406 | 0.910 | 1 |
| 225 | F2 | 3.127 | 2.166 | 5.396 | 1.025 | 0.129 | 0.378 | 1 |
| 232 | F2 | 8.969 | 5.187 | 8.744 | 0.920 | 0.599 | 1.304 | 1 |
| 237 | F2 | 7.701 | 0.605 | 1.224 | 0.605 | 0.201 | 0.855 | 1 |
| 239 | F2 | 4.423 | 3.084 | 2.604 | 0.238 | 0.296 | 0.382 | 1 |
| 343 | F2 | 4.213 | 1.873 | 7.357 | 0.470 | 0.238 | 0.556 | 1 |

TABLE 19

(clinical data):

| No. of subject | Sex | Age at HBP | BMI (kg/m2) | Insulin sensitivity index (HOMA) | Diabetes | Alcohol consumption (g/day) | Degree of steatosis | Mode of contamination | Metavir activity |
|---|---|---|---|---|---|---|---|---|---|
| 8 | F | 55 | 23 | 1.6 | No | 0 | 0 | Transfusion | 1 |
| 9 | M | 31 | 25 | 1.3 | No | 0 | 0 | ND | 1 |
| 16 | M | 34 | 23 | 0.8 | No | 0 | 0 | Nosocomial | 1 |
| 22 | F | 56 | 26 | 3.9 | No | 0 | 1 | Nosocomial | 1 |
| 38 | F | 45 | 27 | 1.5 | No | 30 | 0 | Toxicomania | 0 |
| 40 | F | 42 | 24 | 1.4 | No | 0 | 1 | Toxicomania | 1 |
| 41 | M | 49 | 26 | 2.2 | No | 0 | 1 | ND | 1 |
| 48 | F | 52 | 40 | 3.6 | Yes | 0 | 1 | ND | 1 |
| 69 | M | 48 | 23 | 1.3 | No | 0 | 0 | Toxicomania | 1 |
| 74 | F | 51 | 27 | 1.4 | No | 0 | 0 | ND | 1 |

TABLE 19-continued (clinical data):

| No. of subject | Sex | Age at HBP | BMI (kg/m2) | Insulin sensitivity index (HOMA) | Diabetes | Alcohol consumption (g/day) | Degree of steatosis | Mode of contamination | Metavir activity |
|---|---|---|---|---|---|---|---|---|---|
| 83 | F | 51 | 26 | ND | No | ND | 2 | ND | 1 |
| 177 | M | 51 | 26 | 1.6 | No | 10 | 1 | Toxicomania | 1 |
| 179 | M | 47 | 21 | 1.2 | No | 0 | 0 | Toxicomania | 1 |
| 194 | F | 62 | 19 | 1.3 | No | 0 | 0 | Transfusion | 1 |
| 213 | F | 68 | 40 | 1.5 | No | 0 | 1 | Nosocomial | 1 |
| 218 | M | 54 | 20 | 1.7 | No | 0 | 1 | Transfusion | 1 |
| 225 | M | 71 | 27 | 18.0 | Yes | 0 | 1 | ND | 2 |
| 232 | F | 57 | 35 | 4.1 | No | 0 | 2 | Transfusion | 1 |
| 237 | M | 68 | 24 | 0.8 | Yes | 0 | 0 | Nosocomial | 1 |
| 239 | F | 46 | 24 | 1.2 | No | 0 | 0 | Transfusion | 1 |
| 333 | F | 60 | 19 | ND | No | 0 | 1 | Transfusion | 1 |
| 343 | F | 19 | 22 | ND | No | 0 | 1 | Neo-natal | 1 |

TABLE 20

(virological data):

| No. of patient | Viral genotype | Duration of infection (years) | Viral load at HBP (copies/mL. $10^3$) |
|---|---|---|---|
| 8 | 1 | 24 | 3975 |
| 9 | 4 | ND | 1509 |
| 16 | 4 | ND | 179 |
| 22 | 1 | 33 | 1116 |
| 38 | 1 | 17 | 5641 |
| 40 | 3 | 21 | 1823 |
| 41 | 4 | ND | 8286 |
| 48 | 2 | ND | 4911 |
| 69 | 1 | 25 | 13267 |
| 74 | 4 | ND | 2101 |
| 83 | 1 | ND | 1579 |
| 177 | 1 | 23 | 4743 |
| 179 | 4 | 25 | 5986 |
| 194 | 1 | 24 | 5051 |
| 213 | 1 | 41 | 2677 |
| 218 | 1 | 24 | 3706 |
| 225 | 3 | ND | 5406 |
| 232 | 1 | 18 | 2117 |
| 237 | 1 | ND | 1408 |
| 239 | 1 | 22 | 2476 |
| 333 | 1 | 40 | 2383 |
| 343 | 1 | ND | 305 |

TABLE 21

(biological data):

| No. of subject | A2M (g/L) | Hapto (g/L) | Apo A1 (g/L) | BLT (µmole/L) | GGT (U/L) | AST (U/L) | ALT (U/L) | PLQ (×$10^3$/mm$^3$) | TP (%) | Chol-HDL (mmole/L) |
|---|---|---|---|---|---|---|---|---|---|---|
| 8 | 3.13 | 1.29 | 1.63 | 7 | 28 | 60 | 98 | 293 | 100 | 1.27 |
| 9 | 1.84 | 0.92 | 1.58 | 12 | 82 | 40 | 63 | 209 | 100 | 1.28 |
| 16 | 2.57 | 0.82 | 1.42 | 11 | 34 | 78 | 157 | 186 | 100 | 1.08 |
| 22 | 3.52 | 0.93 | 2 | 14 | 50 | 74 | 119 | 175 | 95 | 0.66 |
| 38 | 1.78 | 0.93 | 2.24 | 10 | 70 | 33 | 42 | 265 | 100 | 1.89 |
| 40 | 1.69 | 0.86 | 1.99 | 6 | 22 | 43 | 79 | 288 | 100 | 0.58 |
| 41 | 2.83 | 1.8 | 1.37 | 20 | 23 | 35 | 64 | 207 | 93 | 1.1 |
| 48 | 1.78 | 1.83 | 2.01 | 11 | 53 | 32 | 48 | 270 | 100 | 1.95 |
| 69 | 2.41 | 1.81 | 1.66 | 9 | 30 | 40 | 64 | 224 | 100 | 1.27 |
| 74 | 1.72 | 1.08 | 1.51 | 16 | 25 | 43 | 40 | 211 | 91 | 1.49 |
| 83 | ND | ND | ND | 13 | 82 | 78 | 95 | 232 | 101 | ND |
| 177 | 4.14 | 0.97 | 1.49 | 14 | 153 | 41 | 76 | 210 | 102 | 1.06 |
| 179 | 3.26 | 0.36 | 1.4 | 13 | 105 | 34 | 36 | 217 | 100 | 1.27 |
| 194 | 3.5 | 0.82 | 1.75 | 10 | 24 | 72 | 94 | 157 | 92 | 1.55 |
| 213 | 3.7 | 0.23 | 1.82 | 11 | 102 | 71 | 89 | 246 | 96 | 1.35 |
| 218 | 2.99 | 0.45 | 1.67 | 18 | 47 | 25 | 41 | 194 | 90 | 1.46 |
| 225 | 3.6 | 0.47 | 1.64 | 13 | 64 | 52 | 49 | 268 | 96 | 1.17 |
| 232 | 3.23 | 0.95 | 2.09 | 8 | 90 | 115 | 212 | 196 | 97 | 1.86 |
| 237 | 2.63 | 1.21 | 1.66 | 14 | 24 | 44 | 49 | 226 | 98 | 1.44 |
| 239 | 2.56 | 0.98 | 2.62 | 9 | 47 | 103 | 164 | 291 | 100 | 2.49 |
| 333 | 3.38 | 0.63 | 1.44 | 16 | 51 | 119 | 191 | 159 | 100 | ND |
| 343 | 2.69 | 0.65 | 1.44 | 17 | 22 | 26 | 38 | 332 | 92 | ND |

TABLE 21-continued (biological data):

| No. of subject | Ferritin (µg/L) | Glycaemia (mmole/L) | Peptide C (ng/mL) | Insulin (µUI/mL) | TG (mmole/L) | Albumin (g/L) | TSAT (%) | Total cholesterol (mmole/L) | ALP (U/L) |
|---|---|---|---|---|---|---|---|---|---|
| 8 | ND | 5 | 1.94 | 7.1 | 0.99 | 47 | ND | 5.4 | 69 |
| 9 | 99 | 4.5 | 1.9 | 6.7 | 1.04 | 48 | 59 | 4.4 | 59 |
| 16 | 101 | 5 | 1.2 | 3.5 | 1.49 | 59 | 19 | 4.8 | 61 |
| 22 | 390 | 5.2 | 3.2 | 16.7 | 0.8 | 44 | 27 | 3.7 | 93 |
| 38 | 39 | 5.4 | 1.9 | 6.1 | 0.76 | 43 | 30 | 5.4 | 58 |
| 40 | 24 | 4.4 | 1.7 | 7.1 | 1.19 | 45 | 17 | 4.7 | 49 |
| 41 | 178 | 4.7 | 2.6 | 10.3 | 1 | 42 | 37 | 5.0 | 56 |
| 48 | 92 | 6.7 | 2.33 | 12.0 | 0.66 | 42 | 19 | 6.5 | 173 |
| 69 | 178 | 4.2 | 1.99 | 6.8 | 1.74 | 57 | 35 | 7.2 | 61 |
| 74 | 14 | 3 | 1.89 | 10.2 | 0.86 | 45 | 17 | 5.3 | 55 |
| 83 | 71 | 5.6 | ND | ND | 0.76 | 44 | 37 | 3.68 | 97 |
| 177 | 339 | 4.8 | 2.29 | 7.6 | 0.76 | 46 | 46 | 4.7 | 36 |
| 179 | 41 | 4.8 | 1.77 | 5.7 | 0.39 | 48 | 15 | 3.3 | 57 |
| 194 | 129 | 4.3 | 1.66 | 6.7 | 0.91 | 48 | 38 | 5.2 | 33 |
| 213 | 172 | 4.6 | 1.93 | 7.5 | 0.73 | 42 | 30 | 3.3 | 83 |
| 218 | 156 | 5.6 | 2.35 | 6.7 | 1.03 | 40 | 48 | 4.3 | 44 |
| 225 | 26 | 14.5 | 4.39 | 27.9 | 1.01 | 48 | 16 | 4.6 | 93 |
| 232 | 399 | 5 | 4.73 | 18.6 | 0.98 | 42 | 28 | 4.9 | 64 |
| 237 | 20 | 8.3 | 0.73 | 2.3 | 0.85 | 41 | 29 | 5.0 | 58 |
| 239 | 170 | 4.6 | 1.81 | 5.6 | 0.93 | 50 | 29 | 6.6 | 97 |
| 333 | 259 | 4.5 | ND | ND | 1.26 | 51 | 42 | 4.5 | 96 |
| 343 | 305 | 4.3 | ND | ND | ND | 44 | 29 | ND | 41 | b) Example of Application of the Combination of the Levels of Expression (RNA) of the Genes A2M, CXCL10, IL8, SPP1 and VIM (Combination No. 4 in Table 3 Above)

The AUC relative to the combination of the levels of expression of the genes A2M, CXCL10, IL8, SPP1 and VIM computed for the complete study population of Example 1 (n=158 patients) is 0.787 (see Table 5 above). Using the mROC method (see Example 1), the threshold maximizing the Youden's index (δ) for this combination is −0.764 (see Table 5 above). In order to select this threshold, the performances of the combination are as follows: Sensitivity (Se) =75%; specificity (Spe)=70% (see Table 5 above).

The following rule is an example of a decision rule:

$$Z = 0.297 \times A2M^t - 0.046 \times CXCL10 + 0.020 \times IL8 + 0.274 \times SPP1^t + 0.253 \times VIM^t$$

(function Z4ARN; see Table 4 above), where:
A2M, CXCL10, IL8, SPP1 and VIM are the measurement values for the biomarkers BMK, i.e. the measurement values for the levels of expression of the indicated genes (in fact, the value of Ct normalised by the method $2^{-\Delta Ct}$), and
the exponent t (carried here by A2M, SPP1 and VIM) indicates that the value to be applied in the decision rule is the Box-Cox transformation (Box and Cox, 1964) of the measurement value of the level of expression (BMK) of the gene under consideration, in order to normalize it using the following formula: $BMK^t = (BMK^\lambda - 1)/\lambda$.

In the example of a decision rule indicated above, the parameters λ are 0.33 for A2M, 0.12 for SPP1 and −0.23 for VIM (see Table 8 above).

If Z≥−0.764: the diagnostic test is positive (mROC prediction=1), the subject is declared to be "F2".

If Z<−0.764: the test is negative (mROC prediction=0), the subject is declared to be "F1".

An example of a prediction for 20 subjects (human patients) is given in Table 22 below, which presents the measurement values for the levels of expression of the selected genes (BMK values obtained by the method $2^{-\Delta Ct}$; see Example 1 above).

One or more clinical, biological and virological factors may be combined with the five markers indicated above (levels of expression of five genes), and lead to a decision rule the predictive power of which is much better than that of the rule presented above.

Tables 19 to 21 above present examples of such clinical, biological and virological factors, as well as their values for the test patients of Table 22.

TABLE 22

Example of application of a classification model based on the combination of the levels of expression of the genes A2M, CXCL10, IL8, SPP1 and VIM (combination No. 4 of Table 3 above)

| | Hepatic fibrosis | mROC model (threshold = −0.764) | | | | | | |
|---|---|---|---|---|---|---|---|---|
| No. of test subject | score established by HBP | A2M | CXCL10 | IL8 | SPP1 | VIM | Z | mROC prediction |
| 8 | F1 | 4.141 | 1.297 | 0.000 | 0.050 | 0.170 | −0.764 | 0 |
| 9 | F1 | 1.495 | 2.078 | 0.625 | 0.071 | 0.117 | −1.281 | 0 |
| 16 | F1 | 1.352 | 0.000 | 1.237 | 0.105 | 0.120 | −1.112 | 0 |
| 38 | F1 | 1.347 | 2.780 | 0.967 | 0.143 | 0.177 | −1.029 | 0 |

TABLE 22-continued

Example of application of a classification model based on the combination of the levels of expression of the genes A2M, CXCL10, IL8, SPP1 and VIM (combination No. 4 of Table 3 above)

| No. of test subject | Hepatic fibrosis score established by HBP | mROC model (threshold = −0.764) | | | | | | |
|---|---|---|---|---|---|---|---|---|
| | | A2M | CXCL10 | IL8 | SPP1 | VIM | Z | mROC prediction |
| 40 | F1 | 2.151 | 4.857 | 0.423 | 0.117 | 0.142 | −1.100 | 0 |
| 41 | F1 | 1.653 | 0.333 | 1.264 | 0.277 | 0.129 | −0.815 | 0 |
| 48 | F1 | 0.509 | 2.567 | 1.805 | 0.100 | 0.119 | −1.510 | 0 |
| 69 | F1 | 1.664 | 0.509 | 2.936 | 0.223 | 0.068 | −1.116 | 0 |
| 74 | F1 | 2.063 | 1.765 | 5.772 | 0.067 | 0.119 | −1.049 | 0 |
| 83 | F1 | 2.959 | 6.255 | 4.918 | 0.156 | 0.166 | −0.821 | 0 |
| 177 | F2 | 5.389 | 2.378 | 0.825 | 0.146 | 0.102 | −0.654 | 1 |
| 179 | F2 | 6.476 | 2.799 | 3.246 | 0.262 | 0.087 | −0.462 | 1 |
| 194 | F2 | 6.892 | 0.920 | 2.131 | 0.088 | 0.123 | −0.456 | 1 |
| 213 | F2 | 6.105 | 3.758 | 14.082 | 0.241 | 0.089 | −0.335 | 1 |
| 218 | F2 | 6.298 | 1.390 | 2.276 | 0.406 | 0.134 | −0.148 | 1 |
| 232 | F2 | 8.969 | 5.187 | 8.744 | 0.599 | 0.177 | 0.218 | 1 |
| 237 | F2 | 7.701 | 0.605 | 1.224 | 0.201 | 0.053 | −0.599 | 1 |
| 239 | F2 | 4.423 | 3.084 | 2.604 | 0.296 | 0.113 | −0.547 | 1 |
| 333 | F2 | 8.282 | 6.589 | 7.291 | 0.014 | 0.168 | −0.716 | 1 |
| 343 | F2 | 4.213 | 1.873 | 7.357 | 0.238 | 0.189 | −0.267 | 1 | c) Combination of the Levels of Expression (RNA) of the Genes A2M, CXCL10, IL8, SPP1 and S100A4 (Combination No. 16 in Table 3 Above), Additionally Combined with a Clinical Factor and with Biological Factors One or more clinical factors and/or one or more biological factors and/or one or more virological factors may be combined with the levels of expression of genes selected in accordance with the invention (in fact, levels of RNA transcription measured in a HBP sample), and thus lead to a decision rule the predictive power of which is much better than that of the simple combination of said levels of expression.

For example, the combination:
of the levels of expression (RNA) of the genes A2M, CXCL10, IL8, SPP1 and S100A4 (combination No. 16 in Table 3 above; see Example 2a above) assayed for the RNA of a HBP sample,
of the value of the clinical factor "age at the date of sampling" (Age), in fact age at the date of HBP, and
the values for the following (other) biological factors:
  concentration of triglycerides (TG; protein concentration in the serum),
  concentration of alanine aminotransferase (ALT; protein concentration in the serum),
  concentration of ferritin (Ferritin; protein concentration in the serum),
leads to a decision rule the area under the ROC curve of which (AUC), computed for the complete study population of Example 1 (n=158 patients), is 0.840 (although it is 0.783 when the combination of the levels of expression of the genes A2M, CXCL10, IL8, SPP1 and S100A4 is used alone, without being combined with the clinical factor and other biological factors indicated above).

Using the mROC method (see Example 1), the threshold maximizing the Youden's index ($\delta$) for this combination is 8.014 (see Table 11 above).

In order to select this threshold, the performances of the combination are as follows:
Sensitivity (Se)=72%; specificity (Spe)=82% (see Table 11 above).

The following rule is an example of a decision rule:

$$Z = 0.272 \times A2M^t - 0.032 \times CXCL10 + 0.058 \times IL8 + 0.419 \times SPP1^t + 0.012 \times S100A4^t + 0.025 \times Age^t + 0.566 \times TG^t + 3.874 \times ALT^t - 0.039 \times Ferritin^t$$

(function Z16ARNsupp; see Table 10 above), where:
A2M, CXCL10, IL8, SPP1 and S100A4 are the measurement values BMK for the biomarkers, i.e. the measurement values for the levels of expression of the indicated genes (in fact, the value of Ct normalised by the method $2^{-\Delta Ct}$) assayed for the RNA of a HBP sample,
Age is the age of the patient at the date of sampling,
TG, ALT, and Ferritin are the values for the biological factors indicated (protein concentrations in the serum), and
the exponent t (carried here by A2M, SPP1, S100A4, Age, TG, ALT and Ferritin) indicates that the value to be applied in the decision rule is the Box-Cox transformation (Box and Cox, 1964) of the measurement value of the level of expression (BMK) of the gene under consideration, in order to normalize it using the following formula:

$$BMK^t = (BMK^\lambda - 1)/\lambda.$$

In the example of a decision rule indicated above, the parameters $\lambda$ are 0.21 for A2M, 0.04 for SPP1, 0.48 for S100A4, 0.79 for Age, −0.22 for TG, −0.41 for ALT and 0.15 for Ferritin (see Table 11 above).

If Z≥8.014: the diagnostic test is positive (mROC prediction=1), the subject is declared to be "F2".

If Z<8.014: the test is negative (mROC prediction=0), the subject is declared to be "F1".

d) Combination of the Levels of Expression (RNA) of the Genes A2M, CXCL10, IL8, SPP1 and VIM (Combination No. 4 in Table No. 3 Above), Additionally Combined with Biological Factors One or more clinical factors and/or one or more biological factors and/or one or more virological factors may be combined with the levels of expression of genes selected in accordance with the invention (in fact, levels of RNA transcription measured in a HBP sample), and thus lead to a decision rule the predictive power of which is much better than that of the simple combination of said levels of expression.

For example, the combination:
of the levels of expression (RNA) of the genes A2M, CXCL10, IL8, SPP1 and VIM (combination No. 4 in Table 3 above; see Example 2b above) (in fact, the value of Ct normalised by the method $2^{-\Delta Ct}$) assayed for the RNA of a HBP sample, and the values for the following (other) biological factors:
concentration of triglycerides (TG; protein concentration in the serum),
concentration of alanine aminotransferase (ALT; protein concentration in the serum),
concentration of gamma glutamyl transpeptidase (GGT; protein concentration in the serum),
concentration of ferritin (Ferritin; protein concentration in the serum), leads to a decision rule the area under the ROC curve of which (AUC), computed for the complete study population of Example 1 (n=158 patients), is 0.841 (as opposed to 0.787 when the combination of the levels of expression of the genes A2M, CXCL10, IL8, SPP1 and VIM is used alone, without being combined with the other biological factors indicated above).

Using the mROC method (see Example 1), the threshold maximizing the Youden's index for this combination is 7.016 (see Table 11 above).

In order to select this threshold, the performances of the combination are as follows:

Sensitivity (Se)=80%; specificity (Spe)=71% (see Table 11 above).

The following rule is an example of a decision rule:

$Z=0.315 \times A2M^t - 0.043 \times CXCL10 + 0.058 \times IL8 + 0.383 \times SPP1^t + 0.064 \times VIM^t + 0.56 \times TG^t + 3.657 \times ALT^t + 0.188 \times GGT^t - 0.05 \times \text{Ferritin}^t$ (function Z4ARNsupp; see Table 10 above), where:
A2M, CXCL10, IL8, SPP1 and VIM are the measurement values BMK for the biomarkers, i.e. the measurement values for the levels of expression of the indicated genes (in fact, the value of Ct normalised by the method $2^{-\Delta Ct}$) assayed for the RNA of a HBP sample,
TG, ALT, GGT and Ferritin are the values for the biological factors indicated (protein concentrations in the serum), and the exponent t (carried here by A2M, SPP1, VIM, TG, ALT, GGT and Ferritin) indicates that the value to be applied in the decision rule is the Box-Cox transformation (Box and Cox, 1964) of the measurement value of the level of expression (BMK) of the gene under consideration, in order to normalize it using the following formula:

$BMK^t = (BMK^\lambda - 1)/\lambda$.

In the example of a decision rule indicated above, the parameters λ are 0.21 for A2M, 0.04 for SPP1, −0.26 for VIM, −0.22 for TG, −0.41 for ALT, −0.12 for GGT and 0.15 for Ferritin (see Table 11 above).

If Z≥7.016: the diagnostic test is positive (mROC prediction=1), the subject is declared to be "F2".

If Z<7.016: the test is negative (mROC prediction=0), the subject is declared to be "F1".

Example 3

Seric Proteins/Constructions of Models and Applications to Test Patients a) Example of Construction of a Multivariate Classification Model from the Combination of the Levels of Seric Expression of the Proteins A2M, SPP1, CXCL10, IL8 and S100A4 (Combination No. 16 in Table 3 Above)

The levels of expression of the proteins A2M, SPP1, CXCL10, IL8 and S100A4 were measured in the serum of 228 patients who, according to the analysis of a HBP taken from each of these patients, presented as follows:

for 149 of them: a fibrosis score of F2 using the Metavir fibrotic score system (F2 cohort),
for 79 of them: a fibrosis score of F1 using the Metavir fibrotic score system (F1 cohort).

The protein measurements were carried out using the kits indicated in Table 29 above, following the recommendations of the manufacturer.

TABLE 29

Kits for protein measurements

| Markers | A2M (Alpha-2-Macroglobulin) | CXCL10/IP10 | CXCL8/IL-8 | SPP1 (osteopontin) | S100A4 |
|---|---|---|---|---|---|
| EIA kit | Human alpha2-Macroglobulin ELISA Quantification Kit | Quantikine Human CXCL10/IP10 Immunoassay | Quantikine Human CXCL8/IL-8 Immunoassay | Quantikine Human Osteopontin (OPN) Immunoassay | S100A4 ELISA Kit Circulex |
| Supplier | GenWay | R&D Systems | R&D Systems | R&D Systems | MBL International |
| Reference | 40-288-20008F | DIP100 | D8000C | DOST00 | CY-8059 |
| Type of ELISA | Sandwich | Sandwich | Sandwich | Sandwich | Sandwich |
| Sample types | Serum or other biological liquids | Serum, plasma, saliva, cell culture medium | Serum, plasma, cell culture medium | Cell culture supernatant, breast milk, urine and plasma | Cell extract, tissue culture medium and other biological media |
| Sample volume | 100 μL (dilution 1/10000) | 75 μL | 50 μL | 50 μL (dilution 1/25) | 100 μL (dilution -> 1/6) |
| Solid phase | anti-A2M PAb from rabbit | anti-IP10 MAb | anti-IL8 MAb | anti-SPP1 MAb | anti-S100A4 PAb |
| Conjugate | anti-A2M PAb-HRP from rabbit | anti-IP10 PAb-HRP | anti-IL8 PAb-HRP | anti-SPP1 PAb-HRP | anti-S100A4 PAb-HRP |
| Sensitivity | 2.7 ng/mL | 1.67 pg/mL | 3.5 pg/mL | 0.011 ng/mL | 0.24 ng/mL |

TABLE 29-continued

Kits for protein measurements

| Markers | A2M (Alpha-2-Macroglobulin) | CXCL10/IP10 | CXCL8/IL-8 | SPP1 (osteopontin) | S100A4 |
|---|---|---|---|---|---|
| Detection range | 2.7-2000 ng/mL | 7.8-500 pg/mL | 31.2-2000 pg/mL | 0.312-20 ng/mL | 0.78-50 ng/mL |
| Specificity | human A2M | IP10 native and recombinant, no cross reaction with BLC/BCA-1, ENA-78, GCP-2, GROa, GROg, IFN-g, IL-8, IL-8 (endothelial cell-derived), I-TAC, MIG, NAP-2, SDF-1a, SDF-1b human recombinant, BLC/BCA-1, CRG-2 (IP-10), GCP-2, KC, MIG, SDF-1a mouse recombinant and Il-8 pig recombinant | IL8 human and recombinant, no cross reaction with ANG, AR, CNTF, b-ECGF, EGF, Epo, FGF acid, FGF basic, FGF-4, FGF-5, FGF-6, G-CSF, GM-CSF, GROa, GROb, GROg, sgp130, HB-EGF, HGF, I-309, IFN-g, IGF-I, IGF-II, IL-1a, IL-1b, IL-1ra, IL-1 sRI | Osteopontin native and recombinant, no cross reaction with human enterokinase, MMP-3, MMP-7, thrombin and with mouse and bovine osteopontin | S100A4, no cross reaction with S100P, S100A12 |

PAb = polyclonal antibody
MAb = monoclonal antibody

Figure 5:
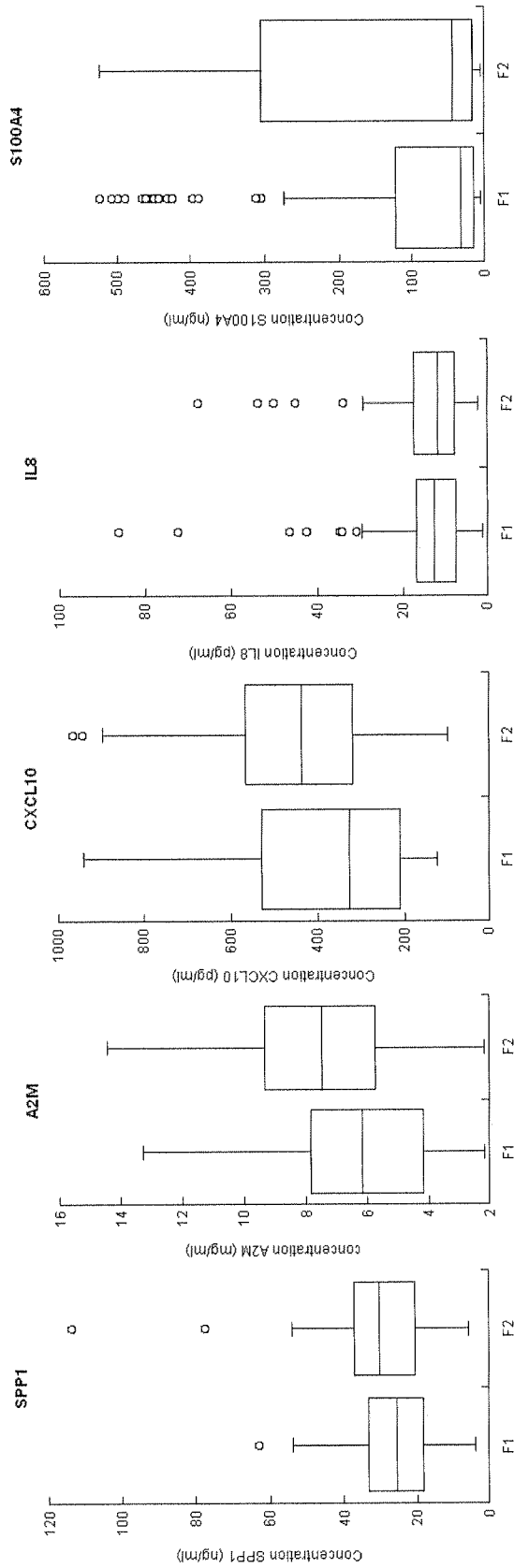
FIG. 5: Distribution of seric concentrations of the proteins A2M, CXCL10, IL8, SPP1 and S100A4 (see Example 3).

The distribution of the seric concentrations of the proteins A2M, SPP1, CXCL10, IL8 and S100A4 as a function of the hepatic fibrosis score is presented in FIG. 5.

The AUC relative to the combination of the levels of expression of the proteins A2M, SPP1, CXCL10, IL8 and S100A4 computed over the population of the study of 228 patients is 0.694 (see Table 7 above).

Using the mROC method (see Example 1), the threshold maximizing the Youden's index for this combination is 2.905 (see Table 7 above).

In order to select this threshold, the performances of the combination are as follows:

Sensitivity (Se)=68%; specificity (Spe)=67% (see Table 7 above).

The following rule is an example of a decision rule:

$$Z = 0.241 \times A2M^t + 0.137 \times CXCL10^t + 0.001 \times IL8^t + 0.062 \times SPP1^t + 0.226 \times S100A4^t$$

(function Z16PROT; see Table 6 above), where:
  A2M, CXCL10, IL8, SPP1 and S100A4 are the measurement values BMK for the biomarkers, i.e. the measurement values for the levels of expression of the indicated genes (in fact, concentration of proteins in the serum), and
  the exponent t (carried here by A2M, CXCL10, IL8, SPP1 and S100A4) indicates that the value to be applied in the decision rule is the Box-Cox transformation (Box and Cox, 1964) of the measurement value of the level of expression (BMK) of the gene under consideration, in order to normalize it using the following formula:

$$BMK^t = (BMK^\lambda - 1)/\lambda.$$

In the example of a decision rule indicated above, the parameters $\lambda$ are 0.46 for A2M, 0.08 for CXCL10, 0.05 for IL8, 0.43 for SPP1 and −0.15 for S100A4 (see Table 9 above).

If $Z \geq 2.905$, the diagnostic test is positive (mROC prediction=1), the subject is declared to be "F2".

If $Z < 2.905$, the test is negative (mROC prediction=0), the subject is declared to be "F1".

An example of a prediction for 20 subjects (human patients) is given in Table 19 below, which presents the measurement values (BMK) for the seric levels of expression of the selected genes.

One or more clinical factors and/or one or more biological factors and/or one or more virological factors may be combined with the seric levels of expression of proteins selected in accordance with the invention, and lead to a decision rule the predictive power of which may be much better than that of the rule presented above.

Tables 19 to 21 above present examples of such clinical, biological and virological factors, as well as their values for the test patients of Table 23.

TABLE 23

Example of application of a classification model based on the combination of the seric levels of expression of the genes A2M, CXCL10, IL8, SPP1 and S100A4 (combination No. 16 of Table 3 above)

| | Hepatic fibrosis score | mROC model (threshold = 2.905) | | | | | | |
|---|---|---|---|---|---|---|---|---|
| No. of test subject | established by HBP | A2M (mg/mL) | CXCL10 (pg/mL) | SPP1 (ng/mL) | IL8 (pg/mL) | S100A4 (ng/mL) | Z | mROC prediction |
| 9 | F1 | 4.21 | 317.93 | 28.8 | 5.34 | 14.0420 | 2.4553 | 0 |
| 11 | F1 | 4.02 | 461.77 | 51 | 23.72 | 53.3067 | 2.8731 | 0 |
| 18 | F1 | 4 | 846.53 | 26.1 | 8.16 | 10.9538 | 2.5901 | 0 |
| 21 | F1 | 4.09 | 306.3 | 45.3 | 6.18 | 105.0504 | 2.8299 | 0 |
| 22 | F1 | 4.04 | 529.67 | 46.1 | 9.29 | 54.8824 | 2.8752 | 0 |
| 26 | F1 | 7.25 | 150.84 | 27.9 | 10.13 | 9.0630 | 2.5111 | 0 |
| 32 | F1 | 3.2 | 149.56 | 10.6 | 6.46 | 500.0294 | 2.3834 | 0 |

TABLE 23-continued

Example of application of a classification model based on the combination of the seric levels of expression of the genes A2M, CXCL10, IL8, SPP1 and S100A4 (combination No. 16 of Table 3 above)

| No. of test subject | Hepatic fibrosis score established by HBP | mROC model (threshold = 2.905) | | | | | | |
|---|---|---|---|---|---|---|---|---|
| | | A2M (mg/mL) | CXCL10 (pg/mL) | SPP1 (ng/mL) | IL8 (pg/mL) | S100A4 (ng/mL) | Z | mROC prediction |
| 35 | F1 | 3.05 | 241.65 | 29.2 | 34.83 | 19.5252 | 2.3126 | 0 |
| 38 | F1 | 2.93 | 419.56 | 31.3 | 3.65 | 265.5756 | 2.7441 | 0 |
| 40 | F1 | 2.16 | 660.26 | 26.7 | 3.93 | 70.2605 | 2.5494 | 0 |
| 2 | F2 | 9.19 | 268.86 | 29.9 | 7.87 | 127.2983 | 3.1541 | 1 |
| 6 | F2 | 14.45 | 564.09 | 53.4 | 7.87 | 8.4328 | 3.4643 | 1 |
| 10 | F2 | 5.02 | 692.35 | 34.4 | 5.9 | 41.7101 | 2.9172 | 1 |
| 17 | F2 | 7.16 | 430.95 | 39 | 7.87 | 44.3571 | 3.0504 | 1 |
| 23 | F2 | 13.8 | 338.51 | 38.3 | 16.07 | 93.5798 | 3.5387 | 1 |
| 27 | F2 | 6.79 | 522 | 45.6 | 18.62 | 85.1345 | 3.1905 | 1 |
| 28 | F2 | 7.14 | 643.05 | 27.7 | 10.13 | 392.9496 | 3.2816 | 1 |
| 43 | F2 | 6.19 | 557.47 | 51.9 | 16.92 | 492.5924 | 3.3739 | 1 |
| 44 | F2 | 8.21 | 496.77 | 45.4 | 20.89 | 19.3361 | 3.1003 | 1 |
| 50 | F2 | 9.15 | 403.28 | 22.7 | 8.44 | 303.4538 | 3.2592 | 1 | b) Combination of the Levels of Expression in the Serum of the Proteins A2M, CXCL10, IL8, SPP1 and S100A4 (Combination No. 16 in Table 3 Above), Additionally Combined with a Clinical Factor and with Biological Factors One or more clinical factors and/or one or more biological factors and/or one or more virological factors may be combined with the seric levels of expression of genes selected in accordance with the invention (seric proteins), and thus lead to a decision rule the predictive power of which is much better than that of the simple combination of said seric levels of expression.

For example, the combination:

of the seric levels of translation of the genes A2M, CXCL10, IL8, SPP1 and S100A4 (see Example 3a; combination No. 16 in Table 3 above), of the value for the clinical factor "age at the date of sampling", in fact age at the date of taking the serum (Age), and the values for the following (other) biological factors:

concentration of triglycerides (TG; protein concentration in the serum), concentration of alanine aminotransferase (ALT; protein concentration in the serum), concentration of gamma glutamyl transpeptidase (GGT; protein concentration in the serum), leads to a decision rule the area under the ROC curve of which (AUC), computed for the complete study population of Example 3a (n=228 patients), is 0.743 (although it is 0.694 when the combination of the seric levels of translation of the genes A2M, CXCL10, IL8, SPP1 and S100A4 is used alone, without being combined with the clinical factor and other biological factors indicated above; see Example 3a) above).

Using the mROC method (see Example 1), the threshold maximizing the Youden's index for this combination is 8.792 (see Table 13 above).

In order to select this threshold, the performances of the combination are as follows:

Sensitivity (Se)=67%; specificity (Spe)=72% (see Table 13 above).

The following rule is an example of a decision rule:

$$Z=0.2 \times A2M^t + 0.05 \times CXCL10^t - 0.026 \times IL8^t + 0.051 \times SPP1^t + 0.204 \times S100A4^t + 0.020 \times Age^t + 0.266 \times TG^t + 3.354 \times ALT^t + 0.141 \times GGT^t$$

(function Z16PROTsupp; see Table 12 above), where:

A2M, CXCL10, IL8, SPP1 and VIM are the measurement values BMK for the biomarkers, i.e. the measurement values for the seric levels of translation of the indicated genes (concentration of proteins in the serum), Age is the age of the patient at the date of sampling, TG, ALT and GGT are the values for the biological factors indicated (protein concentrations in the serum), and the exponent t (carried here by A2M, CXCL10, IL8, SPP1, S100A4, Age, TG, ALT and GGT) indicates that the value to be applied in the decision rule is the Box-Cox transformation (Box and Cox, 1964) of the measurement value of the level of expression (BMK) of the gene under consideration, in order to normalize it using the following formula:

$$BMK^t = (BMK^\lambda - 1)/\lambda.$$

In the example of a decision rule indicated above, the parameters $\lambda$ are 0.46 for A2M, 0.08 for CXCL10, 0.05 for IL8, 0.43 for SPP1 and −0.15 for S100A4, 0.9 for Age, −0.27 for TG, −0.13 for GGT and −0.47 for ALT (see Table 13 above).

If Z≥8.792, the diagnostic test is positive (mROC prediction=1), the subject is declared to be "F2".

If Z<8.792, the test is negative (mROC prediction=0), the subject is declared to be "F1".

REFERENCES

Anastasiadis et al. 2005; New globally convergent training scheme based on the resilient propagation algorithm. Neurocomputing 64: 253-270.

Bedossa, Poynard, for the French Metavir group, 1996. An algorithm for the grading of activity in chronic hepatitis C. Hepatology 24: 289-93.

Box and Cox 1964; An analysis of transformations. Journal of the Royal Statistical Society, Series B 26: 211-243.

Breiman 2001; Random Forests. Machine Learning 45: 5-32.

Castera et al. 2005; Prospective comparison of transient elastography, Fibrotest, APRI, and liver biopsy for the assessment of fibrosis in chronic hepatitis C; Gastroenterology 128:343-50.

Chambers 2008; Software for data analysis: programming with R. Springer, New York, ISBN 978-0-387-75935-7.

Cole et al. 1983; Proc. Natl. Acad. Sci. USA 80: 2026-2030.

Cole et al. 1985; Monoclonal Antibodies And Cancer Therapy, Alan R. Liss, Inc., pp. 77-96.

Dalgaard 2008; Introductory statistics with R, $2^{nd}$ edition, Springer, ISBN 978-0-387-79053.

Falissard 2005; Comprendre et utiliser les statistiques dans les sciences de la vie, [Understanding and using statistics in the life sciences], Masson.

Goodman 2007; Grading and staging systems for inflammation and fibrosis in chronic liver diseases. Journal of Hepatology 47: 598-607.

Hechenbichler and Schliep 2004; weighted k-nearest-neighbor techniques and ordinal classification. Sonderforschungsbereich 386, paper 399.

Hastie, Tibishirani and Friedman, 2009; "The Elements of Statistical Learning: Data Mining, Inference and Prediction", $2^{nd}$ Edition, Springer.

Ikata and Gentleman 1996; R: a language for data analysis and graphics. Journal of computational and graphical statistics 5: 299-314.

Intrator and Intrator 1993; Using Neural Nets for Interpretation of Nonlinear Models. Proceedings of the Statistical Computing Section, San Francisco: American Statistical Society (eds), pages 244-249.

Köhler and Milstein 1975; Nature 256: 495-497.

Kosbor et al. 1983; Immunology Today 4: 72.

Kramar et al. 1999; Critères ROC généralisés pour 1' évaluation de plusieurs marqueurs tumoraux [Generalized ROC criteria for the evaluation of a number of tumour markers]. Revue d'Epidémiologie and Santé Publique 47:376-383.

Kramar et al. 2001; mROC: a computer program for combining tumour markers in predicting disease states. Computer methods and programs in biomedicine 66: 199-207.

Liaw and Wiener 2002; Classification and regression by Random Forest. R. News 2.3: 18-22.

Livak and Schmittgen 2001; Analysis of relative gene expression data using real-time quantitative PCR and the 2(-Delta C(T)) Method. Methods 25: 402-408.

Riedmiller 1994; Rprop—Description and Implementation Details. Technical Report. University of Karlsruhe.

Riedmiller and Braun 1993; A direct adaptive method for faster backpropagation learning: the RPROP algorithm. Proceedings of the IEEE International Conference on Neural Networks (ICNN), San Francisco, pages 586-591.

Reiser and Faraggi 1997; Confidence intervals for the generalized ROC criterion. Biometrics 53: 644-652.

Schmitten and Livak 2008; Analyzing real-time PCR data by the comparative Ct method. Nature Protocols 3(6): 1101-1108.

Shaheen et al. 2007; FibroTest and FibroScan for the prediction of hepatitis C-related fibrosis: a systematic review of diagnostic test accuracy; Am. J. Gastroenterol. 102(11): 2589-2600.

Shapiro 1999; The interpretation of diagnostic tests. Statistical Methods in Medical Research, 8: 113-134.

Su and Liu 1993; Linear combinations of multiple diagnostic markers. Journal of the American Statistical Association 88: 1350-1355.

Swets 1988; Measuring the accuracy of diagnostic systems. Science 240, 1285-1293.

Theodoridis and Koutroumbos 2009; Pattern Recognition. Academic Press, Elsevier.

U.S. Pat. No. 4,376,110 (in the name of Hybritech Inc.).

WO 02/16949 A1 (in the name of Epigene).

WO 2006/103570 A2 (in the name of Assistance Publique—Hôpitaux de Paris).

WO 2006/082522 A1 (in the name of Assistance Publique—Hôpitaux de Paris).

---

The invention claimed is:

1. An in vitro method for determining the hepatic fibrosis score of a subject infected with one or more hepatitis viruses, characterized in that it comprises the following steps:
   i) in a sample which has been obtained from said subject, measuring the levels to which the selected genes are translated, said selected genes the levels of translation of which are measured being the following combination of genes:
   SPP1, A2M, IL8, CXCL10 and S100A4; and
   ii) comparing the measurement values of each of said selected genes obtained for said subject with their values, or with the distribution of their values, in reference cohorts which have been pre-established as a function of their hepatic fibrosis score, in order to classify said subject into that of those reference cohorts to which it has the highest probability of belonging,
   wherein the comparison in step ii) is made by combining said measurement values obtained in step i) into the linear Z function which is indicated for said combination of genes as:

$Z = 0.241 \times A2M^t + 0.137 \times CXCL10^t + 0.001 \times IL8^t + 0.062 \times SPP1^t + 0.226 \times S100A4^t$, and, optionally, by comparison of the output value obtained thereby with the threshold δ of 2.905;
   and wherein the classification of said subject into that of said reference cohorts to which it has the highest probability of belonging is made with:
   a sensitivity (Se) of at least 67%; and/or with
   a specificity (Sp) of at least 67%; and/or with
   a negative predictive value (NPV) of at least 81%; and/or with
   a positive predictive value (PPV) of at least 50%.

2. The method according to claim 1, in which:
   in addition to measuring the level at which the genes selected in step i) are translated, for said subject, the value of the following is measured, assayed or determined:
   one or more clinical factor(s) selected from: sex, age at the date of sampling, body mass index, insulin sensitivity index, diabetes, alcohol consumption, degree of steatosis, mode of contamination or Metavir activity; and/or
   one or more virological factor(s) selected from: viral genotype, duration of infection, viral load assayed for patient at treatment start date, or viral load assayed for patient at sampling date; and/or
   one or more biological factor(s) other than the levels of transcription or translation of said selected genes, selected from: concentration of haptoglobin, concentration of apolipoprotein A1, total bilirubin content, concentration of gamma glutamyl transpeptidase, concentration of aspartate aminotransferase, concentration of alanine aminotransferase (ALT), platelet count, prothrombin count, quantity of cholesterol HDL, total cholesterol, concentration of ferritin, level of glycaemia, concentration of peptide C, insulin level, concentration of triglycerides, quantity of albumin, transferrin saturation, and concentration of alkaline phosphatase, and in which
   in step ii), the value(s) for this (these) factor(s) and the measurement values for the level of translation of said genes selected in step i) are compared with their values or with the distribution of their values in reference cohorts which have been pre-established as a function of their hepatic fibrosis score in order to classify said subject into that of those reference cohorts to which it has the highest probability of belonging.

3. The method according to claim 1, in which said sample which has already been obtained from said subject is:
- a biological sample which has already been taken from said subject, or
- a sample comprising nucleic acids and/or proteins and/or polypeptides and/or peptides extracted or purified from said biological sample, or
- a sample comprising cDNAs which are susceptible of having been obtained by reverse transcription of said nucleic acids, said nucleic acids being RNAs,
said biological sample being
- a biological tissue or cell sample which has already been removed or collected from the liver of said subject, or
- a sample of biological fluid from said subject.

\* \* \* \* \*